US008399378B2

(12) United States Patent
Lee et al.

(10) Patent No.: US 8,399,378 B2
(45) Date of Patent: *Mar. 19, 2013

(54) USE OF NEONICOTINOIDS IN PEST CONTROL

(75) Inventors: Bruce Lee, Bad Krozingen (DE); Marius Sutter, Binningen (CH); Hubert Buholzer, Binningen (CH)

(73) Assignee: Syngenta Crop Protection LLC, Greensboro, NC (US)

( * ) Notice: Subject to any disclaimer, the term of this patent is extended or adjusted under 35 U.S.C. 154(b) by 170 days.

This patent is subject to a terminal disclaimer.

(21) Appl. No.: 12/191,707

(22) Filed: Aug. 14, 2008

(65) Prior Publication Data

US 2009/0163483 A1 Jun. 25, 2009

Related U.S. Application Data

(60) Continuation of application No. 11/456,939, filed on Jul. 12, 2006, now abandoned, which is a division of application No. 11/019,051, filed on Dec. 21, 2004, now Pat. No. 7,105,469, which is a division of application No. 10/125,136, filed on Apr. 18, 2002, now Pat. No. 6,844,339, which is a continuation of application No. 09/600,384, filed as application No. PCT/EP99/00183 on Jan. 14, 1999, now abandoned.

(30) Foreign Application Priority Data

Jan. 16, 1998 (CH) ............................. 80/98
Mar. 25, 1998 (CH) ............................ 706/98

(51) Int. Cl.
*A01N 25/26* (2006.01)
*A01N 43/40* (2006.01)
*A61K 31/44* (2006.01)
(52) U.S. Cl. .................... 504/100; 504/252; 514/342
(58) Field of Classification Search .................. None
See application file for complete search history.

(56) References Cited

U.S. PATENT DOCUMENTS

| 4,798,837 | A | 1/1989 | Drabek et al. |
| 4,849,432 | A | 7/1989 | Shiokawa et al. |
| 5,034,404 | A | 7/1991 | Uneme et al. |
| 6,022,871 | A | 2/2000 | Maienfisch et al. |
| 6,060,489 | A | 5/2000 | Erdelen et al. |
| 6,593,273 | B2 | 7/2003 | Asrar et al. |
| 6,844,339 | B2 * | 1/2005 | Lee et al. .................. 514/229.2 |
| 6,875,572 | B2 * | 4/2005 | Prudent et al. .................. 435/6.1 |
| 6,875,727 | B2 * | 4/2005 | Hofer et al. .................. 504/100 |

FOREIGN PATENT DOCUMENTS

| CA | 2005658 | 6/1990 |
| CA | 2146822 | 10/1995 |
| EP | 374753 | 6/1990 |
| EP | 580553 | 1/1994 |
| EP | 0677247 | 10/1995 |
| WO | 9416565 | 8/1994 |
| WO | 9601055 | 1/1996 |
| WO | 9628023 | 9/1996 |
| WO | 9637105 | 11/1996 |
| WO | 9726339 | 7/1997 |
| WO | 9740691 | 11/1997 |
| WO | 9740692 | 11/1997 |
| WO | 9745017 | 12/1997 |

OTHER PUBLICATIONS

Fife et al., (Field and cereal crops, Arthropod Management Test, vol. 22, pp. 251-252).*
Reed et al. (Field and cereal crops, Arthropod Management Test, vol. 22, p. 266).*
Burris et al. (Plant and animal resistance, Arthropod Management Test, vol. 2, pp. 422-423).*
Ruscoe et al. (Efficacy and duration of early season insecticides on transgenic Bt cotton, Proceedings of the Beltwide Cotton Conference, 1997,vol. 2: x-x, pp. 888-892).*
Scott et al., (Influence of early season treatments on insect populations and yield in bollgard and sure grow 501 cotton varieties, Proceedings of the Beltwide Cotton Conference, vol. 2, pp. 892-895).*
Database CABA, AN 1998; 103569, Eval. of XP00210251, Univ. of Ark. Spec. ref. No. 183, pp. 169-172 (1997); C.T. Allen.
Database CABA, AN 1998:68711, Infl Of—in Bollgard, Proceedings of Beltwide Cotton Conf. vol. 2, pp. 892-895, XP002102502, 1997, W.P. Scott, et al.
Database CABA, AN 1998:167903, lnfl. Of Proceeding of Beltwide Cotton Conf. vol. 2, pp. 1061-1064, XP002102503, 1998, D.D. Hardee.
Derwent Abstr. AN 97-89894, Effic of—Arthropod Manage Tests, vol. 22, p. 266, XP002102504, (1997), Reed et al.
Derwent Abstr. AN 97-89879, Effic of—Aphids on BT Cotton, Arthropod Manage Tests, vol. 22, p. 251-252, XP002102505 (1997), Fife et al.
Derwent Abstr., AN 95-89639, Arthropod Manage Tests, vol. 21, p. 422, XP002102506, (1997) Burris, et al.
CA 127:105569, Effic. And Duration/Transg. Cotton, Beltw-Cotton Conf., vol. 2, pp. 888-891, XP002102500, (1997), J. T. Ruscoe.

* cited by examiner

*Primary Examiner* — Alton Pryor
(74) *Attorney, Agent, or Firm* — James Cueva

(57) ABSTRACT

There is now described a method of controlling pests with nitroimino- or nitroguanidino-compounds; more specifically a method of controlling pests in and on transgenic crops of useful plants, such as, for example, in crops of maize, cereals, soya beans, tomatoes, cotton, potatoes, rice and mustard, with a nitroimino- or nitroguanidino-compound, especially with thiamethoxam, characterized in that a pesticidal composition comprising a nitroimino- or nitroguanidino-compound in free form or in agrochemically useful salt form and at least one auxiliary is applied to the pests or their environment, in particular to the crop plant itself.

8 Claims, No Drawings

USE OF NEONICOTINOIDS IN PEST CONTROL

This application is a continuation of U.S. patent application Ser. No. 11/456,939 filed on Jul. 12, 2006, which is a divisional application of U.S. patent application Ser. No. 11/019051, filed on Dec. 21, 2004, now U.S. Pat. No. 7,105,469, which is a divisional application of U.S. patent application Ser. No. 10/125,136, filed Apr. 18, 2002, now U.S. Pat. No. 6,844,339, which is a continuation of U.S. patent application Ser. No. 09/600,384, filed Sep. 21, 2000 (now abandoned) which is a national stage entry of PCT/EP99/00183 filed on Jan. 14, 1999 which claims priority to CH 80/98 filed on Jan. 16, 1998 and CH 706/98 filed on Mar. 25, 1998, the contents of all of which are incorporated herein by reference.

The present invention relates to a method of controlling pests with a nitroimino- or nitroguanidino-compound, especially thiamethoxam; more specifically to a novel method of controlling pests in and on transgenic crops of useful plants with a nitroimino- or nitroguanidino-compound.

Certain pest control methods are proposed in the literature. However, these methods are not fully satisfactory in the field of pest control, which is why there is a demand for providing further methods for controlling and combating pests, in particular insects and representatives of the order Acarina, or for protecting plants, especially crop plants. This object is achieved according to the invention by providing the present method.

The present invention therefore relates to a method of controlling pests in crops of transgenic useful plants, such as, for example, in crops of maize, cereals, soya beans, tomatoes, cotton, potatoes, rice and mustard, characterized in that a pesticidal composition comprising a nitroimino- or nitroguanidino-compound, especially thiamethoxam, imidacloprid, Ti-435 or thiacloprid in free form or in agrochemically useful salt form and at least one auxiliary is applied to the pests or their environment, in particular to the crop plant itself; to the use of the composition in question and to propagation material of transgenic plants which has been treated with it.

Surprisingly, it has now emerged that the use of a nitroimino- or nitroguanidino-compound compound for controlling pests on transgenic useful plants which contain—for instance—one or more genes expressing a pesticidally, particularly insecticidally, acaricidally, nematocidally or fugicidally active ingredient, or which are tolerant against herbicides or resistant against the attack of fungi, has a synergistic effect. It is highly surprising that the use of a nitroimino- or nitroguanidino-compound in combination with a transgenic plant exceeds the additive effect, to be expected in principle, on the pests to be controlled and thus extends the range of action of the nitroimino- or nitroguanidino-compound and of the active principle expressed by the transgenic plant in particular in two respects:

In particular, it has been found, surprisingly, that within the scope of invention the pesticidal activity of a nitroimino- or nitroguanidino-compound in combination with the effect expressed by the transgenic useful plant, is not only additive in comparison with the pesticidal activities of the nitroimino- or nitroguanidino-compound alone and of the transgenic crop plant alone, as can generally be expected, but that a synergistic effect is present. The term "synergistic", however, is in no way to be understood in this connection as being restricted to the pesticidal activity, but the term also refers to other advantageous properties of the method according to the invention compared with the nitroimino- or nitroguanidino-compound and the transgenic useful plant alone. Examples of such advantageous properties which may be mentioned are: extension of the pesticidal spectrum of action to other pests, for example to resistant strains; reduction in the application rate of the nitroimino- or nitroguanidino-compound, or sufficient control of the pests with the aid of the compositions according to the invention even at an application rate of the nitroimino- or nitroguanidino-compound alone and the transgenic useful plant alone are entirely ineffective; enhanced crop safety; improved quality of produce such as higher content of nutrient or oil, better fiber quality, enhanced shelf life, reduced content of toxic products such as mycotoxins, reduced content of residues or unfavorable constituents of any kind or better digestability; improved tolerance to unfavorable temperatures, draughts or salt content of water; enhanced assimilation rates such as nutrient uptake, water uptake and photosynthesis; favorable crop properties such as altered leaf aerea, reduced vegetative growth, increased yields, favorable seed shape/seed thickness or germination properties, altered colonialisation by saprophytes or epiphytes, reduction of senescense, improved phytoalexin production, improved of accelerated ripening, flower set increase, reduced boll fall and shattering, better attraction to beneficials and predators, increased pollination, reduced attraction to birds; or other advantages known to those skilled in the art.

Nitroimino- and nitroguanidino-compounds, such as thiamethoxam (5-(2-Chlorthiazol-5-ylmethyl)-3-methyl-4-nitroimino-perhydro-1,3,5-oxadiazin), are known from EP-A-0'580'553. Within the scope of invention thiamethoxam is preferred.

Also preferred within the scope of invention is imidacloprid of the formula

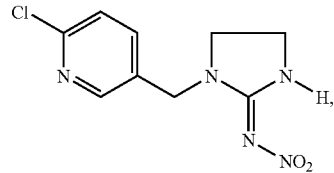

known from The Pesticide Manual, 10$^{th}$ Ed. (1991), The British Crop Protection Council, London, page 591;

also preferred is Thiacloprid of the formula

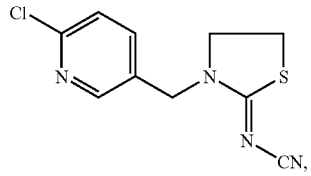

known from EP-A-235'725;

also preferred is the compound of the formula

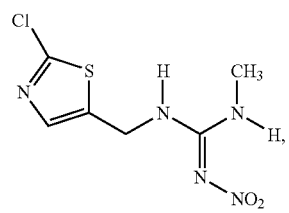

known as Ti-435 (Clothiamidin) from EP-A-376'279

The agrochemically compatible salts of the nitroimino- or nitroguanidino-compounds are, for example, acid addition salts of inorganic and organic acids, in particular of hydrochloric acid, hydrobromic acid, sulfuric acid, nitric acid, perchloric acid, phosphoric acid, formic acid, acetic acid, trifluoroacetic acid, oxalic acid, malonic acid, toluenesulfonic acid or benzoic acid. Preferred within the scope of the present invention is a composition known per se which comprises, as active ingredient, thiamethoxam and imidacloprid, each in the free form, especially thiamethoxam.

The transgenic plants used according to the invention are plants, or propagation material thereof, which are transformed by means of recombinant DNA technology in such a way that they are—for instance—capable of synthesizing selectively acting toxins as are known, for example, from toxin-producing invertebrates, especially of the phylum Arthropoda, as can be obtained from *Bacillus thuringiensis* strains; or as are known from plants, such as lectins; or in the alternative capable of expressing a herbicidal or fungicidal resistance. Examples of such toxins, or transgenic plants which are capable of synthesizing such toxins, have been disclosed, for example, in EP-A-0 374 753, WO 93/07278, WO 95/34656, EP-A-0 427 529 and EP-A-451 878 and are incorporated by reference in the present application.

The methods for generating such transgenic plants are widely known to those skilled in the art and described, for example, in the publications mentioned above.

The toxins which can be expressed by such transgenic plants include, for example, toxins, such as proteins which have insecticidal properties and which are expressed by transgenic plants, for example *Bacillus cereus* proteins or *Bacillus popliae* proteins; or *Bacillus thuringiensis* endotoxins (B.t.), such as CryIA(a), CryIA(b), CryIA(c), CryIIA, CryIIIA, CryIIIB2 or CytA; VIP1; VIP2; VIP3; or insecticidal proteins of bacteria colonising nematodes like *Photorhabdus* spp or *Xenorhabdus* spp such as *Photorhabdus luminescens, Xenorhabdus nematophilus* etc.; proteinase inhibitors, such as trypsin inhibitors, serine protease inhibitors, patatin, cystatin, papain inhibitors; ribosome-inactivating proteins (RIP), such as ricin, maize RIP, abrin, luffin, saporin or bryodin; plant lectins such as pea lectins, barley lectins or snowdrop lectins; or agglutinins; toxins produced by animals, such as scorpion toxins, spider venoms, wasp venoms and other insect-specific neurotoxins; steroid metabolism enzymes, such as 3-hydroxysteroid oxidase, ecdysteroid UDP-glycosyl transferase, cholesterol oxidases, ecdysone inhibitors, HMG-COA reductase, ion channel blockers such as sodium and calcium, juvenile hormone esterase, diuretic hormone receptors, stilbene synthase, bibenzyl synthase, chitinases and glucanases.

Examples of known transgenic plants which comprise one or more genes which encode insecticidal resistance and express one or more toxins are the following: KNOCKOUT® (maize), YIELDGARD® (maize); NUCOTN 33B® (cotton), BOLLGARD® (cotton), NEWLEAF® (potatoes), NATUREGARD® and PROTECTA®.

The following tables comprise further examples of targets and principles and crop phenotypes of transgenic crops which show tolerance against pests mainly insects, mites, nematodes, virus, bacteria and diseases or are tolerant to specific herbicides or classes of herbicides.

TABLE A1

| Crop: Maize | |
|---|---|
| Effected target or expressed principle(s) | Crop phenotype/Tolerance to |
| Acetolactate synthase (ALS) | Sulfonylureas, Imidazolinones, Triazolopyrimidines, Pyrimidyloxybenzoates, Phtalides |
| AcetylCoA Carboxylase (ACCase) | Aryloxyphenoxyalkanecarboxylic acids, cyclohexanediones |
| Hydroxyphenylpyruvate dioxygenase (HPPD) | Isoxazoles such as Isoxaflutol or Isoxachlortol, Triones such as mesotrione or sulcotrione |
| Phosphinothricin acetyl transferase | Phosphinothricin |
| O-Methyl transferase | altered lignin levels |
| Glutamine synthetase | Glufosinate, Bialaphos |
| Adenylosuccinate Lyase (ADSL) | Inhibitors of IMP and AMP synthesis |
| Adenylosuccinate Synthase | Inhibitors of adenylosuccinate synthesis |
| Anthranilate Synthase | Inhibitors of tryptophan synthesis and catabolism |
| Nitrilase | 3,5-dihalo-4-hydroxy-benzonitriles such as Bromoxynil and loxinyl |
| 5-Enolpyruvyl-3phosphoshikimate Synthase (EPSPS) | Glyphosate or sulfosate |
| Glyphosate oxidoreductase | Glyphosate or sulfosate |
| Protoporphyrinogen oxidase (PROTOX) | Diphenylethers, cyclic imides, phenylpyrazoles, pyridin derivatives, phenopylate, oxadiazoles etc. |
| Cytochrome P450 eg. P450 SU1 | Xenobiotics and herbicides such as Sulfonylureas |
| Dimboa biosynthesis (Bx1 gene) | *Helminthosporium turcicum, Rhopalosiphum maydis, Diplodia maydis, Ostrinia nubilalis,* lepidoptera sp. |
| CMIII (small basic maize seed peptide | plant pathogenes eg. *fusarium, alternaria, sclerotina* |
| Corn-SAFP (zeamatin) | plant pathogenes eg. *fusarium, alternaria, sclerotina, rhizoctonia, chaetomium, phycomyces* |
| Hm1 gene | Cochliobulus |
| Chitinases | plant pathogenes |
| Glucanases | plant pathogenes |

TABLE A1-continued

Crop: Maize

| Effected target or expressed principle(s) | Crop phenotype/Tolerance to |
| --- | --- |
| Coat proteins | viruses such as maize dwarf mosaic virus, maize chlorotic dwarf virus |
| *Bacillus thuringiensis* toxins, VIP 3, *Bacillus cereus* toxins, *Photorabdus* and *Xenorhabdus* toxins | lepidoptera, coleoptera, diptera, nematodes, eg. *ostrinia nubilalis*, *heliothis zea*, armyworms eg. *spodoptera frugiperda*, corn rootworms, *sesamia* sp., black cutworm, asian corn borer, weevils |
| 3-Hydroxysteroid oxidase | lepidoptera, coleoptera, diptera, nematodes, eg. *ostrinia nubilalis*, *heliothis zea*, armyworms eg. *spodoptera frugiperda*, corn rootworms, *sesamia* sp., black cutworm, asian corn borer, weevils |
| Peroxidase | lepidoptera, coleoptera, diptera, nematodes, eg. *ostrinia nubilalis*, *heliothis zea*, armyworms eg. *spodoptera frugiperda*, corn rootworms, *sesamia* sp., black cutworm, asian corn borer, weevils |
| Aminopeptidase inhibitors eg. Leucine aminopeptidase inhibitor (LAPI) | lepidoptera, coleoptera, diptera, nematodes, eg. *ostrinia nubilalis*, *heliothis zea*, armyworms eg. *spodoptera frugiperda*, corn rootworms, *sesamia* sp., black cutworm, asian corn borer, weevils |
| Limonene synthase | corn rootworms |
| Lectines | lepidoptera, coleoptera, diptera, nematodes, eg. *ostrinia nubilalis*, *heliothis zea*, armyworms eg. *spodoptera frugiperda*, corn rootworms, *sesamia* sp., black cutworm, asian corn borer, weevils |
| Protease Inhibitors eg. cystatin, patatin, virgiferin, CPTI | weevils, corn rootworm |
| ribosome inactivating protein | lepidoptera, coleoptera, diptera, nematodes, eg. *ostrinia nubilalis*, *heliothis zea*, armyworms eg. *spodoptera frugiperda*, corn rootworms, *sesamia* sp., black cutworm, asian corn borer, weevils |
| maize 5C9 polypeptide | lepidoptera, coleoptera, diptera, nematodes, eg. *ostrinia nubilalis*, *heliothis zea*, armyworms eg. *spodoptera frugiperda*, corn rootworms, *sesamia* sp., black cutworm, asian corn borer, weevils |
| HMG-CoA reductase | lepidoptera, coleoptera, diptera, nematodes, eg. *ostrinia nubilalis*, *heliothis zea*, armyworms eg. *spodoptera frugiperda*, corn rootworms, *sesamia* sp., black cutworm, asian corn borer, weevils |

TABLE A2

Crop Wheat

| Effected target or expressed principle(s) | Crop phenotype/Tolerance to |
| --- | --- |
| Acetolactate synthase (ALS) | Sulfonylureas, Imidazolinones, Triazolopyrimidines, Pyrimidyloxybenzoates, Phtalides |
| AcetylCoA Carboxylase (ACCase) | Aryloxyphenoxyalkanecarboxylic acids, cyclohexanediones |
| Hydroxyphenylpyruvate dioxygenase (HPPD) | Isoxazoles such as Isoxaflutol or Isoxachlortol, Triones such as mesotrione or sulcotrione |
| Phosphinothricin acetyl transferase | Phosphinothricin |
| O-Methyl transferase | altered lignin levels |
| Glutamine synthetase | Glufosinate, Bialaphos |
| Adenylosuccinate Lyase (ADSL) | Inhibitors of IMP and AMP synthesis |
| Adenylosuccinate Synthase | Inhibitors of adenylosuccinate synthesis |
| Anthranilate Synthase | Inhibitors of tryptophan synthesis and catabolism |
| Nitrilase | 3,5-dihalo-4-hydroxy-benzonitriles such as Bromoxynil and Ioxinyl |
| 5-Enolpyruvyl-3phosphoshikimate Synthase (EPSPS) | Glyphosate or sulfosate |
| Glyphosate oxidoreductase | Glyphosate or sulfosate |

TABLE A2-continued

Crop Wheat

| Effected target or expressed principle(s) | Crop phenotype/Tolerance to |
|---|---|
| Protoporphyrinogen oxidase (PROTOX) | Diphenylethers, cyclic imides, phenylpyrazoles, pyridin derivatives, phenopylate, oxadiazoles etc. |
| Cytochrome P450 eg. P450 SU1 | Xenobiotics and herbicides such as Sulfonylureas |
| Antifungal polypeptide AlyAFP | plant pathogenes eg *septoria* and *fusarioum* |
| glucose oxidase | plant pathogenes eg. *fusarium, septoria* |
| pyrrolnitrin synthesis genes | plant pathogenes eg. *fusarium, septoria* |
| serine/threonine kinases | plant pathogenes eg. *fusarium, septoria* and other diseases |
| Hypersensitive response eliciting polypeptide | plant pathogenes eg. *fusarium, septoria* and other diseases |
| Systemic acquires resistance (SAR) genes | viral, bacterial, fungal, nematodal pathogens |
| Chitinases | plant pathogenes |
| Glucanases | plant pathogenes |
| double stranded ribonuclease | viruses such as BYDV and MSMV |
| Coat proteins | viruses such as BYDV and MSMV |
| *Bacillus thuringiensis* toxins, VIP 3, *Bacillus cereus* toxins, *Photorabdus* and *Xenorhabdus* toxins | lepidoptera, coleoptera, diptera, nematodes, |
| 3-Hydroxysteroid oxidase | lepidoptera, coleoptera, diptera, nematodes, |
| Peroxidase | lepidoptera, coleoptera, diptera, nematodes, |
| Aminopeptidase inhibitors eg. Leucine aminopeptidase inhibitor | lepidoptera, coleoptera, diptera, nematodes, |
| Lectines | lepidoptera, coleoptera, diptera, nematodes, aphids |
| Protease Inhibitors eg. cystatin, patatin, virgiferin, CPTI | lepidoptera, coleoptera, diptera, nematodes, aphids |
| ribosome inactivating protein | lepidoptera, coleoptera, diptera, nematodes, aphids |
| HMG-CoA reductase | lepidoptera, coleoptera, diptera, nematodes, eg. *ostrinia nubilalis*, *heliothis zea*, armyworms eg. *spodoptera frugiperda*, corn rootworms, *sesamia* sp., black cutworm, asian corn borer, weevils |

TABLE A3

Crop Barley

| Effected target or expressed principle(s) | Crop phenotype/Tolerance to |
|---|---|
| Acetolactate synthase (ALS) | Sulfonylureas, Imidazolinones, Triazolopyrimidines, Pyrimidyloxybenzoates, Phtalides |
| AcetylCoA Carboxylase (ACCase) | Aryloxyphenoxyalkanecarboxylic acids, cyclohexanediones |
| Hydroxyphenylpyruvate dioxygenase (HPPD) | Isoxazoles such as Isoaflutol or Isoxachlortol, Triones such as mesotrione or sulcotrione |
| Phosphinothricin acetyl transferase O-Methyl transferase | Phosphinothricin altered lignin levels |
| Glutamine synthetase | Glufosinate, Bialaphos |
| Adenylosuccinate Lyase (ADSL) | Inhibitors of IMP and AMP synthesis |
| Adenylosuccinate Synthase | Inhibitors of adenylosuccinate synthesis |
| Anthranilate Synthase | Inhibitors of tryptophan synthesis and catabolism |
| Nitrilase | 3,5-dihalo-4-hydroxy-benzonitriles such as Bromoxynil and Ioxinyl |
| 5-Enolpyruvyl-3phosphoshikimate Synthase (EPSPS) | Glyphosate or sulfosate |
| Glyphosate oxidoreductase | Glyphosate or sulfosate |
| Protoporphyrinogen oxidase (PROTOX) | Diphenylethers, cyclic imides, phenylpyrazoles, pyridin derivatives, phenopylate, oxadiazoles etc. |
| Cytochrome P450 eg. P450 SU1 | Xenobiotics and herbicides such as Sulfonylureas |
| Antifungal polypeptide AlyAFP | plant pathogenes eg *septoria* and *fusarioum* |
| glucose oxidase | plant pathogenes eg. *fusarium, septoria* |
| pyrrolnitrin synthesis genes | plant pathogenes eg. *fusarium, septoria* |
| serine/threonine kinases | plant pathogenes eg. *fusarium, septoria* and other diseases |
| Hypersensitive response eliciting polypeptide | plant pathogenes eg. *fusarium, septoria* and other diseases |
| Systemic acquires resistance (SAR) genes | viral, bacterial, fungal, nematodal pathogens |
| Chitinases | plant pathogenes |
| Glucanases | plant pathogenes |
| double stranded ribonuclease | viruses such as BYDV and MSMV |
| Coat proteins | viruses such as BYDV and MSMV |
| *Bacillus thuringiensis* toxins, VIP 3, *Bacillus cereus* toxins, *Photorabdus* and *Xenorhabdus* toxins | lepidoptera, coleoptera, diptera, nematodes, |
| 3-Hydroxysteroid oxidase | lepidoptera, coleoptera, diptera, nematodes, |
| Peroxidase | lepidoptera, coleoptera, diptera, nematodes, |
| Aminopeptidase inhibitors eg. Leucine aminopeptidase inhibitor | lepidoptera, coleoptera, diptera, nematodes, |
| Lectines | lepidoptera, coleoptera, diptera, nematodes, aphids |

TABLE A3-continued

Crop Barley

| Effected target or expressed principle(s) | Crop phenotype/Tolerance to |
|---|---|
| Protease Inhibitors eg. cystatin, patatin, virgiferin, CPTI | lepidoptera, coleoptera, diptera, nematodes, aphids |
| ribosome inactivating protein | lepidoptera, coleoptera, diptera, nematodes, aphids |
| HMG-CoA reductase | lepidoptera, coleoptera, diptera, nematodes, aphids |

TABLE A4

Crop Rice

| Effected target or expressed principle(s) | Crop phenotype/Tolerance to |
|---|---|
| Acetolactate synthase (ALS) | Sulfonylureas, Imidazolinones, Triazolopyrimidines, Pyrimidyloxybenzoates, Phtalides |
| AcetylCoA Carboxylase (ACCase) | Aryloxyphenoxyalkanecarboxylic acids, cyclohexanediones |
| Hydroxyphenylpyruvate dioxygenase (HPPD) | Isoxazoles such as Isoxaflutol or Isoxachlortol, Triones such as mesotrione or sulcotrione |
| Phosphinothricin acetyl transferase | Phosphinothricin |
| O-Methyl transferase | altered lignin levels |
| Glutamine synthetase | Glufosinate, Bialaphos |
| Adenylosuccinate Lyase (ADSL) | Inhibitors of IMP and AMP synthesis |
| Adenylosuccinate Synthase | Inhibitors of adenylosuccinate synthesis |
| Anthranilate Synthase | Inhibitors of tryptophan synthesis and catabolism |
| Nitrilase | 3,5-dihalo-4-hydroxy-benzonitriles such as Bromoxynil and Ioxinyl |
| 5-Enolpyruvyl-3phosphoshikimate Synthase (EPSPS) | Glyphosate or sulfosate |
| Glyphosate oxidoreductase | Glyphosate or sulfosate |
| Protoporphyrinogen oxidase (PROTOX) | Diphenylethers, cyclic imides, phenylpyrazoles, pyridin derivatives, phenopylate, oxadiazoles etc. |
| Cytochrome P450 eg. P450 SU1 | Xenobiotics and herbicides such as Sulfonylureas |
| Antifungal polypeptide AlyAFP | plant pathogenes |
| glucose oxidase | plant pathogenes |
| pyrrolnitrin synthesis genes | plant pathogenes |
| serine/threonine kinases | plant pathogenes |
| Phenylalanine ammonia lyase (PAL) | plant pathogenes eg bacterial leaf blight and rice blast, inducible |
| phytoalexins | plant pathogenes eg bacterial leaf blight and rice blast |
| B-1,3-glucanase antisense | plant pathogenes eg bacterial leaf blight and rice blast |
| receptor kinase | plant pathogenes eg bacterial leaf blight and rice blast |
| Hypersensitive response eliciting polypeptide | plant pathogenes |
| Systemic acquires resistance (SAR) genes | viral, bacterial, fungal, nematodal pathogens |
| Chitinases | plant pathogenes eg bacterial leaf blight and rice blast |
| Glucanases | plant pathogenes |
| double stranded ribonuclease | viruses such as BYDV and MSMV |
| Coat proteins | viruses such as BYDV and MSMV |
| Bacillus thuringiensis toxins, VIP 3, Bacillus cereus toxins, Photorabdus and Xenorhabdus toxins | lepidoptera eg. stemborer, coleoptera eg rice water weevil, diptera, rice hoppers eg brown rice hopper |
| 3-Hydroxysteroid oxidase | lepidoptera eg. stemborer, coleoptera eg rice water weevil, diptera, rice hoppers eg brown rice hopper |
| Peroxidase | lepidoptera eg. stemborer, coleoptera eg rice water weevil, diptera, rice hoppers eg brown rice hopper |
| Aminopeptidase inhibitors eg. Leucine aminopeptidase inhibitor | lepidoptera eg. stemborer, coleoptera eg rice water weevil, diptera, rice hoppers eg brown rice hopper |
| Lectines | lepidoptera eg. stemborer, coleoptera eg rice water weevil, diptera, rice hoppers eg brown rice hopper |

TABLE A4-continued

Crop Rice

| Effected target or expressed principle(s) | Crop phenotype/Tolerance to |
|---|---|
| Protease Inhibitors, | lepidoptera eg. stemborer, coleoptera eg rice water weevil, diptera, rice hoppers eg brown rice hopper |
| ribosome inactivating protein | lepidoptera eg. stemborer, coleoptera eg rice water weevil, diptera, rice hoppers eg brown rice hopper |
| HMG-CoA reductase | lepidoptera eg. stemborer, coleoptera eg rice water weevil, diptera, rice hoppers eg brown rice hopper |

TABLE A5

Crop Soya

| Effected target or expressed principle(s) | Crop phenotype/Tolerance to |
|---|---|
| Acetolactate synthase (ALS) | Sulfonylureas, Imidazolinones, Triazolopyrimidines, Pyrimidyloxybenzoates, Phtalides |
| AcetylCoA Carboxylase (ACCase) | Aryloxyphenoxyalkanecarboxylic acids, cyclohexanediones |
| Hydroxyphenylpyruvate dioxygenase (HPPD) | Isoxazoles such as Isoxaflutol or Isoxachlortol, Triones such as mesotrione or sulcotrione |
| Phosphinothricin acetyl transferase | Phosphinothricin |
| O-Methyl transferase | altered lignin levels |
| Glutamine synthetase | Glufosinate, Bialaphos |
| Adenylosuccinate Lyase (ADSL) | Inhibitors of IMP and AMP synthesis |
| Adenylosuccinate Synthase | Inhibitors of adenylosuccinate synthesis |
| Anthranilate Synthase | Inhibitors of tryptophan synthesis and catabolism |
| Nitrilase | 3,5-dihalo-4-hydroxy-benzonitriles such as Bromoxynil and Ioxinyl |
| 5-Enolpyruvyl-3phosphoshikimate Synthase (EPSPS) | Glyphosate or sulfosate |
| Glyphosate oxidoreductase | Glyphosate or sulfosate |
| Protoporphyrinogen oxidase (PROTOX) | Diphenylethers, cyclic imides, phenylpyrazoles, pyridin derivatives, phenopylate, oxadiazoles etc. |
| Cytochrome P450 eg. P450 SU1 or selection | Xenobiotics and herbicides such as Sulfonylureas |
| Antifungal polypeptide AlyAFP | bacterial and fungal pathogens such as *fusarium*, *sclerotinia*, stemrot |
| oxalate oxidase | bacterial and fungal pathogens such as *fusarium*, *sclerotinia*, stemrot |
| glucose oxidase | bacterial and fungal pathogens such as *fusarium*, *sclerotinia*, stemrot |
| pyrrolnitrin synthesis genes | bacterial and fungal pathogens such as *fusarium*, *sclerotinia*, stemrot |
| serine/threonine kinases | bacterial and fungal pathogens such as *fusarium*, *sclerotinia*, stemrot |
| Phenylalanine ammonia lyase (PAL) | bacterial and fungal pathogens such as *fusarium*, *sclerotinia*, stemrot |
| phytoalexins | plant pathogenes eg bacterial leaf blight and rice blast |
| B-1,3-glucanase antisense | plant pathogenes eg bacterial leaf blight and rice blast |
| receptor kinase | bacterial and fungal pathogens such as *fusarium*, *sclerotinia*, stemrot |
| Hypersensitive response eliciting polypeptide | plant pathogenes |
| Systemic acquires resistance (SAR) genes | viral, bacterial, fungal, nematodal pathogens |
| Chitinases | bacterial and fungal pathogens such as *fusarium*, *sclerotinia*, stemrot |
| Glucanases | bacterial and fungal pathogens such as *fusarium*, *sclerotinia*, stemrot |
| double stranded ribonuclease | viruses such as BPMV and SbMV |
| Coat proteins | viruses such as BYDV and MSMV |
| *Bacillus thuringiensis* toxins, VIP 3, *Bacillus cereus* toxins, *Photorabdus* and *Xenorhabdus* toxins | lepidoptera, coleoptera, aphids |
| 3-Hydroxysteroid oxidase | lepidoptera, coleoptera, aphids |
| Peroxidase | lepidoptera, coleoptera, aphids |

TABLE A5-continued

Crop Soya

| Effected target or expressed principle(s) | Crop phenotype/Tolerance to |
| --- | --- |
| Aminopeptidase inhibitors eg. Leucine aminopeptidase inhibitor | lepidoptera, coleoptera, aphids |
| Lectines | lepidoptera, coleoptera, aphids |
| Protease Inhibitors eg virgiferin | lepidoptera, coleoptera, aphids |
| ribosome inactivating protein | lepidoptera, coleoptera, aphids |
| HMG-CoA reductase | lepidoptera, coleoptera, aphids |
| Barnase | nematodes eg root knot nematodes and cyst nematodes |
| Cyst nematode hatching stimulus | cyst nematodes |
| Antifeeding principles | nematodes eg root knot nematodes and cyst nematodes |

TABLE A6

Crop Potatoes

| Effected target or expressed principle(s) | Crop phenotype/Tolerance to |
| --- | --- |
| Acetolactate synthase (ALS) | Sulfonylureas, Imidazolinones, Triazolopyrimidines, Pyrimidyloxybenzoates, Phtalides |
| AcetylCoA Carboxylase (ACCase) | Aryloxyphenoxyalkanecarboxylic acids, cyclohexanediones |
| Hydroxyphenylpyruvate dioxygenase (HPPD) | Isoxazoles such as Isoxaflutol or Isoxachlortol, Triones such as mesotrione or sulcotrione |
| Phosphinothricin acetyl transferase | Phosphinothricin |
| O-Methyl transferase | altered lignin levels |
| Glutamine synthetase | Glufosinate, Bialaphos |
| Adenylosuccinate Lyase (ADSL) | Inhibitors of IMP and AMP synthesis |
| Adenylosuccinate Synthase | Inhibitors of adenylosuccinate synthesis |
| Anthranilate Synthase | Inhibitors of tryptophan synthesis and catabolism |
| Nitrilase | 3,5-dihalo-4-hydroxy-benzonitriles such as Bromoxynil and Ioxinyl |
| 5-Enolpyruvyl-3phosphoshikimate Synthase (EPSPS) | Glyphosate or sulfosate |
| Glyphosate oxidoreductase | Glyphosate or sulfosate |
| Protoporphyrinogen oxidase (PROTOX) | Diphenylethers, cyclic imides, phenylpyrazoles, pyridin derivatives, phenopylate, oxadiazoles etc. |
| Cytochrome P450 eg. P450 SU1 or selection | Xenobiotics and herbicides such as Sulfonylureas |
| Polyphenol oxidase or Polyphenol oxidase antisense | blackspot bruise |
| Metallothionein | bacterial and fungal pathogens such as *phytophtora* |
| Ribonuclease | *Phytophtora, Verticillium, Rhizoctonia* |
| Antifungal polypeptide AlyAFP | bacterial and fungal pathogens such as *phytophtora* |
| oxalate oxidase | bacterial and fungal pathogens such as *Phytophtora, Verticillium, Rhizoctonia* |
| glucose oxidase | bacterial and fungal pathogens such as *Phytophtora, Verticillium, Rhizoctonia* |
| pyrrolnitrin synthesis genes | bacterial and fungal pathogens such as *Phytophtora, Verticillium, Rhizoctonia* |
| serine/threonine kinases | bacterial and fungal pathogens such as *Phytophtora, Verticillium, Rhizoctonia* |
| Cecropin B | bacteria such as corynebacterium *sepedonicum, Erwinia carotovora* |
| Phenylalanine ammonia lyase (PAL) | bacterial and fungal pathogens such as *Phytophtora, Verticillium, Rhizoctonia* |
| phytoalexins | bacterial and fungal pathogens such as *Phytophtora, Verticillium, Rhizoctonia* |
| B-1,3-glucanase antisense | bacterial and fungal pathogens such as *Phytophtora, Verticillium, Rhizoctonia* |
| receptor kinase | bacterial and fungal pathogens such as *Phytophtora, Verticillium, Rhizoctonia* |
| Hypersensitive response eliciting polypeptide | bacterial and fungal pathogens such as Phytophtora, *Verticillium, Rhizoctonia* |
| Systemic acquires resistance (SAR) genes | viral, bacterial, fungal, nematodal pathogens |

TABLE A6-continued

Crop Potatoes

| Effected target or expressed principle(s) | Crop phenotype/Tolerance to |
|---|---|
| Chitinases | bacterial and fungal pathogens such as *Phytophtora, Verticillium, Rhizoctonia* |
| Barnase | bacterial and fungal pathogens such as *Phytophtora, Verticillium, Rhizoctonia* |
| Disease resistance response gene 49 | bacterial and fungal pathogens such as *Phytophtora, Verticillium, Rhizoctonia* |
| trans aldolase antisense | blackspots |
| Glucanases | bacterial and fungal pathogens such as *Phytophtora, Verticillium, Rhizoctonia* |
| double stranded ribonuclease | viruses such as PLRV, PVY and TRV |
| Coat proteins | viruses such as PLRV, PVY and TRV |
| 17 kDa or 60 kDa protein | viruses such as PLRV, PVY and TRV |
| Nuclear inclusion proteins eg. a or b | viruses such as PLRV, PVY and TRV |
| Pseudoubiquitin | viruses such as PLRV, PVY and TRV |
| Replicase | viruses such as PLRV, PVY and TRV |
| *Bacillus thuringiensis* toxins, VIP 3, *Bacillus cereus* toxins, *Photorabdus* and *Xenorhabdus* toxins | coleoptera eg colorado potato beetle, aphids |
| 3-Hydroxysteroid oxidase | coleoptera eg colorado potato beetle, aphids |
| Peroxidase | coleoptera eg colorado potato beetle, aphids |
| Aminopeptidase inhibitors eg. Leucine aminopeptidase inhibitor | coleoptera eg colorado potato beetle, aphids |
| stilbene synthase | coleoptera eg colorado potato beetle, aphids |
| Lectines | coleoptera eg colorado potato beetle, aphids |
| Protease Inhibitors eg cystatin, patatin | coleoptera eg colorado potato beetle, aphids |
| ribosome inactivating protein | coleoptera eg colorado potato beetle, aphids |
| HMG-CoA reductase | coleoptera eg colorado potato beetle, aphids |
| Cyst nematode hatching stimulus | cyst nematodes |
| Barnase | nematodes eg root knot nematodes and cyst nematodes |
| Antifeeding principles | nematodes eg root knot nematodes and cyst nematodes |

TABLE A7

Crop Tomatoes

| Effected target or expressed principle(s) | Crop phenotype/Tolerance to |
|---|---|
| Acetolactate synthase (ALS) | Sulfonylureas, Imidazolinones, Triazolopyrimidines, Pyrimidyloxybenzoates, Phtalides |
| AcetylCoA Carboxylase (ACCase) | Aryloxyphenoxyalkanecarboxylic acids, cyclohexanediones |
| Hydroxyphenylpyruvate dioxygenase (HPPD) | Isoxazoles such as Isoxaflutol or Isoxachlortol, Triones such as mesotrione or sulcotrione |
| Phosphinothricin acetyl transferase | Phosphinothricin |
| O-Methyl transferase | altered lignin levels |
| Glutamine synthetase | Glufosinate, Bialaphos |
| Adenylosuccinate Lyase (ADSL) | Inhibitors of IMP and AMP synthesis |
| Adenylosuccinate Synthase | Inhibitors of adenylosuccinate synthesis |
| Anthranilate Synthase | Inhibitors of tryptophan synthesis and catabolism |
| Nitrilase | 3,5-dihalo-4-hydroxy-benzonitriles such as Bromoxynil and Ioxinyl |
| 5-Enolpyruvyl-3phosphoshikimate Synthase (EPSPS) | Glyphosate or sulfosate |
| Glyphosate oxidoreductase | Glyphosate or sulfosate |
| Protoporphyrinogen oxidase (PROTOX) | Diphenylethers, cyclic imides, phenylpyrazoles, pyridin derivatives, phenopylate, oxadiazoles etc. |
| Cytochrome P450 eg. P450 SU1 or selection | Xenobiotics and herbicides such as Sulfonylureas |

TABLE A7-continued

| Crop Tomatoes | |
|---|---|
| Effected target or expressed principle(s) | Crop phenotype/Tolerance to |
| Polyphenol oxidase or Polyphenol oxidase antisense | blackspot bruise |
| Metallothionein | bacterial and fungal pathogens such as *phytophtora* |
| Ribonuclease | *Phytophtora*, *Verticillium*, *Rhizoctonia* |
| Antifungal polypeptide AlyAFP | bacterial and fungal pathogens such as bacterial speck, *fusarium*, soft rot, powdery mildew, crown rot, leaf mould etc. |
| oxalate oxidase | bacterial and fungal pathogens such as bacterial speck, *fusarium*, soft rot, powdery mildew, crown rot, leaf mould etc. |
| glucose oxidase | bacterial and fungal pathogens such as bacterial speck, *fusarium*, soft rot, powdery mildew, crown rot, leaf mould etc. |
| pyrrolnitrin synthesis genes | bacterial and fungal pathogens such as bacterial speck, *fusarium*, soft rot, powdery mildew, crown rot, leaf mould etc. |
| serine/threonine kinases | bacterial and fungal pathogens such as bacterial speck, *fusarium*, soft rot, powdery mildew, crown rot, leaf mould etc. |
| Cecropin B | bacterial and fungal pathogens such as bacterial speck, *fusarium*, soft rot, powdery mildew, crown rot, leaf mould etc. |
| Phenylalanine ammonia lyase (PAL) | bacterial and fungal pathogens such as bacterial speck, *fusarium*, soft rot, powdery mildew, crown rot, leaf mould etc. |
| Cf genes eg. Cf 9 Cf5 Cf4 Cf2 | leaf mould |
| Osmotin | *alternaria solani* |
| Alpha Hordothionin | bacteria |
| Systemin | bacterial and fungal pathogens such as bacterial speck, *fusarium*, soft rot, powdery mildew, crown rot, leaf mould etc. |
| Polygalacturonase inhibitors | bacterial and fungal pathogens such as bacterial speck, *fusarium*, soft rot, powdery mildew, crown rot, leaf mould etc. |
| Prf regulatory gene | bacterial and fungal pathogens such as bacterial speck, *fusarium*, soft rot, powdery mildew, crown rot, leaf mould etc. |
| I2 *Fusarium* resistance locus | *fusarium* |
| phytoalexins | bacterial and fungal pathogens such as bacterial speck, *fusarium*, soft rot, powdery mildew, crown rot, leaf mould etc. |
| B-1,3-glucanase antisense | bacterial and fungal pathogens such as bacterial speck, *fusarium*, soft rot, powdery mildew, crown rot, leaf mould etc. |
| receptor kinase | bacterial and fungal pathogens such as bacterial speck, *fusarium*, soft rot, powdery mildew, crown rot, leaf mould etc. |
| Hypersensitive response eliciting polypeptide | bacterial and fungal pathogens such as bacterial speck, *fusarium*, soft rot, powdery mildew, crown rot, leaf mould etc. |
| Systemic acquires resistance (SAR) genes | viral, bacterial, fungal, nematodal pathogens |
| Chitinases | bacterial and fungal pathogens such as bacterial speck, *fusarium*, soft rot, powdery mildew, crown rot, leaf mould etc. |
| Barnase | bacterial and fungal pathogens such as bacterial speck, *fusarium*, soft rot, powdery mildew, crown rot, leaf mould etc. |

TABLE A7-continued

Crop Tomatoes

| Effected target or expressed principle(s) | Crop phenotype/Tolerance to |
|---|---|
| Glucanases | bacterial and fungal pathogens such as bacterial speck, *fusarium*, soft rot, powdery mildew, crown rot, leaf mould etc. |
| double stranded ribonuclease | viruses such as PLRV, PVY and ToMoV |
| Coat proteins | viruses such as PLRV, PVY and ToMoV |
| 17 kDa or 60 kDa protein | viruses such as PLRV, PVY and ToMoV |
| Nuclear inclusion proteins eg. a or b or Nucleoprotein | viruses such as PLRV, PVY and ToMoV TRV |
| Pseudoubiquitin | viruses such as PLRV, PVY and ToMoV |
| Replicase | viruses such as PLRV, PVY and ToMoV |
| *Bacillus thuringiensis* toxins, VIP 3, *Bacillus cereus* toxins, *Photorabdus* and *Xenorhabdus* toxins | lepidoptera eg *heliothis*, whiteflies aphids |
| 3-Hydroxysteroid oxidase | lepidoptera eg *heliothis*, whiteflies aphids |
| Peroxidase | lepidoptera eg *heliothis*, whiteflies aphids |
| Aminopeptidase inhibitors eg. Leucine aminopeptidase inhibitor | lepidoptera eg *heliothis*, whiteflies aphids |
| Lectines | lepidoptera eg *heliothis*, whiteflies aphids |
| Protease Inhibitors eg cystatin, patatin | lepidoptera eg *heliothis*, whiteflies aphids |
| ribosome inactivating protein | lepidoptera eg *heliothis*, whiteflies aphids |
| stilbene synthase | lepidoptera eg *heliothis*, whiteflies aphids |
| HMG-CoA reductase | lepidoptera eg *heliothis*, whiteflies aphids |
| Cyst nematode hatching stimulus | cyst nematodes |
| Barnase | nematodes eg root knot nematodes and cyst nematodes |
| Antifeeding principles | nematodes eg root knot nematodes and cyst nematodes |

TABLE A8

Crop Peppers

| Effected target or expressed principle(s) | Crop phenotype/Tolerance to |
|---|---|
| Acetolactate synthase (ALS) | Sulfonylureas, Imidazolinones, Triazolopyrimidines, Pyrimidyloxybenzoates, Phtalides |
| AcetylCoA Carboxylase (ACCase) | Aryloxyphenoxyalkanecarboxylic acids, cyclohexanediones |
| Hydroxyphenylpyruvate dioxygenase (HPPD) | Isoxazoles such as Isoxaflutol or Isoxachlortol, Triones such as mesotrione or sulcotrione |
| Phosphinothricin acetyl transferase | Phosphinothricin |
| O-Methyl transferase | altered lignin levels |
| Glutamine synthetase | Glufosinate, Bialaphos |
| Adenylosuccinate Lyase (ADSL) | Inhibitors of IMP and AMP synthesis |
| Adenylosuccinate Synthase | Inhibitors of adenylosuccinate synthesis |
| Anthranilate Synthase | Inhibitors of tryptophan synthesis and catabolism |
| Nitrilase | 3,5-dihalo-4-hydroxy-benzonitriles such as Bromoxynil and Ioxinyl |
| 5-Enolpyruvyl-3phosphoshikimate Synthase (EPSPS) | Glyphosate or sulfosate |
| Glyphosate oxidoreductase | Glyphosate or sulfosate |
| Protoporphyrinogen oxidase (PROTOX) | Diphenylethers, cyclic imides, phenylpyrazoles, pyridin derivatives, phenopylate, oxadiazoles etc. |
| Cytochrome P450 eg. P450 SU1 or selection | Xenobiotics and herbicides such as Sulfonylureas |
| Polyphenol oxidase or Polyphenol oxidase antisense | bacterial and fungal pathogens |
| Metallothionein | bacterial and fungal pathogens |
| Ribonuclease | bacterial and fungal pathogens |
| Antifungal polypeptide AlyAFP | bacterial and fungal pathogens |
| oxalate oxidase | bacterial and fungal pathogens |
| glucose oxidase | bacterial and fungal pathogens |
| pyrrolnitrin synthesis genes | bacterial and fungal pathogens |
| serine/threonine kinases | bacterial and fungal pathogens |
| Cecropin B | bacterial and fungal pathogens rot, leaf mould etc. |
| Phenylalanine ammonia lyase (PAL) | bacterial and fungal pathogens |
| Cf genes eg. Cf 9 Cf5 Cf4 Cf2 | bacterial and fungal pathogens |

TABLE A8-continued

Crop Peppers

| Effected target or expressed principle(s) | Crop phenotype/Tolerance to |
| --- | --- |
| Osmotin | bacterial and fungal pathogens |
| Alpha Hordothionin | bacterial and fungal pathogens |
| Systemin | bacterial and fungal pathogens |
| Polygalacturonase inhibitors | bacterial and fungal pathogens |
| Prf regulatory gene | bacterial and fungal pathogens |
| I2 Fusarium resistance locus | *fusarium* |
| phytoalexins | bacterial and fungal pathogens |
| B-1,3-glucanase antisense | bacterial and fungal pathogens |
| receptor kinase | bacterial and fungal pathogens |
| Hypersensitive response eliciting polypeptide | bacterial and fungal pathogens |
| Systemic acquires resistance (SAR) genes | viral, bacterial, fungal, nematodal pathogens |
| Chitinases | bacterial and fungal pathogens |
| Barnase | bacterial and fungal pathogens |
| Glucanases | bacterial and fungal pathogens |
| double stranded ribonuclease | viruses such as CMV, TEV |
| Coat proteins | viruses such as CMV, TEV |
| 17 kDa or 60 kDa protein | viruses such as CMV, TEV |
| Nuclear inclusion proteins eg. a or b or Nucleoprotein | viruses such as CMV, TEV |
| Pseudoubiquitin | viruses such as CMV, TEV |
| Replicase | viruses such as CMV, TEV |
| *Bacillus thuringiensis* toxins, VIP 3, *Bacillus cereus* toxins, *Photorabdus* and *Xenorhabdus* toxins | lepidoptera, whiteflies aphids |
| 3-Hydroxysteroid oxidase | lepidoptera, whiteflies aphids |
| Peroxidase | lepidoptera, whiteflies aphids |
| Aminopeptidase inhibitors eg. Leucine aminopeptidase inhibitor | lepidoptera, whiteflies aphids |
| Lectines | lepidoptera, whiteflies aphids |
| Protease Inhibitors eg cystatin, patatin | lepidoptera, whiteflies aphids |
| ribosome inactivating protein | lepidoptera, whiteflies aphids |
| stilbene synthase | lepidoptera, whiteflies aphids |
| HMG-CoA reductase | lepidoptera, whiteflies aphids |
| Cyst nematode hatching stimulus | cyst nematodes |
| Barnase | nematodes eg root knot nematodes and cyst nematodes |
| Antifeeding principles | nematodes eg root knot nematodes and cyst nematodes |

TABLE A9

Crop Grapes

| Effected target or expressed principle(s) | Crop phenotype/Tolerance to |
| --- | --- |
| Acetolactate synthase (ALS) | Sulfonylureas, Imidazolinones, Triazolopyrimidines, Pyrimidyloxybenzoates, Phtalides |
| AcetylCoA Carboxylase (ACCase) | Aryloxyphenoxyalkanecarboxylic acids, cyclohexanediones |
| Hydroxyphenylpyruvate dioxygenase (HPPD) | Isoxazoles such as Isoxaflutol or Isoxachlortol, Triones such as mesotrione or sulcotrione |
| Phosphinothricin acetyl transferase | Phosphinothricin |
| O-Methyl transferase | altered lignin levels |
| Glutamine synthetase | Glufosinate, Bialaphos |
| Adenylosuccinate Lyase (ADSL) | Inhibitors of IMP and AMP synthesis |
| Adenylosuccinate Synthase | Inhibitors of adenylosuccinate synthesis |
| Anthranilate Synthase | Inhibitors of tryptophan synthesis and catabolism |
| Nitrilase | 3,5-dihalo-4-hydroxy-benzonitriles such as Bromoxynil and loxinyl |
| 5-Enolpyruvyl-3phosphoshikimate Synthase (EPSPS) | Glyphosate or sulfosate |
| Glyphosate oxidoreductase | Glyphosate or sulfosate |
| Protoporphyrinogen oxidase (PROTOX) | Diphenylethers, cyclic imides, phenylpyrazoles, pyridin derivatives, phenopylate, oxadiazoles etc. |
| Cytochrome P450 eg. P450 SU1 or selection | Xenobiotics and herbicides such as Sulfonylureas |

TABLE A9-continued

Crop Grapes

| Effected target or expressed principle(s) | Crop phenotype/Tolerance to |
|---|---|
| Polyphenol oxidase or Polyphenol oxidase antisense | bacterial and fungal pathogens like *Botrytis* and powdery mildew |
| Metallothionein | bacterial and fungal pathogens like *Botrytis* and powdery mildew |
| Ribonuclease | bacterial and fungal pathogens like *Botrytis* and powdery mildew |
| Antifungal polypeptide AlyAFP | bacterial and fungal pathogens like *Botrytis* and powdery mildew |
| oxalate oxidase | bacterial and fungal pathogens like *Botrytis* and powdery mildew |
| glucose oxidase | bacterial and fungal pathogens like *Botrytis* and powdery mildew |
| pyrrolnitrin synthesis genes | bacterial and fungal pathogens like *Botrytis* and powdery mildew |
| serine/threonine kinases | bacterial and fungal pathogens like *Botrytis* and powdery mildew |
| Cecropin B | bacterial and fungal pathogens like *Botrytis* and powdery mildew |
| Phenylalanine ammonia lyase (PAL) | bacterial and fungal pathogens like *Botrytis* and powdery mildew |
| Cf genes eg. Cf 9 Cf5 Cf4 Cf2 | bacterial and fungal pathogens like *Botrytis* and powdery mildew |
| Osmotin | bacterial and fungal pathogens like *Botrytis* and powdery mildew |
| Alpha Hordothionin | bacterial and fungal pathogens like *Botrytis* and powdery mildew |
| Systemin | bacterial and fungal pathogens like *Botrytis* and powdery mildew |
| Polygalacturonase inhibitors | bacterial and fungal pathogens like *Botrytis* and powdery mildew |
| Prf regulatory gene | bacterial and fungal pathogens like *Botrytis* and powdery mildew |
| phytoalexins | bacterial and fungal pathogens like *Botrytis* and powdery mildew |
| B-1,3-glucanase antisense | bacterial and fungal pathogens like *Botrytis* and powdery mildew |
| receptor kinase | bacterial and fungal pathogens like *Botrytis* and powdery mildew |
| Hypersensitive response eliciting polypeptide | bacterial and fungal pathogens like *Botrytis* and powdery mildew |
| Systemic acquires resistance (SAR) genes | viral, bacterial, fungal, nematodal pathogens |
| Chitinases | bacterial and fungal pathogens like *Botrytis* and powdery mildew |
| Barnase | bacterial and fungal pathogens like *Botrytis* and powdery mildew |
| Glucanases | bacterial and fungal pathogens like *Botrytis* and powdery mildew |
| double stranded ribonuclease | viruses |
| Coat proteins | viruses |
| 17 kDa or 60 kDa protein | viruses |
| Nuclear inclusion proteins eg. a or b or Nucleoprotein | viruses |
| Pseudoubiquitin | viruses |
| Replicase | viruses |
| *Bacillus thuringiensis* toxins, VIP 3, *Bacillus cereus* toxins, *Photorabdus* and *Xenorhabdus* toxins | lepidoptera, aphids |
| 3-Hydroxysteroid oxidase | lepidoptera, aphids |
| Peroxidase | lepidoptera, aphids |
| Aminopeptidase inhibitors eg. Leucine aminopeptidase inhibitor | lepidoptera, aphids |
| Lectines | lepidoptera, aphids |
| Protease Inhibitors eg cystatin, patatin | lepidoptera, aphids |
| ribosome inactivating protein | lepidoptera, aphids |
| stilbene synthase | lepidoptera, aphids, diseases |
| HMG-CoA reductase | lepidoptera, aphids |
| Cyst nematode hatching stimulus | cyst nematodes |
| Barnase | nematodes eg root knot nematodes and cyst nematodes or general diseases |
| CBI | root knot nematodes |
| Antifeeding principles | nematodes eg root knot nematodes or root cyst nematodes |

TABLE A10 crop Oil Seed rape

| Effected target or expressed principle(s) | Crop phenotype/Tolerance to |
|---|---|
| Acetolactate synthase (ALS) | Sulfonylureas, Imidazolinones, Triazolopyrimidines, Pyrimidyloxybenzoates, Phtalides |
| AcetylCoA Carboxylase (ACCase) | Aryloxyphenoxyalkanecarboxylic acids, cyclohexanediones |
| Hydroxyphenylpyruvate dioxygenase (HPPD) | Isoxazoles such as Isoxaflutol or Isoxachlortol, Triones such as mesotrione or sulcotrione |
| Phosphinothricin acetyl transferase | Phosphinothricin |
| O-Methyl transferase | altered lignin levels |
| Glutamine synthetase | Glufosinate, Bialaphos |
| Adenylosuccinate Lyase (ADSL) | Inhibitors of IMP and AMP synthesis |
| Adenylosuccinate Synthase | Inhibitors of adenylosuccinate synthesis |
| Anthranilate Synthase | Inhibitors of tryptophan synthesis and catabolism |
| Nitrilase | 3,5-dihalo-4-hydroxy-benzonitriles such as Bromoxynil and loxinyl |
| 5-Enolpyruvyl-3phosphoshikimate Synthase (EPSPS) | Glyphosate or sulfosate |
| Glyphosate oxidoreductase | Glyphosate or sulfosate |
| Protoporphyrinogen oxidase (PROTOX) | Diphenylethers, cyclic imides, phenylpyrazoles, pyridin derivatives, phenopylate, oxadiazoles etc. |
| Cytochrome P450 eg. P450 SU1 or selection | Xenobiotics and herbicides such as Sulfonylureas |
| Polyphenol oxidase or Polyphenol oxidase antisense | bacterial and fungal pathogens like *Cylindrosporium*, *Phoma*, *Sclerotinia* |
| Metallothionein | bacterial and fungal pathogens like *Cylindrosporium*, *Phoma*, *Sclerotinia* |
| Ribonuclease | bacterial and fungal pathogens like *Cylindrosporium*, *Phoma*, *Sclerotinia* |
| Antifungal polypeptide AlyAFP | bacterial and fungal pathogens like *Cylindrosporium*, *Phoma*, *Sclerotinia* |
| oxalate oxidase | bacterial and fungal pathogens like *Cylindrosporium*, *Phoma*, *Sclerotinia* |
| glucose oxidase | bacterial and fungal pathogens like *Cylindrosporium*, *Phoma*, *Sclerotinia* |
| pyrrolnitrin synthesis genes | bacterial and fungal pathogens like *Cylindrosporium*, *Phoma*, *Sclerotinia* |
| serine/threonine kinases | bacterial and fungal pathogens like *Cylindrosporium*, *Phoma*, *Sclerotinia* |
| Cecropin B | bacterial and fungal pathogens like *Cylindrosporium*, *Phoma*, *Sclerotinia* |
| Phenylalanine ammonia lyase (PAL) | bacterial and fungal pathogens like *Cylindrosporium*, *Phoma*, *Sclerotinia* |
| Cf genes eg. Cf 9 Cf5 Cf4 Cf2 | bacterial and fungal pathogens like *Cylindrosporium*, *Phoma*, *Sclerotinia* |
| Osmotin | bacterial and fungal pathogens like *Cylindrosporium*, *Phoma*, *Sclerotinia* |
| Alpha Hordothionin | bacterial and fungal pathogens like *Cylindrosporium*, *Phoma*, *Sclerotinia* |
| Systemin | bacterial and fungal pathogens like *Cylindrosporium*, *Phoma*, *Sclerotinia* |
| Polygalacturonase inhibitors | bacterial and fungal pathogens like *Cylindrosporium*, *Phoma*, *Sclerotinia* |
| Prf regulatory gene | bacterial and fungal pathogens like *Cylindrosporium*, *Phoma*, *Sclerotinia* |
| phytoalexins | bacterial and fungal pathogens like *Cylindrosporium*, *Phoma*, *Sclerotinia* |
| B-1,3-glucanase antisense | bacterial and fungal pathogens like *Cylindrosporium*, *Phoma*, *Sclerotinia* |
| receptor kinase | bacterial and fungal pathogens like *Cylindrosporium*, *Phoma*, *Sclerotinia* |
| Hypersensitive response eliciting polypeptide | bacterial and fungal pathogens like *Cylindrosporium*, *Phoma*, *Sclerotinia* |
| Systemic acquires resistance (SAR) genes | viral, bacterial, fungal, nematodal pathogens |
| Chitinases | bacterial and fungal pathogens like *Cylindrosporium*, *Phoma*, *Sclerotinia* |
| Barnase | bacterial and fungal pathogens like *Cylindrosporium*, *Phoma*, *Sclerotinia*, nematodes |

TABLE A10-continued crop Oil Seed rape

| Effected target or expressed principle(s) | Crop phenotype/Tolerance to |
| --- | --- |
| Glucanases | bacterial and fungal pathogens like *Cylindrosporium*, *Phoma*, *Sclerotinia* |
| double stranded ribonuclease | viruses |
| Coat proteins | viruses |
| 17 kDa or 60 kDa protein | viruses |
| Nuclear inclusion proteins eg. a or b or Nucleoprotein | viruses |
| Pseudoubiquitin | viruses |
| Replicase | viruses |
| *Bacillus thuringiensis* toxins, VIP 3, *Bacillus cereus* toxins, *Photorabdus* and *Xenorhabdus* toxins | lepidoptera, aphids |
| 3-Hydroxysteroid oxidase | lepidoptera, aphids |
| Peroxidase | lepidoptera, aphids |
| Aminopeptidase inhibitors eg. Leucine aminopeptidase inhibitor | lepidoptera, aphids |
| Lectines | lepidoptera, aphids |
| Protease Inhibitors eg cystatin, patatin, CPTI | lepidoptera, aphids |
| ribosome inactivating protein | lepidoptera, aphids |
| stilbene synthase | lepidoptera, aphids, diseases |
| HMG-CoA reductase | lepidoptera, aphids |
| Cyst nematode hatching stimulus | cyst nematodes |
| Barnase | nematodes eg root knot nematodes and cyst nematodes |
| CBI | root knot nematodes |
| Antifeeding principles induced at a nematode feeding site | nematodes eg root knot nematodes, root cyst nematodes |

TABLE A11

Crop *Brassica* vegetable (cabbage, brussel sprouts, broccoli etc.)

| Effected target or expressed principle(s) | Crop phenotype/Tolerance to |
| --- | --- |
| Acetolactate synthase (ALS) | Sulfonylureas, Imidazolinones, Triazolopyrimidines, Pyrimidyloxybenzoates, Phtalides |
| AcetylCoA Carboxylase (ACCase) | Aryloxyphenoxyalkanecarboxylic acids, cyclohexanediones |
| Hydroxyphenylpyruvate dioxygenase (HPPD) | Isoxazoles such as Isoxaflutol or Isoxachlortol, Triones such as mesotrione or sulcotrione |
| Phosphinothricin acetyl transferase | Phosphinothricin |
| O-Methyl transferase | altered lignin levels |
| Glutamine synthetase | Glufosinate, Bialaphos |
| Adenylosuccinate Lyase (ADSL) | Inhibitors of IMP and AMP synthesis |
| Adenylosuccinate Synthase | Inhibitors of adenylosuccinate synthesis |
| Anthranilate Synthase | Inhibitors of tryptophan synthesis and catabolism |
| Nitrilase | 3,5-dihalo-4-hydroxy-benzonitriles such as Bromoxynil and Ioxinyl |
| 5-Enolpyruvyl-3phosphoshikimate Synthase (EPSPS) | Glyphosate or sulfosate |
| Glyphosate oxidoreductase | Glyphosate or sulfosate |
| Protoporphyrinogen oxidase (PROTOX) | Diphenylethers, cyclic imides, phenylpyrazoles, pyridin derivatives, phenopylate, oxadiazoles etc. |
| Cytochrome P450 eg. P450 SU1 or selection | Xenobiotics and herbicides such as Sulfonylureas |
| Polyphenol oxidase or Polyphenol oxidase antisense | bacterial and fungal pathogens |
| Metallothionein | bacterial and fungal pathogens |
| Ribonuclease | bacterial and fungal pathogens |
| Antifungal polypeptide AlyAFP | bacterial and fungal pathogens |
| oxalate oxidase | bacterial and fungal pathogens |
| glucose oxidase | bacterial and fungal pathogens |
| pyrrolnitrin synthesis genes | bacterial and fungal pathogens |
| serine/threonine kinases | bacterial and fungal pathogens |
| Cecropin B | bacterial and fungal pathogens |
| Phenylalanine ammonia lyase (PAL) | bacterial and fungal pathogens |
| Cf genes eg. Cf 9 Cf5 Cf4 Cf2 | bacterial and fungal pathogens |
| Osmotin | bacterial and fungal pathogens |

TABLE A11-continued

Crop Brassica vegetable (cabbage, brussel sprouts, broccoli etc.)

| Effected target or expressed principle(s) | Crop phenotype/Tolerance to |
|---|---|
| Alpha Hordothionin | bacterial and fungal pathogens |
| Systemin | bacterial and fungal pathogens |
| Polygalacturonase inhibitors | bacterial and fungal pathogens |
| Prf regulatory gene | bacterial and fungal pathogens |
| phytoalexins | bacterial and fungal pathogens |
| B-1,3-glucanase antisense | bacterial and fungal pathogens |
| receptor kinase | bacterial and fungal pathogens |
| Hypersensitive response eliciting polypeptide | bacterial and fungal pathogens |
| Systemic acquires resistance (SAR) genes | viral, bacterial, fungal, nematodal pathogens |
| Chitinases | bacterial and fungal pathogens |
| Barnase | bacterial and fungal pathogens |
| Glucanases | bacterial and fungal pathogens |
| double stranded ribonuclease | viruses |
| Coat proteins | viruses |
| 17 kDa or 60 kDa protein | viruses |
| Nuclear inclusion proteins eg. a or b or Nucleoprotein | viruses |
| Pseudoubiquitin | viruses |
| Replicase | viruses |
| Bacillus thuringiensis toxins, VIP 3, Bacillus cereus toxins, Photorabdus and Xenorhabdus toxins | lepidoptera, aphids |
| 3-Hydroxysteroid oxidase | lepidoptera, aphids |
| Peroxidase | lepidoptera, aphids |
| Aminopeptidase inhibitors eg. Leucine aminopeptidase inhibitor | lepidoptera, aphids |
| Lectines | lepidoptera, aphids |
| Protease Inhibitors eg cystatin, patatin, CPTI | lepidoptera, aphids |
| ribosome inactivating protein | lepidoptera, aphids |
| stilbene synthase | lepidoptera, aphids, diseases |
| HMG-CoA reductase | lepidoptera, aphids |
| Cyst nematode hatching stimulus | cyst nematodes |
| Barnase | nematodes eg root knot nematodes and cyst nematodes |
| CBI | root knot nematodes |
| Antifeeding principles induced at a nematode feeding site | nematodes eg root knot nematodes, root cyst nematodes |

TABLE A12

Crop Pome fruits eg apples, pears

| Effected target or expressed principle(s) | Crop phenotype/Tolerance to |
|---|---|
| Acetolactate synthase (ALS) | Sulfonylureas, Imidazolinones, Triazolopyrimidines, Pyrimidyloxybenzoates, Phtalides |
| AcetylCoA Carboxylase (ACCase) | Aryloxyphenoxyalkanecarboxylic acids, cyclohexanediones |
| Hydroxyphenylpyruvate dioxygenase (HPPD) | Isoxazoles such as Isoxaflutol or Isoxachlortol, Triones such as mesotrione or sulcotrione |
| Phosphinothricin acetyl transferase | Phosphinothricin |
| O-Methyl transferase | altered lignin levels |
| Glutamine synthetase | Glufosinate, Bialaphos |
| Adenylosuccinate Lyase (ADSL) | Inhibitors of IMP and AMP synthesis |
| Adenylosuccinate Synthase | Inhibitors of adenylosuccinate synthesis |
| Anthranilate Synthase | Inhibitors of tryptophan synthesis and catabolism |
| Nitrilase | 3,5-dihalo-4-hydroxy-benzonitriles such as Bromoxynil and loxinyl |
| 5-Enolpyruvyl-3phosphoshikimate Synthase (EPSPS) | Glyphosate or sulfosate |
| Glyphosate oxidoreductase | Glyphosate or sulfosate |
| Protoporphyrinogen oxidase (PROTOX) | Diphenylethers, cyclic imides, phenylpyrazoles, pyridin derivatives, phenopylate, oxadiazoles etc. |
| Cytochrome P450 eg. P450 SU1 or selection | Xenobiotics and herbicides such as Sulfonylureas |

TABLE A12-continued

Crop Pome fruits eg apples, pears

| Effected target or expressed principle(s) | Crop phenotype/Tolerance to |
|---|---|
| Polyphenol oxidase or Polyphenol oxidase antisense | bacterial and fungal pathogens like apple scab or fireblight |
| Metallothionein | bacterial and fungal pathogens like apple scab or fireblight |
| Ribonuclease | bacterial and fungal pathogens like apple scab or fireblight |
| Antifungal polypeptide AlyAFP | bacterial and fungal pathogens like apple scab or fireblight |
| oxalate oxidase | bacterial and fungal pathogens like apple scab or fireblight |
| glucose oxidase | bacterial and fungal pathogens like apple scab or fireblight |
| pyrrolnitrin synthesis genes | bacterial and fungal pathogens like apple scab or fireblight |
| serine/threonine kinases | bacterial and fungal pathogens like apple scab or fireblight |
| Cecropin B | bacterial and fungal pathogens like apple scab or fireblight |
| Phenylalanine ammonia lyase (PAL) | bacterial and fungal pathogens like apple scab or fireblight |
| Cf genes eg. Cf 9 Cf5 Cf4 Cf2 | bacterial and fungal pathogens like apple scab or fireblight |
| Osmotin | bacterial and fungal pathogens like apple scab or fireblight |
| Alpha Hordothionin | bacterial and fungal pathogens like apple scab or fireblight |
| Systemin | bacterial and fungal pathogens like apple scab or fireblight |
| Polygalacturonase inhibitors | bacterial and fungal pathogens like apple scab or fireblight |
| Prf regulatory gene | bacterial and fungal pathogens like apple scab or fireblight |
| phytoalexins | bacterial and fungal pathogens like apple scab or fireblight |
| B-1,3-glucanase antisense | bacterial and fungal pathogens like apple scab or fireblight |
| receptor kinase | bacterial and fungal pathogens like apple scab or fireblight |
| Hypersensitive response eliciting polypeptide | bacterial and fungal pathogens like apple scab or fireblight |
| Systemic acquires resistance (SAR) genes | viral, bacterial, fungal, nematodal pathogens |
| Lytic protein | bacterial and fungal pathogens like apple scab or fireblight |
| Lysozym | bacterial and fungal pathogens like apple scab or fireblight |
| Chitinases | bacterial and fungal pathogens like apple scab or fireblight |
| Barnase | bacterial and fungal pathogens like apple scab or fireblight |
| Glucanases | bacterial and fungal pathogens like apple scab or fireblight |
| double stranded ribonuclease | viruses |
| Coat proteins | viruses |
| 17 kDa or 60 kDa protein | viruses |
| Nuclear inclusion proteins eg. a or b or Nucleoprotein | viruses |
| Pseudoubiquitin | viruses |
| Replicase | viruses |
| *Bacillus thuringiensis* toxins, VIP 3, *Bacillus cereus* toxins, *Photorabdus* and *Xenorhabdus* toxins | lepidoptera, aphids, mites |
| 3-Hydroxysteroid oxidase | lepidoptera, aphids, mites |
| Peroxidase | lepidoptera, aphids, mites |
| Aminopeptidase inhibitors eg. Leucine aminopeptidase inhibitor | lepidoptera, aphids, mites |
| Lectines | lepidoptera, aphids, mites |
| Protease Inhibitors eg cystatin, patatin, CPTI | lepidoptera, aphids, mites |
| ribosome inactivating protein | lepidoptera, aphids, mites |
| stilbene synthase | lepidoptera, aphids, diseases, mites |
| HMG-CoA reductase | lepidoptera, aphids, mites |
| Cyst nematode hatching stimulus | cyst nematodes |
| Barnase | nematodes eg root knot nematodes and cyst nematodes |

TABLE A12-continued

| Crop Pome fruits eg apples, pears | |
|---|---|
| Effected target or expressed principle(s) | Crop phenotype/Tolerance to |
| CBI | root knot nematodes |
| Antifeeding principles induced at a nematode feeding site | nematodes eg root knot nematodes, root cyst nematodes |

TABLE A13

| Crop Melons | |
|---|---|
| Effected target or expressed principle(s) | Crop phenotype/Tolerance to |
| Acetolactate synthase (ALS) | Sulfonylureas, Imidazolinones, Triazolopyrimidines, Pyrimidyloxybenzoates, Phtalides |
| AcetylCoA Carboxylase (ACCase) | Aryloxyphenoxyalkanecarboxylic acids, cyclohexanediones |
| Hydroxyphenylpyruvate dioxygenase (HPPD) | Isoxazoles such as Isoxaflutol or Isoxachlortol, Triones such as mesotrione or sulcotrione |
| Phosphinothricin acetyl transferase | Phosphinothricin |
| O-Methyl transferase | altered lignin levels |
| Glutamine synthetase | Glufosinate, Bialaphos |
| Adenylosuccinate Lyase (ADSL) | Inhibitors of IMP and AMP synthesis |
| Adenylosuccinate Synthase | Inhibitors of adenylosuccinate synthesis |
| Anthranilate Synthase | Inhibitors of tryptophan synthesis and catabolism |
| Nitrilase | 3,5-dihalo-4-hydroxy-benzonitriles such as Bromoxynil and Ioxinyl |
| 5-Enolpyruvyl-3phosphoshikimate Synthase (EPSPS) | Glyphosate or sulfosate |
| Glyphosate oxidoreductase | Glyphosate or sulfosate |
| Protoporphyrinogen oxidase (PROTOX) | Diphenylethers, cyclic imides, phenylpyrazoles, pyridin derivatives, phenopylate, oxadiazoles etc. |
| Cytochrome P450 eg. P450 SU1 or selection | Xenobiotics and herbicides such as Sulfonylureas |
| Polyphenol oxidase or Polyphenol oxidase antisense | bacterial or fungal pathogens like *phytophtora* |
| Metallothionein | bacterial or fungal pathogens like *phytophtora* |
| Ribonuclease | bacterial or fungal pathogens like *phytophtora* |
| Antifungal polypeptide AlyAFP | bacterial or fungal pathogens like *phytophtora* |
| oxalate oxidase | bacterial or fungal pathogens like *phytophtora* |
| glucose oxidase | bacterial or fungal pathogens like *phytophtora* |
| pyrrolnitrin synthesis genes | bacterial or fungal pathogens like *phytophtora* |
| serine/threonine kinases | bacterial or fungal pathogens like *phytophtora* |
| Cecropin B | bacterial or fungal pathogens like *phytophtora* |
| Phenylalanine ammonia lyase (PAL) | bacterial or fungal pathogens like *phytophtora* |
| Cf genes eg. Cf 9 Cf5 Cf4 Cf2 | bacterial or fungal pathogens like *phytophtora* |
| Osmotin | bacterial or fungal pathogens like *phytophtora* |
| Alpha Hordothionin | bacterial or fungal pathogens like *phytophtora* |
| Systemin | bacterial or fungal pathogens like *phytophtora* |
| Polygalacturonase inhibitors | bacterial or fungal pathogens like *phytophtora* |
| Prf regulatory gene | bacterial or fungal pathogens like *phytophtora* |
| phytoalexins | bacterial or fungal pathogens like *phytophtora* |
| B-1,3-glucanase antisense | bacterial or fungal pathogens like *phytophtora* |
| receptor kinase | bacterial or fungal pathogens like *phytophtora* |

TABLE A13-continued

Crop Melons

| Effected target or expressed principle(s) | Crop phenotype/Tolerance to |
| --- | --- |
| Hypersensitive response eliciting polypeptide | bacterial or fungal pathogens like *phytophtora* |
| Systemic acquires resistance (SAR) genes | viral, bacterial, fungal, nematodal pathogens |
| Lytic protein | bacterial or fungal pathogens like *phytophtora* |
| Lysozym | bacterial or fungal pathogens like *phytophtora* |
| Chitinases | bacterial or fungal pathogens like *phytophtora* |
| Barnase | bacterial or fungal pathogens like *phytophtora* |
| Glucanases | bacterial or fungal pathogens like *phytophtora* |
| double stranded ribonuclease | viruses as CMV,, PRSV, WMV2, SMV, ZYMV |
| Coat proteins | viruses as CMV,, PRSV, WMV2, SMV, ZYMV |
| 17 kDa or 60 kDa protein | viruses as CMV,, PRSV, WMV2, SMV, ZYMV |
| Nuclear inclusion proteins eg. a or b or Nucleoprotein | viruses as CMV,, PRSV, WMV2, SMV, ZYMV |
| Pseudoubiquitin | viruses as CMV,, PRSV, WMV2, SMV, ZYMV |
| Replicase | viruses as CMV,, PRSV, WMV2, SMV, ZYMV |
| *Bacillus thuringiensis* toxins, VIP 3, *Bacillus cereus* toxins, *Photorabdus* and *Xenorhabdus* toxins | lepidoptera, aphids, mites |
| 3-Hydroxysteroid oxidase | lepidoptera, aphids, mites, whitefly |
| Peroxidase | lepidoptera, aphids, mites, whitefly |
| Aminopeptidase inhibitors eg. Leucine aminopeptidase inhibitor | lepidoptera, aphids, mites, whitefly |
| Lectines | lepidoptera, aphids, mites, whitefly |
| Protease Inhibitors eg cystatin, patatin, CPTI, virgiferin | lepidoptera, aphids, mites, whitefly |
| ribosome inactivating protein | lepidoptera, aphids, mites, whitefly |
| stilbene synthase | lepidoptera, aphids, mites, whitefly |
| HMG-CoA reductase | lepidoptera, aphids, mites, whitefly |
| Cyst nematode hatching stimulus | cyst nematodes |
| Barnase | nematodes eg root knot nematodes and cyst nematodes |
| CBI | root knot nematodes |
| Antifeeding principles induced at a nematode feeding site | nematodes eg root knot nematodes, root cyst nematodes |

TABLE A 14

Crop Banana

| Effected target or expressed principle(s) | Crop phenotype/Tolerance to |
| --- | --- |
| Acetolactate synthase (ALS) | Sulfonylureas, Imidazolinones, Triazolopyrimidines, Pyrimidyloxybenzoates, Phtalides |
| AcetylCoA Carboxylase (ACCase) | Aryloxyphenoxyalkanecarboxylic acids, cyclohexanediones |
| Hydroxyphenylpyruvate dioxygenase (HPPD) | Isoxazoles such as Isoxaflutol or Isoxachlortol, Triones such as mesotrione or sulcotrione |
| Phosphinothricin acetyl transferase | Phosphinothricin |
| O-Methyl transferase | altered lignin levels |
| Glutamine synthetase | Glufosinate, Bialaphos |
| Adenylosuccinate Lyase (ADSL) | Inhibitors of IMP and AMP synthesis |
| Adenylosuccinate Synthase | Inhibitors of adenylosuccinate synthesis |
| Anthranilate Synthase | Inhibitors of tryptophan synthesis and catabolism |
| Nitrilase | 3,5-dihalo-4-hydroxy-benzonitriles such as Bromoxynil and loxinyl |
| 5-Enolpyruvyl-3phosphoshikimate Synthase (EPSPS) | Glyphosate or sulfosate |
| Glyphosate oxidoreductase | Glyphosate or sulfosate |

TABLE A 14-continued

Crop Banana

| Effected target or expressed principle(s) | Crop phenotype/Tolerance to |
|---|---|
| Protoporphyrinogen oxidase (PROTOX) | Diphenylethers, cyclic imides, phenylpyrazoles, pyridin derivatives, phenopylate, oxadiazoles etc. |
| Cytochrome P450 eg. P450 SU1 or selection | Xenobiotics and herbicides such as Sulfonylureas |
| Polyphenol oxidase or Polyphenol oxidase antisense | bacterial or fungal pathogens |
| Metallothionein | bacterial or fungal pathogens |
| Ribonuclease | bacterial or fungal pathogens |
| Antifungal polypeptide AlyAFP | bacterial or fungal pathogens |
| oxalate oxidase | bacterial or fungal pathogens |
| glucose oxidase | bacterial or fungal pathogens |
| pyrrolnitrin synthesis genes | bacterial or fungal pathogens |
| serine/threonine kinases | bacterial or fungal pathogens |
| Cecropin B | bacterial or fungal pathogens |
| Phenylalanine ammonia lyase (PAL) | bacterial or fungal pathogens |
| Cf genes eg. Cf 9 Cf5 Cf4 Cf2 | bacterial or fungal pathogens |
| Osmotin | bacterial or fungal pathogens |
| Alpha Hordothionin | bacterial or fungal pathogens |
| Systemin | bacterial or fungal pathogens |
| Polygalacturonase inhibitors | bacterial or fungal pathogens |
| Prf regulatory gene | bacterial or fungal pathogens |
| phytoalexins | bacterial or fungal pathogens |
| B-1,3-glucanase antisense | bacterial or fungal pathogens |
| receptor kinase | bacterial or fungal pathogens |
| Hypersensitive response eliciting polypeptide | bacterial or fungal pathogens |
| Systemic acquires resistance (SAR) genes | viral, bacterial, fungal, nematodal pathogens |
| Lytic protein | bacterial or fungal pathogens |
| Lysozym | bacterial or fungal pathogens |
| Chitinases | bacterial or fungal pathogens |
| Barnase | bacterial or fungal pathogens |
| Glucanases | bacterial or fungal pathogens |
| double stranded ribonuclease | viruses as Banana bunchy top virus (BBTV) |
| Coat proteins | viruses as Banana bunchy top virus (BBTV) |
| 17 kDa or 60 kDa protein | viruses as Banana bunchy top virus (BBTV) |
| Nuclear inclusion proteins eg. a or b or Nucleoprotein | viruses as Banana bunchy top virus (BBTV) |
| Pseudoubiquitin | viruses as Banana bunchy top virus (BBTV) |
| Replicase | viruses as Banana bunchy top virus (BBTV) |
| *Bacillus thuringiensis* toxins, VIP 3, *Bacillus cereus* toxins, *Photorabdus* and *Xenorhabdus* toxins | lepidoptera, aphids, mites, nematodes |
| 3-Hydroxysteroid oxidase | lepidoptera, aphids, mites, nematodes |
| Peroxidase | lepidoptera, aphids, mites, nematodes |
| Aminopeptidase inhibitors eg. Leucine aminopeptidase inhibitor | lepidoptera, aphids, mites, nematodes |
| Lectines | lepidoptera, aphids, mites, nematodes |
| Protease Inhibitors eg cystatin, patatin, CPTI, virgiferin | lepidoptera, aphids, mites, nematodes |
| ribosome inactivating protein | lepidoptera, aphids, mites, nematodes |
| stilbene synthase | lepidoptera, aphids, mites, nematodes |
| HMG-CoA reductase | lepidoptera, aphids, mites, nematodes |
| Cyst nematode hatching stimulus | cyst nematodes |
| Barnase | nematodes eg root knot nematodes and cyst nematodes |
| CBI | root knot nematodes |
| Antifeeding principles induced at a nematode feeding site | nematodes eg root knot nematodes, root cyst nematodes |

TABLE A 15

| Crop Cotton | |
|---|---|
| Effected target or expressed principle(s) | Crop phenotype/Tolerance to |
| Acetolactate synthase (ALS) | Sulfonylureas, Imidazolinones, Triazolopyrimidines, Pyrimidyloxybenzoates, Phtalides |
| AcetylCoA Carboxylase (ACCase) | Aryloxyphenoxyalkanecarboxylic acids, cyclohexanediones |
| Hydroxyphenylpyruvate dioxygenase (HPPD) | Isoxazoles such as Isoxaflutol or Isoxachlortol, Triones such as mesotrione or sulcotrione |
| Phosphinothricin acetyl transferase | Phosphinothricin |
| O-Methyl transferase | altered lignin levels |
| Glutamine synthetase | Glufosinate, Bialaphos |
| Adenylosuccinate Lyase (ADSL) | Inhibitors of IMP and AMP synthesis |
| Adenylosuccinate Synthase | Inhibitors of adenylosuccinate synthesis |
| Anthranilate Synthase | Inhibitors of tryptophan synthesis and catabolism |
| Nitrilase | 3,5-dihalo-4-hydroxy-benzonitriles such as Bromoxynil and Ioxinyl |
| 5-Enolpyruvyl-3phosphoshikimate Synthase (EPSPS) | Glyphosate or sulfosate |
| Glyphosate oxidoreductase | Glyphosate or sulfosate |
| Protoporphyrinogen oxidase (PROTOX) | Diphenylethers, cyclic imides, phenylpyrazoles, pyridin derivatives, phenopylate, oxadiazoles etc. |
| Cytochrome P450 eg. P450 SU1 or selection | Xenobiotics and herbicides such as Sulfonylureas |
| Polyphenol oxidase or Polyphenol oxidase antisense | bacterial or fungal pathogens |
| Metallothionein | bacterial or fungal pathogens |
| Ribonuclease | bacterial or fungal pathogens |
| Antifungal polypeptide AlyAFP | bacterial or fungal pathogens |
| oxalate oxidase | bacterial or fungal pathogens |
| glucose oxidase | bacterial or fungal pathogens |
| pyrrolnitrin synthesis genes | bacterial or fungal pathogens |
| serine/threonine kinases | bacterial or fungal pathogens |
| Cecropin B | bacterial or fungal pathogens |
| Phenylalanine ammonia lyase (PAL) | bacterial or fungal pathogens |
| Cf genes eg. Cf 9 Cf5 Cf4 Cf2 | bacterial or fungal pathogens |
| Osmotin | bacterial or fungal pathogens |
| Alpha Hordothionin | bacterial or fungal pathogens |
| Systemin | bacterial or fungal pathogens |
| Polygalacturonase inhibitors | bacterial or fungal pathogens |
| Prf regulatory gene | bacterial or fungal pathogens |
| phytoalexins | bacterial or fungal pathogens |
| B-1,3-glucanase antisense | bacterial or fungal pathogens |
| receptor kinase | bacterial or fungal pathogens |
| Hypersensitive response eliciting polypeptide | bacterial or fungal pathogens |
| Systemic acquires resistance (SAR) genes | viral, bacterial, fungal, nematodal pathogens |
| Lytic protein | bacterial or fungal pathogens |
| Lysozym | bacterial or fungal pathogens |
| Chitinases | bacterial or fungal pathogens |
| Barnase | bacterial or fungal pathogens |
| Glucanases | bacterial or fungal pathogens |
| double stranded ribonuclease | viruses as wound tumor virus (WTV) |
| Coat proteins | viruses as wound tumor virus (WTV) |
| 17 kDa or 60 kDa protein | viruses as wound tumor virus (WTV) |
| Nuclear inclusion proteins eg. a or b or Nucleoprotein | viruses as wound tumor virus (WTV) |
| Pseudoubiquitin | viruses as wound tumor virus (WTV) |
| Replicase | viruses as wound tumor virus (WTV) |
| *Bacillus thuringiensis* toxins, VIP 3, *Bacillus cereus* toxins, *Photorabdus* and *Xenorhabdus* toxins | lepidoptera, aphids, mites, nematodes, whitefly |
| 3-Hydroxysteroid oxidase | lepidoptera, aphids, mites, nematodes, whitefly |
| Peroxidase | lepidoptera, aphids, mites, nematodes, whitefly |
| Aminopeptidase inhibitors eg. Leucine aminopeptidase inhibitor | lepidoptera, aphids, mites, nematodes, whitefly |
| Lectines | lepidoptera, aphids, mites, nematodes, whitefly |
| Protease Inhibitors eg cystatin, patatin, CPTI, virgiferin | lepidoptera, aphids, mites, nematodes, whitefly |
| ribosome inactivating protein | lepidoptera, aphids, mites, nematodes, whitefly |

TABLE A 15-continued

Crop Cotton

| Effected target or expressed principle(s) | Crop phenotype/Tolerance to |
| --- | --- |
| stilbene synthase | lepidoptera, aphids, mites, nematodes, whitefly |
| HMG-CoA reductase | lepidoptera, aphids, mites, nematodes, whitefly |
| Cyst nematode hatching stimulus | cyst nematodes |
| Barnase | nematodes eg root knot nematodes and cyst nematodes |
| CBI | root knot nematodes |
| Antifeeding principles induced at a nematode feeding site | nematodes eg root knot nematodes, root cyst nematodes |

TABLE A 16

Crop Sugarcane

| Effected target or expressed principle(s) | Crop phenotype/Tolerance to |
| --- | --- |
| Acetolactate synthase (ALS) | Sulfonylureas, Imidazolinones, Triazolopyrimidines, Pyrimidyloxybenzoates, Phtalides |
| AcetylCoA Carboxylase (ACCase) | Aryloxyphenoxyalkanecarboxylic acids, cyclohexanediones |
| Hydroxyphenylpyruvate dioxygenase (HPPD) | Isoxazoles such as Isoxaflutol or Isoxachlortol, Triones such as mesotrione or sulcotrione |
| Phosphinothricin acetyl transferase | Phosphinothricin |
| O-Methyl transferase | altered lignin levels |
| Glutamine synthetase | Glufosinate, Bialaphos |
| Adenylosuccinate Lyase (ADSL) | Inhibitors of IMP and AMP synthesis |
| Adenylosuccinate Synthase | Inhibitors of adenylosuccinate synthesis |
| Anthranilate Synthase | Inhibitors of tryptophan synthesis and catabolism |
| Nitrilase | 3,5-dihalo-4-hydroxy-benzonitriles such as Bromoxynil and loxinyl |
| 5-Enolpyruvyl-3phosphoshikimate Synthase (EPSPS) | Glyphosate or sulfosate |
| Glyphosate oxidoreductase | Glyphosate or sulfosate |
| Protoporphyrinogen oxidase (PROTOX) | Diphenylethers, cyclic imides, phenylpyrazoles, pyridin derivatives, phenopylate, oxadiazoles etc. |
| Cytochrome P450 eg. P450 SU1 or selection | Xenobiotics and herbicides such as Sulfonylureas |
| Polyphenol oxidase or Polyphenol oxidase antisense | bacterial or fungal pathogens |
| Metallothionein | bacterial or fungal pathogens |
| Ribonuclease | bacterial or fungal pathogens |
| Antifungal polypeptide AlyAFP | bacterial or fungal pathogens |
| oxalate oxidase | bacterial or fungal pathogens |
| glucose oxidase | bacterial or fungal pathogens |
| pyrrolnitrin synthesis genes | bacterial or fungal pathogens |
| serine/threonine kinases | bacterial or fungal pathogens |
| Cecropin B | bacterial or fungal pathogens |
| Phenylalanine ammonia lyase (PAL) | bacterial or fungal pathogens |
| Cf genes eg. Cf 9 Cf5 Cf4 Cf2 | bacterial or fungal pathogens |
| Osmotin | bacterial or fungal pathogens |
| Alpha Hordothionin | bacterial or fungal pathogens |
| Systemin | bacterial or fungal pathogens |
| Polygalacturonase inhibitors | bacterial or fungal pathogens |
| Prf regulatory gene | bacterial or fungal pathogens |
| phytoalexins | bacterial or fungal pathogens |
| B-1,3-glucanase antisense | bacterial or fungal pathogens |
| receptor kinase | bacterial or fungal pathogens |
| Hypersensitive response eliciting polypeptide | bacterial or fungal pathogens |
| Systemic acquires resistance (SAR) genes | viral, bacterial, fungal, nematodal pathogens |
| Lytic protein | bacterial or fungal pathogens |
| Lysozym | bacterial or fungal pathogens eg clavibacter |
| Chitinases | bacterial or fungal pathogens |
| Barnase | bacterial or fungal pathogens |
| Glucanases | bacterial or fungal pathogens |
| double stranded ribonuclease | viruses as SCMV, SrMV |

TABLE A 16-continued

Crop Sugarcane

| Effected target or expressed principle(s) | Crop phenotype/Tolerance to |
| --- | --- |
| Coat proteins | viruses as SCMV, SrMV |
| 17 kDa or 60 kDa protein | viruses as SCMV, SrMV |
| Nuclear inclusion proteins eg. a or b or Nucleoprotein | viruses as SCMV, SrMV |
| Pseudoubiquitin | viruses as SCMV, SrMV |
| Replicase | viruses as SCMV, SrMV |
| *Bacillus thuringiensis* toxins, VIP 3, *Bacillus cereus* toxins, *Photorabdus* and *Xenorhabdus* toxins | lepidoptera, aphids, mites, nematodes, whitefly, beetles eg mexican rice borer |
| 3-Hydroxysteroid oxidase | lepidoptera, aphids, mites, nematodes, whitefly, beetles eg mexican rice borer |
| Peroxidase | lepidoptera, aphids, mites, nematodes, whitefly, beetles eg mexican rice borer |
| Aminopeptidase inhibitors eg. Leucine aminopeptidase inhibitor | lepidoptera, aphids, mites, nematodes, whitefly, beetles eg mexican rice borer |
| Lectines | lepidoptera, aphids, mites, nematodes, whitefly, beetles eg mexican rice borer |
| Protease Inhibitors eg cystatin, patatin, CPTI, virgiferin | lepidoptera, aphids, mites, nematodes, whitefly, beetles eg mexican rice borer |
| ribosome inactivating protein | lepidoptera, aphids, mites, nematodes, whitefly, beetles eg mexican rice borer |
| stilbene synthase | lepidoptera, aphids, mites, nematodes, whitefly, beetles eg mexican rice borer |
| HMG-CoA reductase | lepidoptera, aphids, mites, nematodes, whitefly, beetles eg mexican rice borer |
| Cyst nematode hatching stimulus | cyst nematodes |
| Barnase | nematodes eg root knot nematodes and cyst nematodes |
| CBI | root knot nematodes |
| Antifeeding principles induced at a nematode feeding site | nematodes eg root knot nematodes, root cyst nematodes |

TABLE A 17

Crop Sunflower

| Effected target or expressed principle(s) | Crop phenotype/Tolerance to |
| --- | --- |
| Acetolactate synthase (ALS) | Sulfonylureas, Imidazolinones, Triazolopyrimidines, Pyrimidyloxybenzoates, Phtalides |
| AcetylCoA Carboxylase (ACCase) | Aryloxyphenoxyalkanecarboxylic acids, cyclohexanediones |
| Hydroxyphenylpyruvate dioxygenase (HPPD) | Isoxazoles such as Isoxaflutol or Isoxachlortol, Triones such as mesotrione or sulcotrione |
| Phosphinothricin acetyl transferase | Phosphinothricin |
| O-Methyl transferase | altered lignin levels |
| Glutamine synthetase | Glufosinate, Bialaphos |
| Adenylosuccinate Lyase (ADSL) | Inhibitors of IMP and AMP synthesis |
| Adenylosuccinate Synthase | Inhibitors of adenylosuccinate synthesis |
| Anthranilate Synthase | Inhibitors of tryptophan synthesis and catabolism |
| Nitrilase | 3,5-dihalo-4-hydroxy-benzonitriles such as Bromoxynil and loxinyl |
| 5-Enolpyruvyl-3phosphoshikimate Synthase (EPSPS) | Glyphosate or sulfosate |
| Glyphosate oxidoreductase | Glyphosate or sulfosate |
| Protoporphyrinogen oxidase (PROTOX) | Diphenylethers, cyclic imides, phenylpyrazoles, pyridin derivatives, phenopylate, oxadiazoles etc. |
| Cytochrome P450 eg. P450 SU1 or selection | Xenobiotics and herbicides such as Sulfonylureas |
| Polyphenol oxidase or Polyphenol oxidase antisense | bacterial or fungal pathogens |
| Metallothionein | bacterial or fungal pathogens |
| Ribonuclease | bacterial or fungal pathogens |
| Antifungal polypeptide AlyAFP | bacterial or fungal pathogens |
| oxalate oxidase | bacterial or fungal pathogens eg *sclerotinia* |
| glucose oxidase | bacterial or fungal pathogens |
| pyrrolnitrin synthesis genes | bacterial or fungal pathogens |
| serine/threonine kinases | bacterial or fungal pathogens |
| Cecropin B | bacterial or fungal pathogens |

TABLE A 17-continued

Crop Sunflower

| Effected target or expressed principle(s) | Crop phenotype/Tolerance to |
| --- | --- |
| Phenylalanine ammonia lyase (PAL) | bacterial or fungal pathogens |
| Cf genes eg. Cf 9 Cf5 Cf4 Cf2 | bacterial or fungal pathogens |
| Osmotin | bacterial or fungal pathogens |
| Alpha Hordothionin | bacterial or fungal pathogens |
| Systemin | bacterial or fungal pathogens |
| Polygalacturonase inhibitors | bacterial or fungal pathogens |
| Prf regulatory gene | bacterial or fungal pathogens |
| phytoalexins | bacterial or fungal pathogens |
| B-1,3-glucanase antisense | bacterial or fungal pathogens |
| receptor kinase | bacterial or fungal pathogens |
| Hypersensitive response eliciting polypeptide | bacterial or fungal pathogens |
| Systemic acquires resistance (SAR) genes | viral, bacterial, fungal, nematodal pathogens |
| Lytic protein | bacterial or fungal pathogens |
| Lysozym | bacterial or fungal pathogens |
| Chitinases | bacterial or fungal pathogens |
| Barnase | bacterial or fungal pathogens |
| Glucanases | bacterial or fungal pathogens |
| double stranded ribonuclease | viruses as CMV, TMV |
| Coat proteins | viruses as CMV, TMV |
| 17 kDa or 60 kDa protein | viruses as CMV, TMV |
| Nuclear inclusion proteins eg. a or b or Nucleoprotein | viruses as CMV, TMV |
| Pseudoubiquitin | viruses as CMV, TMV |
| Replicase | viruses as CMV, TMV |
| *Bacillus thuringiensis* toxins, VIP 3, *Bacillus cereus* toxins, *Photorabdus* and *Xenorhabdus* toxins | lepidoptera, aphids, mites, nematodes, whitefly, beetles |
| 3-Hydroxysteroid oxidase | lepidoptera, aphids, mites, nematodes, whitefly, beetles |
| Peroxidase | lepidoptera, aphids, mites, nematodes, whitefly, beetles |
| Aminopeptidase inhibitors eg. Leucine aminopeptidase inhibitor | lepidoptera, aphids, mites, nematodes, whitefly, beetles |
| Lectines | lepidoptera, aphids, mites, nematodes, whitefly, beetles |
| Protease Inhibitors eg cystatin, patatin, CPTI, virgiferin | lepidoptera, aphids, mites, nematodes, whitefly, beetles |
| ribosome inactivating protein | lepidoptera, aphids, mites, nematodes, whitefly, beetles |
| stilbene synthase | lepidoptera, aphids, mites, nematodes, whitefly, beetles |
| HMG-CoA reductase | lepidoptera, aphids, mites, nematodes, whitefly, beetles |
| Cyst nematode hatching stimulus | cyst nematodes |
| Barnase | nematodes eg root knot nematodes and cyst nematodes |
| CBI | root knot nematodes |
| Antifeeding principles induced at a nematode feeding site | nematodes eg root knot nematodes, root cyst nematodes |

TABLE A 18

Crop Sugarbeet, Beet root

| Effected target or expressed principle(s) | Crop phenotype/Tolerance to |
| --- | --- |
| Acetolactate synthase (ALS) | Sulfonylureas, Imidazolinones, Triazolopyrimidines, Pyrimidyloxybenzoates, Phtalides |
| AcetylCoA Carboxylase (ACCase) | Aryloxyphenoxyalkanecarboxylic acids, cyclohexanediones |
| Hydroxyphenylpyruvate dioxygenase (HPPD) | Isoxazoles such as Isoxaflutol or Isoxachlortol, Triones such as mesotrione or sulcotrione |
| Phosphinothricin acetyl transferase | Phosphinothricin |
| O-Methyl transferase | altered lignin levels |
| Glutamine synthetase | Glufosinate, Bialaphos |
| Adenylosuccinate Lyase (ADSL) | Inhibitors of IMP and AMP synthesis |
| Adenylosuccinate Synthase | Inhibitors of adenylosuccinate synthesis |
| Anthranilate Synthase | Inhibitors of tryptophan synthesis and catabolism |

TABLE A 18-continued

Crop Sugarbeet, Beet root

| Effected target or expressed principle(s) | Crop phenotype/Tolerance to |
|---|---|
| Nitrilase | 3,5-dihalo-4-hydroxy-benzonitriles such as Bromoxynil and Ioxinyl |
| 5-Enolpyruvyl-3phosphoshikimate Synthase (EPSPS) | Glyphosate or sulfosate |
| Glyphosate oxidoreductase | Glyphosate or sulfosate |
| Protoporphyrinogen oxidase (PROTOX) | Diphenylethers, cyclic imides, phenylpyrazoles, pyridin derivatives, phenopylate, oxadiazoles etc. |
| Cytochrome P450 eg. P450 SU1 or selection | Xenobiotics and herbicides such as Sulfonylureas |
| Polyphenol oxidase or Polyphenol oxidase antisense | bacterial or fungal pathogens |
| Metallothionein | bacterial or fungal pathogens |
| Ribonuclease | bacterial or fungal pathogens |
| Antifungal polypeptide AlyAFP | bacterial or fungal pathogens |
| oxalate oxidase | bacterial or fungal pathogens eg *sclerotinia* |
| glucose oxidase | bacterial or fungal pathogens |
| pyrrolnitrin synthesis genes | bacterial or fungal pathogens |
| serine/threonine kinases | bacterial or fungal pathogens |
| Cecropin B | bacterial or fungal pathogens |
| Phenylalanine ammonia lyase (PAL) | bacterial or fungal pathogens |
| Cf genes eg. Cf 9 Cf5 Cf4 Cf2 | bacterial or fungal pathogens |
| Osmotin | bacterial or fungal pathogens |
| Alpha Hordothionin | bacterial or fungal pathogens |
| Systemin | bacterial or fungal pathogens |
| Polygalacturonase inhibitors | bacterial or fungal pathogens |
| Prf regulatory gene | bacterial or fungal pathogens |
| phytoalexins | bacterial or fungal pathogens |
| B-1,3-glucanase antisense | bacterial or fungal pathogens |
| AX + WIN proteins | bacterial or fungal pathogens like *Cercospora beticola* |
| receptor kinase | bacterial or fungal pathogens |
| Hypersensitive response eliciting polypeptide | bacterial or fungal pathogens |
| Systemic acquires resistance (SAR) genes | viral, bacterial, fungal, nematodal pathogens |
| Lytic protein | bacterial or fungal pathogens |
| Lysozym | bacterial or fungal pathogens |
| Chitinases | bacterial or fungal pathogens |
| Barnase | bacterial or fungal pathogens |
| Glucanases | bacterial or fungal pathogens |
| double stranded ribonuclease | viruses as BNYVV |
| Coat proteins | viruses as BNYVV |
| 17 kDa or 60 kDa protein | viruses as BNYVV |
| Nuclear inclusion proteins eg. a or b or Nucleoprotein | viruses as BNYVV |
| Pseudoubiquitin | viruses as BNYVV |
| Replicase | viruses as BNYVV |
| *Bacillus thuringiensis* toxins, VIP 3, *Bacillus cereus* toxins, *Photorabdus* and *Xenorhabdus* toxins | lepidoptera, aphids, mites, nematodes, whitefly, beetles, rootflies |
| 3-Hydroxysteroid oxidase | lepidoptera, aphids, mites, nematodes, whitefly, beetles, rootflies |
| Peroxidase | lepidoptera, aphids, mites, nematodes, whitefly, beetles, rootflies |
| Aminopeptidase inhibitors eg. Leucine aminopeptidase inhibitor | lepidoptera, aphids, mites, nematodes, whitefly, beetles, rootflies |
| Lectines | lepidoptera, aphids, mites, nematodes, whitefly, beetles, rootflies |
| Protease Inhibitors eg cystatin, patatin, CPTI, virgiferin | lepidoptera, aphids, mites, nematodes, whitefly, beetles, rootflies |
| ribosome inactivating protein | lepidoptera, aphids, mites, nematodes, whitefly, beetles, rootflies |
| stilbene synthase | lepidoptera, aphids, mites, nematodes, whitefly, beetles, rootflies |
| HMG-CoA reductase | lepidoptera, aphids, mites, nematodes, whitefly, beetles, rootflies |
| Cyst nematode hatching stimulus | cyst nematodes |
| Barnase | nematodes eg root knot nematodes and cyst nematodes |
| Beet cyst nematode resistance locus | cyst nematodes |
| CBI | root knot nematodes |
| Antifeeding principles induced at a nematode feeding site | nematodes eg root knot nematodes, root cyst nematodes |

The abovementioned animal pests which can be controlled by the method according to the invention include, for example, insects, representatives of the order acarina and representatives of the class nematoda; especially from the order Lepidoptera *Acleris* spp., *Adoxophyes* spp., especially *Adoxophyes reticulana; Aegeria* spp., *Agrotis* spp., especially *Agrotis spinifera; Alabama argillaceae, Amylois* spp., *Anticarsia gemmatalis, Archips* spp., *Argyrotaenia* spp., *Autographa* spp., *Busseola fusca, Cadra cautella, Carposina nipponensis, Chilo* spp., *Choristoneura* spp., *Clysia ambiguella, Cnaphalocrocis* spp., *Cnephasia* spp., *Cochylis* spp., *Coleophora* spp., *Crocidolomia binotalis, Cryptophlebia leucotreta, Cydia* spp., especially *Cydia pomonella; Diatraea* spp., *Diparopsis castanea, Earias* spp., *Ephestia* spp., especially E. Khüniella; *Eucosma* spp., *Eupoecilia ambiguella, Euproctis* spp., *Euxoa* spp., *Grapholita* spp., *Hedya nubiferana, Heliothis* spp., especially *H. Virescens* und *H. zea; Hellula undalis, Hyphantria cunea, Keiferia lycopersicella, Leucoptera scitella, Lithocollethis* spp., *Lobesia* spp., *Lymantria* spp., *Lyonetia* spp., *Malacosoma* spp., *Mamestra brassicae, Manduca sexta, Operophtera* spp., *Ostrinia nubilalis, Pammene* spp., *Pandemis* spp., *Panolis flammea, Pectinophora* spp., *Phthorimaea operculella, Pieris rapae, Pieris* spp., *Plutella xylostella, Prays* spp., *Scirpophaga* spp., *Sesamia* spp., *Sparganothis* spp., Spodopteralittoralis, *Synanthedon* spp., *Thaumetopoea* spp., *Tortrix* spp., *Trichoplusia ni* and *Yponomeuta* spp.;

from the order Coleoptera, for example *Agriotes* spp., *Anthonomus* spp., *Atomaria linearis, Chaetocnema tibialis, Cosmopolites* spp., *Curculio* spp., *Dermestes* spp., *Diabrotica* spp., *Epilachna* spp., *Eremnus* spp., *Leptinotarsa decemlineata, Lissorhoptrus* spp., *Melolontha* spp., *Oryzaephilus* spp., *Otiorhynchus* spp., *Phlyctinus* spp., *Popillia* spp., *Psylliodes* spp., *Rhizopertha* spp., *Scarabeidae, Sitophilus* spp., *Sitotroga* spp., *Tenebrio* spp., *Tribolium* spp. and *Trogoderma* spp.;

from the order Orthoptera, for example *Blatta* spp., *Blattella* spp., *Gryllotalpa* spp., *Leucophaea maderae, Locusta* spp., *Periplaneta* spp. and *Schistocerca* spp.;

from the order Isoptera, for example *Reticulitermes* spp.;

from the order Psocoptera, for example *Liposcelis* spp.;

from the order Anoplura, for example *Haematopinus* spp., *Linognathus* spp., *Pediculus* spp., *Pemphigus* spp. and *Phylloxera* spp.;

from the order Mallophaga, for example *Damalinea* spp. and *Trichodectes* spp.;

from the order Thysanoptera, for example *Frankliniella* spp., *Hercinothrips* spp., *Taeniothrips* spp., *Thrips palmi, Thrips tabaci* and *Scirtothrips aurantii*;

from the order Heteroptera, for example *Cimex* spp., *Distantiella theobroma, Dysdercus* spp., *Euchistus* spp. *Eurygaster* spp. *Leptocorisa* spp., *Nezara* spp., *Piesma* spp., *Rhodnius* spp., *Sahlbergella singularis, Scotinophara* spp. and *Triatoma* spp.;

from the order Homoptera, for example *Aleurothrixus floccosus, Aleyrodes brassicae, Aonidiella aurantii, Aphididae, Aphis craccivora, A. fabae, A. gosypii; Aspidiotus* spp., *Bemisia tabaci, Ceroplaster* spp., *Chrysomphalus aonidium, Chrysomphalus dictyospermi, Coccus hesperidum, Empoasca* spp., *Eriosoma lanigerum, Erythroneura* spp., *Gascardia* spp., *Laodelphax* spp., *Lecanium corni, Lepidosaphes* spp., *Macrosiphus* spp., *Myzus* spp., especially *M. persicae; Nephotettix* spp., especially *N. cincticeps; Nilaparvata* spp., especially *N. lugens; Paratoria* spp., *Pemphigus* spp., *Planococcus* spp., *Pseudaulacaspis* spp., *Pseudococcus* spp., especially *P. Fragilis, P. citriculus* and *P. comstocki; Psylla* spp., especially *P. pyri; Pulvinaria aethiopica, Quadraspidiotus* spp., *Rhopalosiphum* spp., *Saissetia* spp., *Scaphoideus* spp., *Schizaphis* spp., *Sitobion* spp., *Trialeurodes vaporariorum, Trioza erytreae* and *Unaspis citri;* from the order Hymenoptera, for example *Acromyrmex, Atta* spp., *Cephus* spp., *Diprion* spp., *Diprionidae, Gilpinia polytoma, Hoplocampa* spp., *Lasius* spp., *Monomorium pharaonis, Neodiprion* spp., *Solenopsis* spp. and *Vespa* spp.;

from the order Diptera, for example *Aedes* spp., *Antherigona soccata, Bibio hortulanus, Calliphora erythrocephala, Ceratitis* spp., *Chrysomyia* spp., *Culex* spp., *Cuterebra* spp., *Dacus* spp., *Drosophila melanogaster, Fannia* spp., *Gastrophilus* spp., *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit, Pegomyia hyoscyami, Phorbia* spp., *Rhagoletis pomonella, Sciara* spp., *Stomoxys* spp., *Tabanus* spp., *Tannia* spp. and *Tipula* spp.;

from the order Siphonaptera, for example *Ceratophyllus* spp. and *Xenopsylla cheopis;* from the order Thysanura, for example *Lepisma saccharina* and from the order Acarina, for example *Acarus siro, Aceria sheldoni; Aculus* spp., especially *A. schlechtendali; Amblyomma* spp., *Argas* spp., *Boophilus* spp., *Brevipalpus* spp., especially *B. californicus* and *B. phoenicis; Bryobia praetiosa, Calipitrimerus* spp., *Chorioptes* spp., *Dermanyssus gallinae, Eotetranychus* spp., especially *E. carpini* and *E. orientalis; Eriophyes* spp., especially *E. vitis; Hyalomma* spp., *Ixodes* spp., *Olygonychus pratensis, Ornithodoros* spp., *Panonychus* spp., especially *P. ulmi* and *P. citri; Phyllocoptruta* spp., especially *P. oleivora; Polyphagotarsonemus* spp., especially *P. latus; Psoroptes* spp., *Rhipicephalus* spp., *Rhizoglyphus* spp., *Sarcoptes* spp., *Tarsonemus* spp. and *Tetranychus* spp., in particular *T. urticae, T. cinnabarinus* and *T. Kanzawai;* representatives of the class Nematoda;

(1) nematodes selected from the group consisting of root knot nematodes, cyst-forming nematodes, stem eelworms and foliar nematodes;

(2) nematodes selected from the group consisting of *Anguina* spp.; *Aphelenchoides* spp.; *Ditylenchus* spp.; *Globodera* spp., for example *Globodera rostochiensis; Heterodera* spp., for example *Heterodera avenae, Heterodera glycines, Heterodera schachtii* or *Heterodera trifolii; Longidorus* spp.; *Meloidogyne* spp., for example *Meloidogyne incognita* or *Meloidogyne javanica; Pratylenchus,* for example *Pratylenchus neglectans* or *Pratylenchus penetrans; Radopholus* spp., for example Radopholus similis; *Trichodorus* spp.; *Tylenchulus,* for example *Tylenchulus semipenetrans*; and *Xiphinema* spp.; or (3) nematodes selected from the group consisting of *Heterodera* spp., for example *Heterodera glycines*; and *Meloidogyne* spp., for example *Meloidogyne incognita*.

The method according to the invention allows pests of the abovementioned type to be controlled, i.e. contained or destroyed, which occur, in particular, on transgenic plants, mainly useful plants and ornamentals in agriculture, in horticulture and in forests, or on parts, such as fruits, flowers, foliage, stalks, tubers or roots, of such plants, the protection against these pests in some cases even extending to plant parts which form at a later point in time.

The method according to the invention can be employed advantageously for controlling pests in rice, cereals such as maize or sorghum; in fruit, for example stone fruit, pome fruit and soft fruit such as apples, pears, plums, peaches, almonds, cherries or berries, for example strawberries, raspberries and blackberries; in legumes such as beans, lentils, peas or soya beans; in oil crops such as oilseed rape, mustard, poppies, olives, sunflowers, coconuts, castor-oil plants, cacao or peanuts; in the marrow family such as pumpkins, cucumbers or melons; in fibre plants such as cotton, flax, hemp or jute; in citrus fruit such as oranges, lemons, grapefruit or tangerines; in vegetables such as spinach, lettuce, asparagus, cabbage species, carrots, onions, tomatoes, potatoes, beet or capsicum; in the laurel family such as avocado, Cinnamonium or camphor; or in tobacco, nuts, coffee, egg plants, sugar cane, tea, pepper, grapevines, hops, the banana family, latex plants or ornamentals, mainly in maize, rice, cereals, soya beans, tomatoes, cotton, potatoes, sugar beet, rice and mustard; in particular in cotton, rice, soya beans, potatoes and maize.

It has emerged that the method according to the invention is valuable preventatively and/or curatively in the field of pest control even at low use concentrations of the pesticidal composition and that a very favourable biocidal spectrum is achieved thereby. Combined with a favourable compatibility of the composition employed with warm-blooded species, fish and plants, the method according to the invention can be employed against all or individual developmental stages of normally-sensitive, but also of normally-resistant, animal pests such as insects and representatives of the order Acarina, depending on the species of the transgenic crop plant to be protected from attack by pests. The insecticidal and/or acaricidal effect of the method according to the invention may become apparent directly, i.e. in a destruction of the pests which occurs immediately or only after some time has elapsed, for example, during ecdysis, or indirectly, for example as a reduced oviposition and/or hatching rate, the good action corresponding to a destruction rate (mortality) of at least 40 to 50%.

Depending on the intended aims and the prevailing circumstances, the pesticides within the scope of invention, which are known per se, are emulsifiable concentrates, suspension concentrates, directly sprayable or dilutable solutions, spreadable pastes, dilute emulsions, wettable powders, soluble powders, dispersible powders, wettable powders, dusts, granules or encapsulations in polymeric substances which comprise a nitroimino- or nitroguanidino-compound.

The active ingredients are employed in these compositions together with at least one of the auxiliaries conventionally used in art of formulation, such as extenders, for example solvents or solid carriers, or such as surface-active compounds (surfactants).

Formulation auxiliaries which are used are, for example, solid carriers, solvents, stabilizers, "slow release" auxiliaries, colourants and, if appropriate, surface-active substances (surfactants). Suitable carriers and auxiliaries are all those substances which are conventionally used for crop protection products. Suitable auxiliaries such as solvents, solid carriers, surface-active compounds, non-ionic surfactants, cationic surfactants, anionic surfactants and other auxiliaries in the compositions employed according to the invention are, for example, those which have been described in EP-A-736 252.

These compositions for controlling pests can be formulated, for example, as wettable powders, dusts, granules, solutions, emulsifiable concentrates, emulsions, suspension concentrates or aerosols. For example, the compositions are of the type described in EP-A-736 252.

The action of the compositions within the scope of invention which comprise a nitroimino- or nitroguanidino-compound can be extended substantially and adapted to prevailing circumstances by adding other insecticidally, acaricidally and/or fungicidally active ingredients. Suitable examples of added active ingredients are representatives of the following classes of active ingredients: organophosphorous compounds, nitrophenols and derivatives, formamidines, ureas, carbamates, pyrethroids, chlorinated hydrocarbons; especially preferred components in mixtures are, for example, abamectin, emamectin, spinosad, pymetrozine, fenoxycarb, Ti-435, fipronil, pyriproxyfen, diazinon or diafenthiuron.

As a rule, the compositions within the scope of invention comprise 0.1 to 99%, in particular 0.1 to 95%, of a nitroimino- or nitroguanidino-compound and 1 to 99.9%, in particular 5 to 99.9%, of—at least—one solid or liquid auxiliary, it being possible, as a rule, for 0 to 25%, in particular 0.1 to 20%, of the compositions to be surfactants (% in each case meaning percent by weight). While concentrated compositions are more preferred as commercial products, the end user will, as a rule, use dilute compositions which have considerably lower concentrations of active ingredient.

The compositions according to the invention may also comprise other solid or liquid auxiliaries, such as stabilisers, for example epoxidized or unepoxidized vegetable oils (for example epoxidized coconut oil, rapeseed oil or soya bean oil), antifoams, for example silicone oil, preservatives, viscosity regulators, binders and/or tackifiers, and also fertilizers or other active ingredients for achieving specific effects, for example, bactericides, fungicides, nematicides, molluscicides or herbicides.

The compositions according to the invention are produced in a known manner, for example prior to mixing with the auxiliary/auxiliaries by grinding, screening and/or compressing the active ingredient, for example to give a particular particle size, and by intimately mixing and/or grinding the active ingredient with the auxiliary/auxiliaries.

The method according to the invention for controlling pests of the abovementioned type is carried out in a manner known per se to those skilled in the art, depending on the intended aims and prevailing circumstances, that is to say by spraying, wetting, atomizing, dusting, brushing on, seed dressing, scattering or pouring of the composition. Typical use concentrations are between 0.1 and 1000 ppm, preferably between 0.1 and 500 ppm of active ingredient. The application rate may vary within wide ranges and depends on the soil constitution, the type of application (foliar application; seed dressing; application in the seed furrow), the transgenic crop plant, the pest to be controlled, the climatic circumstances prevailing in each case, and other factors determined by the type of application, timing of application and target crop. The application rates per hectare are generally 1 to 2000 g of nitroimino- or nitroguanidino-compound per hectare, in particular 10 to 1000 g/ha, preferably 10 to 500 g/ha, especially preferably 10 to 200 g/ha.

A preferred type of application in the field of crop protection within the scope of invention is application to the foliage of the plants (foliar application), it being possible to adapt frequency and rate of application to the risk of infestation with the pest in question. However, the active ingredient may also enter into the plants via the root system (systemic action), by drenching the site of the plants with a liquid composition or by incorporating the active ingredient in solid form into the site of the plants, for example into the soil, for example in the form of granules (soil application). In the case of paddy rice crops, such granules may be metered into the flooded paddy field.

The compositions according to invention are also suitable for protecting propagation material of transgenic plants, for example seed, such as fruits, tubers or kernels, or plant cuttings, from animal pests, in particular insects and representatives of the order Acarina. The propagation material can be treated with the composition prior to application, for example, seed being dressed prior to sowing. The active ingredient may also be applied to seed kernels (coating), either by soaking the kernels in a liquid composition or by coating them with a solid composition. The composition may also be applied to the site of application when applying the propagation material, for example into the seed furrow during sowing. These treatment methods for plant propagation material and the plant propagation material treated thus are a further subject of the invention.

Examples of formulations of nitroimino- or nitroguanidino-compounds which can be used in the method according to the invention, for instance solutions, granules, dusts, sprayable powders, emulsion concentrates, coated granules and suspension concentrates, are of the type as has been described in, for example, EP-A-580 553, Examples F1 to F10.

BIOLOGICAL EXAMPLES

TABLE B

| | AP | Control of |
|---|---|---|
| B.1 | CryIA(a) | *Adoxophyes* spp. |
| B.2 | CryIA(a) | *Agrotis* spp. |
| B.3 | CryIA(a) | *Alabama argillaceae* |
| B.4 | CryIA(a) | *Anticarsia gemmatalis* |
| B.5 | CryIA(a) | *Chilo* spp. |
| B.6 | CryIA(a) | *Clysia ambiguella* |
| B.7 | CryIA(a) | *Crocidolomia binotalis* |
| B.8 | CryIA(a) | *Cydia* spp. |
| B.9 | CryIA(a) | *Diparopsis castanea* |
| B.10 | CryIA(a) | *Earias* spp. |
| B.11 | CryIA(a) | *Ephestia* spp. |
| B.12 | CryIA(a) | *Heliothis* spp. |
| B.13 | CryIA(a) | *Hellula undalis* |
| B.14 | CryIA(a) | *Keiferia lycopersicella* |
| B.15 | CryIA(a) | *Leucoptera scitella* |
| B.16 | CryIA(a) | *Lithocollethis* spp. |
| B.17 | CryIA(a) | *Lobesia botrana* |
| B.18 | CryIA(a) | *Ostrinia nubilalis* |
| B.19 | CryIA(a) | *Pandemis* spp. |
| B.20 | CryIA(a) | *Pectinophora gossyp.* |
| B.21 | CryIA(a) | *Phyllocnistis citrella* |
| B.22 | CryIA(a) | *Pieris* spp. |
| B.23 | CryIA(a) | *Plutella xylostella* |
| B.24 | CryIA(a) | *Scirpophaga* spp. |
| B.25 | CryIA(a) | *Sesamia* spp. |
| B.26 | CryIA(a) | *Sparganothis* spp. |
| B.27 | CryIA(a) | *Spodoptera* spp. |
| B.28 | CryIA(a) | *Tortrix* spp. |
| B.29 | CryIA(a) | *Trichoplusia ni* |
| B.30 | CryIA(a) | *Agriotes* spp. |
| B.31 | CryIA(a) | *Anthonomus grandis* |
| B.32 | CryIA(a) | *Curculio* spp. |
| B.33 | CryIA(a) | *Diabrotica balteata* |
| B.34 | CryIA(a) | *Leptinotarsa* spp. |
| B.35 | CryIA(a) | *Lissorhoptrus* spp. |
| B.36 | CryIA(a) | *Otiorhynchus* spp. |
| B.37 | CryIA(a) | *Aleurothrixus* spp. |
| B.38 | CryIA(a) | *Aleyrodes* spp. |
| B.39 | CryIA(a) | *Aonidiella* spp. |
| B.40 | CryIA(a) | *Aphididae* spp. |
| B.41 | CryIA(a) | *Aphis* spp. |
| B.42 | CryIA(a) | *Bemisia tabaci* |
| B.43 | CryIA(a) | *Empoasca* spp. |
| B.44 | CryIA(a) | *Mycus* spp. |
| B.45 | CryIA(a) | *Nephotettix* spp. |

TABLE B-continued

| | AP | Control of |
|---|---|---|
| B.46 | CryIA(a) | *Nilaparvata* spp. |
| B.47 | CryIA(a) | *Pseudococcus* spp. |
| B.48 | CryIA(a) | *Psylla* spp. |
| B.49 | CryIA(a) | *Quadraspidiotus* spp. |
| B.50 | CryIA(a) | *Schizaphis* spp. |
| B.51 | CryIA(a) | *Trialeurodes* spp. |
| B.52 | CryIA(a) | *Lyriomyza* spp. |
| B.53 | CryIA(a) | *Oscinella* spp. |
| B.54 | CryIA(a) | *Phorbia* spp. |
| B.55 | CryIA(a) | *Frankliniella* spp. |
| B.56 | CryIA(a) | *Thrips* spp. |
| B.57 | CryIA(a) | *Scirtothrips aurantii* |
| B.58 | CryIA(a) | *Aceria* spp. |
| B.59 | CryIA(a) | *Aculus* spp. |
| B.60 | CryIA(a) | *Brevipalpus* spp. |
| B.61 | CryIA(a) | *Panonychus* spp. |
| B.62 | CryIA(a) | *Phyllocoptruta* spp. |
| B.63 | CryIA(a) | *Tetranychus* spp. |
| B.64 | CryIA(a) | *Heterodera* spp. |
| B.65 | CryIA(a) | *Meloidogyne* spp. |
| B.66 | CryIA(b) | *Adoxophyes* spp. |
| B.67 | CryIA(b) | *Agrotis* spp. |
| B.68 | CryIA(b) | *Alabama argillaceae* |
| B.69 | CryIA(b) | *Anticarsia gemmatalis* |
| B.70 | CryIA(b) | *Chilo* spp. |
| B.71 | CryIA(b) | *Clysia ambiguella* |
| B.72 | CryIA(b) | *Crocidolomia binotalis* |
| B.73 | CryIA(b) | *Cydia* spp. |
| B.74 | CryIA(b) | *Diparopsis castanea* |
| B.75 | CryIA(b) | *Earias* spp. |
| B.76 | CryIA(b) | *Ephestia* spp. |
| B.77 | CryIA(b) | *Heliothis* spp. |
| B.78 | CryIA(b) | *Hellula undalis* |
| B.79 | CryIA(b) | *Keiferia lycopersicella* |
| B.80 | CryIA(b) | *Leucoptera scitella* |
| B.81 | CryIA(b) | *Lithocollethis* spp. |
| B.82 | CryIA(b) | *Lobesia botrana* |
| B.83 | CryIA(b) | *Ostrinia nubilalis* |
| B.84 | CryIA(b) | *Pandemis* spp. |
| B.85 | CryIA(b) | *Pectinophora gossyp.* |
| B.86 | CryIA(b) | *Phyllocnistis citrella* |
| B.87 | CryIA(b) | *Pieris* spp. |
| B.88 | CryIA(b) | *Plutella xylostella* |
| B.89 | CryIA(b) | *Scirpophaga* spp. |
| B.90 | CryIA(b) | *Sesamia* spp. |
| B.91 | CryIA(b) | *Sparganothis* spp. |
| B.92 | CryIA(b) | *Spodoptera* spp. |
| B.93 | CryIA(b) | *Tortrix* spp. |
| B.94 | CryIA(b) | *Trichoplusia ni* |
| B.95 | CryIA(b) | *Agriotes* spp. |
| B.96 | CryIA(b) | *Anthonomus grandis* |
| B.97 | CryIA(b) | *Curculio* spp. |
| B.98 | CryIA(b) | *Diabrotica balteata* |
| B.99 | CryIA(b) | *Leptinotarsa* spp. |
| B.100 | CryIA(b) | *Lissorhoptrus* spp. |
| B.101 | CryIA(b) | *Otiorhynchus* spp. |
| B.102 | CryIA(b) | *Aleurothrixus* spp. |
| B.103 | CryIA(b) | *Aleyrodes* spp. |
| B.104 | CryIA(b) | *Aonidiella* spp. |
| B.105 | CryIA(b) | *Aphididae* spp. |
| B.106 | CryIA(b) | *Aphis* spp. |
| B.107 | CryIA(b) | *Bemisia tabaci* |
| B.108 | CryIA(b) | *Empoasca* spp. |
| B.109 | CryIA(b) | *Mycus* spp. |
| B.110 | CryIA(b) | *Nephotettix* spp. |
| B.111 | CryIA(b) | *Nilaparvata* spp. |
| B.112 | CryIA(b) | *Pseudococcus* spp. |
| B.113 | CryIA(b) | *Psylla* spp. |
| B.114 | CryIA(b) | *Quadraspidiotus* spp. |

TABLE B-continued

| | AP | Control of |
|---|---|---|
| B.115 | CryIA(b) | *Schizaphis* spp. |
| B.116 | CryIA(b) | *Trialeurodes* spp. |
| B.117 | CryIA(b) | *Lyriomyza* spp. |
| B.118 | CryIA(b) | *Oscinella* spp. |
| B.119 | CryIA(b) | *Phorbia* spp. |
| B.120 | CryIA(b) | *Frankliniella* spp. |
| B.121 | CryIA(b) | *Thrips* spp. |
| B.122 | CryIA(b) | *Scirtothrips aurantii* |
| B.123 | CryIA(b) | *Aceria* spp. |
| B.124 | CryIA(b) | *Aculus* spp. |
| B.125 | CryIA(b) | *Brevipalpus* spp. |
| B.126 | CryIA(b) | *Panonychus* spp. |
| B.127 | CryIA(b) | *Phyllocoptruta* spp. |
| B.128 | CryIA(b) | *Tetranychus* spp. |
| B.129 | CryIA(b) | *Heterodera* spp. |
| B.130 | CryIA(b) | *Meloidogyne* spp. |
| B.131 | CryIA(c) | *Adoxophyes* spp. |
| B.132 | CryIA(c) | *Agrotis* spp. |
| B.133 | CryIA(c) | *Alabama argillaceae* |
| B.134 | CryIA(c) | *Anticarsia gemmatalis* |
| B.135 | CryIA(c) | *Chilo* spp. |
| B.136 | CryIA(c) | *Clysia ambiguella* |
| B.137 | CryIA(c) | *Crocidolomia binotalis* |
| B.138 | CryIA(c) | *Cydia* spp. |
| B.139 | CryIA(c) | *Diparopsis castanea* |
| B.140 | CryIA(c) | *Earias* spp. |
| B.141 | CryIA(c) | *Ephestia* spp. |
| B.142 | CryIA(c) | *Heliothis* spp. |
| B.143 | CryIA(c) | *Hellula undalis* |
| B.144 | CryIA(c) | *Keiferia lycopersicella* |
| B.145 | CryIA(c) | *Leucoptera scitella* |
| B.146 | CryIA(c) | *Lithocollethis* spp. |
| B.147 | CryIA(c) | *Lobesia botrana* |
| B.148 | CryIA(c) | *Ostrinia nubilalis* |
| B.149 | CryIA(c) | *Pandemis* spp. |
| B.150 | CryIA(c) | *Pectinophora gossypiella*. |
| B.151 | CryIA(c) | *Phyllocnistis citrella* |
| B.152 | CryIA(c) | *Pieris* spp. |
| B.153 | CryIA(c) | *Plutella xylostella* |
| B.154 | CryIA(c) | *Scirpophaga* spp. |
| B.155 | CryIA(c) | *Sesamia* spp. |
| B.156 | CryIA(c) | *Sparganothis* spp. |
| B.157 | CryIA(c) | *Spodoptera* spp. |
| B.158 | CryIA(c) | *Tortrix* spp. |
| B.159 | CryIA(c) | *Trichoplusia ni* |
| B.160 | CryIA(c) | *Agriotes* spp. |
| B.161 | CryIA(c) | *Anthonomus grandis* |
| B.162 | CryIA(c) | *Curculio* spp. |
| B.163 | CryIA(c) | *Diabrotica balteata* |
| B.164 | CryIA(c) | *Leptinotarsa* spp. |
| B.165 | CryIA(c) | *Lissorhoptrus* spp. |
| B.166 | CryIA(c) | *Otiorhynchus* spp. |
| B.167 | CryIA(c) | *Aleurothrixus* spp. |
| B.168 | CryIA(c) | *Aleyrodes* spp. |
| B.169 | CryIA(c) | *Aonidiella* spp. |
| B.170 | CryIA(c) | *Aphididae* spp. |
| B.171 | CryIA(c) | *Aphis* spp. |
| B.172 | CryIA(c) | *Bemisia tabaci* |
| B.173 | CryIA(c) | *Empoasca* spp. |
| B.174 | CryIA(c) | *Mycus* spp. |
| B.175 | CryIA(c) | *Nephotettix* spp. |
| B.176 | CryIA(c) | *Nilaparvata* spp. |
| B.177 | CryIA(c) | *Pseudococcus* spp. |
| B.178 | CryIA(c) | *Psylla* spp. |
| B.179 | CryIA(c) | *Quadraspidiotus* spp. |
| B.180 | CryIA(c) | *Schizaphis* spp. |
| B.181 | CryIA(c) | *Trialeurodes* spp. |
| B.182 | CryIA(c) | *Lyriomyza* spp. |
| B.183 | CryIA(c) | *Oscinella* spp. |
| B.184 | CryIA(c) | *Phorbia* spp. |
| B.185 | CryIA(c) | *Frankliniella* spp. |
| B.186 | CryIA(c) | *Thrips* spp. |
| B.187 | CryIA(c) | *Scirtothrips aurantii* |
| B.188 | CryIA(c) | *Aceria* spp. |
| B.189 | CryIA(c) | *Aculus* spp. |
| B.190 | CryIA(c) | *Brevipalpus* spp. |
| B.191 | CryIA(c) | *Panonychus* spp. |
| B.192 | CryIA(c) | *Phyllocoptruta* spp. |
| B.193 | CryIA(c) | *Tetranychus* spp. |
| B.194 | CryIA(c) | *Heterodera* spp. |
| B.195 | CryIA(c) | *Meloidogyne* spp. |
| B.196 | CryIIA | *Adoxophyes* spp. |
| B.197 | CryIIA | *Agrotis* spp. |
| B.198 | CryIIA | *Alabama argillaceae* |
| B.199 | | *Anticarsia gemmatalis* |
| B.200 | CryIIA | *Chilo* spp. |
| B.201 | CryIIA | *Clysia ambiguella* |
| B.202 | CryIIA | *Crocidolomia binotalis* |
| B.203 | CryIIA | *Cydia* spp. |
| B.204 | CryIIA | *Diparopsis castanea* |
| B.205 | CryIIA | *Earias* spp. |
| B.206 | CryIIA | *Ephestia* spp. |
| B.207 | CryIIA | *Heliothis* spp. |
| B.208 | CryIIA | *Hellula undalis* |
| B.209 | CryIIA | *Keiferia lycopersicella* |
| B.210 | CryIIA | *Leucoptera scitella* |
| B.211 | CryIIA | *Lithocollethis* spp. |
| B.212 | CryIIA | *Lobesia botrana* |
| B.213 | CryIIA | *Ostrinia nubilalis* |
| B.214 | CryIIA | *Pandemis* spp. |
| B.215 | CryIIA | *Pectinophora gossyp*. |
| B.216 | CryIIA | *Phyllocnistis citrella* |
| B.217 | CryIIA | *Pieris* spp. |
| B.218 | CryIIA | *Plutella xylostella* |
| B.219 | CryIIA | *Scirpophaga* spp. |
| B.220 | CryIIA | *Sesamia* spp. |
| B.221 | CryIIA | *Sparganothis* spp. |
| B.222 | CryIIA | *Spodoptera* spp. |
| B.223 | CryIIA | *Tortrix* spp. |
| B.224 | CryIIA | *Trichoplusia ni* |
| B.225 | CryIIA | *Agriotes* spp. |
| B.226 | CryIIA | *Anthonomus grandis* |
| B.227 | CryIIA | *Curculio* spp. |
| B.228 | CryIIA | *Diabrotica balteata* |
| B.229 | CryIIA | *Leptinotarsa* spp. |
| B.230 | CryIIA | *Lissorhoptrus* spp. |
| B.231 | CryIIA | *Otiorhynchus* spp. |
| B.232 | CryIIA | *Aleurothrixus* spp. |
| B.233 | CryIIA | *Aleyrodes* spp. |
| B.234 | CryIIA | *Aonidiella* spp. |
| B.235 | CryIIA | *Aphididae* spp. |
| B.236 | CryIIA | *Aphis* spp. |
| B.237 | CryIIA | *Bemisia tabaci* |
| B.238 | CryIIA | *Empoasca* spp. |
| B.239 | CryIIA | *Mycus* spp. |
| B.240 | CryIIA | *Nephotettix* spp. |
| B.241 | CryIIA | *Nilaparvata* spp. |
| B.242 | CryIIA | *Pseudococcus* spp. |
| B.243 | CryIIA | *Psylla* spp. |
| B.244 | CryIIA | *Quadraspidiotus* spp. |
| B.245 | CryIIA | *Schizaphis* spp. |
| B.246 | CryIIA | *Trialeurodes* spp. |
| B.247 | CryIIA | *Lyriomyza* spp. |
| B.248 | CryIIA | *Oscinella* spp. |
| B.249 | CryIIA | *Phorbia* spp. |
| B.250 | CryIIA | *Frankliniella* spp. |
| B.251 | CryIIA | *Thrips* spp. |
| B.252 | CryIIA | *Scirtothrips aurantii* |
| B.253 | CryIIA | *Aceria* spp. |
| B.254 | CryIIA | *Aculus* spp. |

TABLE B-continued

| | AP | Control of |
|---|---|---|
| B.255 | CryIIA | *Brevipalpus* spp. |
| B.256 | CryIIA | *Panonychus* spp. |
| B.257 | CryIIA | *Phyllocoptruta* spp. |
| B.258 | CryIIA | *Tetranychus* spp. |
| B.259 | CryIIA | *Heterodera* spp. |
| B.260 | CryIIA | *Meloidogyne* spp. |
| B.261 | CryIIIA | *Adoxophyes* spp. |
| B.262 | CryIIIA | *Agrotis* spp. |
| B.263 | CryIIIA | *Alabama argillaceae* |
| B.264 | CryIIIA | *Anticarsia gemmatalis* |
| B.265 | CryIIIA | *Chilo* spp. |
| B.266 | CryIIIA | *Clysia ambiguella* |
| B.267 | CryIIIA | *Crocidolomia binotalis* |
| B.268 | CryIIIA | *Cydia* spp. |
| B.269 | CryIIIA | *Diparopsis castanea* |
| B.270 | CryIIIA | *Earias* spp. |
| B.271 | CryIIIA | *Ephestia* spp. |
| B.272 | CryIIIA | *Heliothis* spp. |
| B.273 | CryIIIA | *Hellula undalis* |
| B.274 | CryIIIA | *Keiferia lycopersicella* |
| B.275 | CryIIIA | *Leucoptera scitella* |
| B.276 | CryIIIA | *Lithocollethis* spp. |
| B.277 | CryIIIA | *Lobesia botrana* |
| B.278 | CryIIIA | *Ostrinia nubilalis* |
| B.279 | CryIIIA | *Pandemis* spp. |
| B.280 | CryIIIA | *Pectinophora gossyp.* |
| B.281 | CryIIIA | *Phyllocnistis citrella* |
| B.282 | CryIIIA | *Pieris* spp. |
| B.283 | CryIIIA | *Plutella xylostella* |
| B.284 | CryIIIA | *Scirpophaga* spp. |
| B.285 | CryIIIA | *Sesamia* spp. |
| B.286 | CryIIIA | *Sparganothis* spp. |
| B.287 | CryIIIA | *Spodoptera* spp. |
| B.288 | CryIIIA | *Tortrix* spp. |
| B.289 | CryIIIA | *Trichoplusia ni* |
| B.290 | CryIIIA | *Agriotes* spp. |
| B.291 | CryIIIA | *Anthonomus grandis* |
| B.292 | CryIIIA | *Curculio* spp. |
| B.293 | CryIIIA | *Diabrotica balteata* |
| B.294 | CryIIIA | *Leptinotarsa* spp. |
| B.295 | CryIIIA | *Lissorhoptrus* spp. |
| B.296 | CryIIIA | *Otiorhynchus* spp. |
| B.297 | CryIIIA | *Aleurothrixus* spp. |
| B.298 | CryIIIA | *Aleyrodes* spp. |
| B.299 | CryIIIA | *Aonidiella* spp. |
| B.300 | CryIIIA | *Aphididae* spp. |
| B.301 | CryIIIA | *Aphis* spp. |
| B.302 | CryIIIA | *Bemisia tabaci* |
| B.303 | CryIIIA | *Empoasca* spp. |
| B.304 | CryIIIA | *Mycus* spp. |
| B.305 | CryIIIA | *Nephotettix* spp. |
| B.306 | CryIIIA | *Nilaparvata* spp. |
| B.307 | CryIIIA | *Pseudococcus* spp. |
| B.308 | CryIIIA | *Psylla* spp. |
| B.309 | CryIIIA | *Quadraspidiotus* spp. |
| B.310 | CryIIIA | *Schizaphis* spp. |
| B.311 | CryIIIA | *Trialeurodes* spp. |
| B.312 | CryIIIA | *Lyriomyza* spp. |
| B.313 | CryIIIA | *Oscinella* spp. |
| B.314 | CryIIIA | *Phorbia* spp. |
| B.315 | CryIIIA | *Frankliniella* spp. |
| B.316 | CryIIIA | *Thrips* spp. |
| B.317 | CryIIIA | *Scirtothrips aurantii* |
| B.318 | CryIIIA | *Aceria* spp. |
| B.319 | CryIIIA | *Aculus* spp. |
| B.320 | CryIIIA | *Brevipalpus* spp. |
| B.321 | CryIIIA | *Panonychus* spp. |
| B.322 | CryIIIA | *Phyllocoptruta* spp. |
| B.323 | CryIIIA | *Tetranychus* spp. |
| B.324 | CryIIIA | *Heterodera* spp. |
| B.325 | CryIIIA | *Meloidogyne* spp. |
| B.326 | CryIIIB2 | *Adoxophyes* spp. |
| B.327 | CryIIIB2 | *Agrotis* spp. |
| B.328 | CryIIIB2 | *Alabama argillaceae* |
| B.329 | CryIIIB2 | *Anticarsia gemmatalis* |
| B.330 | CryIIIB2 | *Chilo* spp. |
| B.331 | CryIIIB2 | *Clysia ambiguella* |
| B.332 | CryIIIB2 | *Crocidolomia binotalis* |
| B.333 | CryIIIB2 | *Cydia* spp. |
| B.334 | CryIIIB2 | *Diparopsis castanea* |
| B.335 | CryIIIB2 | *Earias* spp. |
| B.336 | CryIIIB2 | *Ephestia* spp. |
| B.337 | CryIIIB2 | *Heliothis* spp. |
| B.338 | CryIIIB2 | *Hellula undalis* |
| B.339 | CryIIIB2 | *Keiferia lycopersicella* |
| B.340 | CryIIIB2 | *Leucoptera scitella* |
| B.341 | CryIIIB2 | *Lithocollethis* spp. |
| B.342 | CryIIIB2 | *Lobesia botrana* |
| B.343 | CryIIIB2 | *Ostrinia nubilalis* |
| B.344 | CryIIIB2 | *Pandemis* spp. |
| B.345 | CryIIIB2 | *Pectinophora gossyp.* |
| B.346 | CryIIIB2 | *Phyllocnistis citrella* |
| B.347 | CryIIIB2 | *Pieris* spp. |
| B.348 | CryIIIB2 | *Plutella xylostella* |
| B.349 | CryIIIB2 | *Scirpophaga* spp. |
| B.350 | CryIIIB2 | *Sesamia* spp. |
| B.351 | CryIIIB2 | *Sparganothis* spp. |
| B.352 | CryIIIB2 | *Spodoptera* spp. |
| B.353 | CryIIIB2 | *Tortrix* spp. |
| B.354 | CryIIIB2 | *Trichoplusia ni* |
| B.355 | CryIIIB2 | *Agriotes* spp. |
| B.356 | CryIIIB2 | *Anthonomus grandis* |
| B.357 | CryIIIB2 | *Curculio* spp. |
| B.358 | CryIIIB2 | *Diabrotica balteata* |
| B.359 | CryIIIB2 | *Leptinotarsa* spp. |
| B.360 | CryIIIB2 | *Lissorhoptrus* spp. |
| B.361 | CryIIIB2 | *Otiorhynchus* spp. |
| B.362 | CryIIIB2 | *Aleurothrixus* spp. |
| B.363 | CryIIIB2 | *Aleyrodes* spp. |
| B.364 | CryIIIB2 | *Aonidiella* spp. |
| B.365 | CryIIIB2 | *Aphididae* spp. |
| B.366 | CryIIIB2 | *Aphis* spp. |
| B.367 | CryIIIB2 | *Bemisia tabaci* |
| B.368 | CryIIIB2 | *Empoasca* spp. |
| B.369 | CryIIIB2 | *Mycus* spp. |
| B.370 | CryIIIB2 | *Nephotettix* spp. |
| B.371 | CryIIIB2 | *Nilaparvata* spp. |
| B.372 | CryIIIB2 | *Pseudococcus* spp. |
| B.373 | CryIIIB2 | *Psylla* spp. |
| B.374 | CryIIIB2 | *Quadraspidiotus* spp. |
| B.375 | CryIIIB2 | *Schizaphis* spp. |
| B.376 | CryIIIB2 | *Trialeurodes* spp. |
| B.377 | CryIIIB2 | *Lyriomyza* spp. |
| B.378 | CryIIIB2 | *Oscinella* spp. |
| B.379 | CryIIIB2 | *Phorbia* spp. |
| B.380 | CryIIIB2 | *Frankliniella* spp. |
| B.381 | CryIIIB2 | *Thrips* spp. |
| B.382 | CryIIIB2 | *Scirtothrips aurantii* |
| B.383 | CryIIIB2 | *Aceria* spp. |
| B.384 | CryIIIB2 | *Aculus* spp. |
| B.385 | CryIIIB2 | *Brevipalpus* spp. |
| B.386 | CryIIIB2 | *Panonychus* spp. |
| B.387 | CryIIIB2 | *Phyllocoptruta* spp. |
| B.388 | CryIIIB2 | *Tetranychus* spp. |
| B.389 | CryIIIB2 | *Heterodera* spp. |
| B.390 | CryIIIB2 | *Meloidogyne* spp. |
| B.391 | CytA | *Adoxophyes* spp. |
| B.392 | CytA | *Agrotis* spp. |
| B.393 | CytA | *Alabama argillaceae* |

TABLE B-continued

| | AP | Control of |
|---|---|---|
| B.394 | CytA | *Anticarsia gemmatalis* |
| B.395 | CytA | *Chilo* spp. |
| B.396 | CytA | *Clysia ambiguella* |
| B.397 | CytA | *Crocidolomia binotalis* |
| B.398 | CytA | *Cydia* spp. |
| B.399 | CytA | *Diparopsis castanea* |
| B.400 | CytA | *Earias* spp. |
| B.401 | CytA | *Ephestia* spp. |
| B.402 | CytA | *Heliothis* spp. |
| B.403 | CytA | *Hellula undalis* |
| B.404 | CytA | *Keiferia lycopersicella* |
| B.405 | CytA | *Leucoptera scitella* |
| B.406 | CytA | *Lithocollethis* spp. |
| B.407 | CytA | *Lobesia botrana* |
| B.408 | CytA | *Ostrinia nubilalis* |
| B.409 | CytA | *Pandemis* spp. |
| B.410 | CytA | *Pectinophora gossyp.* |
| B.411 | CytA | *Phyllocnistis citrella* |
| B.412 | CytA | *Pieris* spp. |
| B.413 | CytA | *Plutella xylostella* |
| B.414 | CytA | *Scirpophaga* spp. |
| B.415 | CytA | *Sesamia* spp. |
| B.416 | CytA | *Sparganothis* spp. |
| B.417 | CytA | *Spodoptera* spp. |
| B.418 | CytA | *Tortrix* spp. |
| B.419 | CytA | *Trichoplusia ni* |
| B.420 | CytA | *Agriotes* spp. |
| B.421 | CytA | *Anthonomus grandis* |
| B.422 | CytA | *Curculio* spp. |
| B.423 | CytA | *Diabrotica balteata* |
| B.424 | CytA | *Leptinotarsa* spp. |
| B.425 | CytA | *Lissorhoptrus* spp. |
| B.426 | CytA | *Otiorhynchus* spp. |
| B.427 | CytA | *Aleurothrixus* spp. |
| B.428 | CytA | *Aleyrodes* spp. |
| B.429 | CytA | *Aonidiella* spp. |
| B.430 | CytA | *Aphididae* spp. |
| B.431 | CytA | *Aphis* spp. |
| B.432 | CytA | *Bemisia tabaci* |
| B.433 | CytA | *Empoasca* spp. |
| B.434 | CytA | *Mycus* spp. |
| B.435 | CytA | *Nephotettix* spp. |
| B.436 | CytA | *Nilaparvata* spp. |
| B.437 | CytA | *Pseudococcus* spp. |
| B.438 | CytA | *Psylla* spp. |
| B.439 | CytA | *Quadraspidiotus* spp. |
| B.440 | CytA | *Schizaphis* spp. |
| B.441 | CytA | *Trialeurodes* spp. |
| B.442 | CytA | *Lyriomyza* spp. |
| B.443 | CytA | *Oscinella* spp. |
| B.444 | CytA | *Phorbia* spp. |
| B.445 | CytA | *Frankliniella* spp. |
| B.446 | CytA | *Thrips* spp. |
| B.447 | CytA | *Scirtothrips aurantii* |
| B.448 | CytA | *Aceria* spp. |
| B.449 | CytA | *Aculus* spp. |
| B.450 | CytA | *Brevipalpus* spp. |
| B.451 | CytA | *Panonychus* spp. |
| B.452 | CytA | *Phyllocoptruta* spp. |
| B.453 | CytA | *Tetranychus* spp. |
| B.454 | CytA | *Heterodera* spp. |
| B.455 | CytA | *Meloidogyne* spp. |
| B.456 | VIP3 | *Adoxophyes* spp. |
| B.457 | VIP3 | *Agrotis* spp. |
| B.458 | VIP3 | *Alabama argillaceae* |
| B.459 | VIP3 | *Anticarsia gemmatalis* |
| B.460 | VIP3 | *Chilo* spp. |
| B.461 | VIP3 | *Clysia ambiguella* |
| B.462 | VIP3 | *Crocidolomia binotalis* |
| B.463 | VIP3 | *Cydia* spp. |
| B.464 | VIP3 | *Diparopsis castanea* |
| B.465 | VIP3 | *Earias* spp. |
| B.466 | VIP3 | *Ephestia* spp. |
| B.467 | VIP3 | *Heliothis* spp. |
| B.468 | VIP3 | *Hellula undalis* |
| B.469 | VIP3 | *Keiferia lycopersicella* |
| B.470 | VIP3 | *Leucoptera scitella* |
| B.471 | VIP3 | *Lithocollethis* spp. |
| B.472 | VIP3 | *Lobesia botrana* |
| B.473 | VIP3 | *Ostrinia nubilalis* |
| B.474 | VIP3 | *Pandemis* spp. |
| B.475 | VIP3 | *Pectinophora gossyp.* |
| B.476 | VIP3 | *Phyllocnistis citrella* |
| B.477 | VIP3 | *Pieris* spp. |
| B.478 | VIP3 | *Plutella xylostella* |
| B.479 | VIP3 | *Scirpophaga* spp. |
| B.480 | VIP3 | *Sesamia* spp. |
| B.481 | VIP3 | *Sparganothis* spp. |
| B.482 | VIP3 | *Spodoptera* spp. |
| B.483 | VIP3 | *Tortrix* spp. |
| B.484 | VIP3 | *Trichoplusia ni* |
| B.485 | VIP3 | *Agriotes* spp. |
| B.486 | VIP3 | *Anthonomus grandis* |
| B.487 | VIP3 | *Curculio* spp. |
| B.488 | VIP3 | *Diabrotica balteata* |
| B.489 | VIP3 | *Leptinotarsa* spp. |
| B.490 | VIP3 | *Lissorhoptrus* spp. |
| B.491 | VIP3 | *Otiorhynchus* spp. |
| B.492 | VIP3 | *Aleurothrixus* spp. |
| B.493 | VIP3 | *Aleyrodes* spp. |
| B.494 | VIP3 | *Aonidiella* spp. |
| B.495 | VIP3 | *Aphididae* spp. |
| B.496 | VIP3 | *Aphis* spp. |
| B.497 | VIP3 | *Bemisia tabaci* |
| B.498 | VIP3 | *Empoasca* spp. |
| B.499 | VIP3 | *Mycus* spp. |
| B.500 | VIP3 | *Nephotettix* spp. |
| B.501 | VIP3 | *Nilaparvata* spp. |
| B.502 | VIP3 | *Pseudococcus* spp. |
| B.503 | VIP3 | *Psylla* spp. |
| B.504 | VIP3 | *Quadraspidiotus* spp. |
| B.505 | VIP3 | *Schizaphis* spp. |
| B.506 | VIP3 | *Trialeurodes* spp. |
| B.507 | VIP3 | *Lyriomyza* spp. |
| B.508 | VIP3 | *Oscinella* spp. |
| B.509 | VIP3 | *Phorbia* spp. |
| B.510 | VIP3 | *Frankliniella* spp. |
| B.511 | VIP3 | *Thrips* spp. |
| B.512 | VIP3 | *Scirtothrips aurantii* |
| B.513 | VIP3 | *Aceria* spp. |
| B.514 | VIP3 | *Aculus* spp. |
| B.515 | VIP3 | *Brevipalpus* spp. |
| B.516 | VIP3 | *Panonychus* spp. |
| B.517 | VIP3 | *Phyllocoptruta* spp. |
| B.518 | VIP3 | *Tetranychus* spp. |
| B.519 | VIP3 | *Heterodera* spp. |
| B.520 | VIP3 | *Meloidogyne* spp. |
| B.521 | GL | *Adoxophyes* spp. |
| B.522 | GL | *Agrotis* spp. |
| B.523 | GL | *Alabama argillaceae* |
| B.524 | GL | *Anticarsia gemmatalis* |
| B.525 | GL | *Chilo* spp. |
| B.526 | GL | *Clysia ambiguella* |
| B.527 | GL | *Crocidolomia binotalis* |
| B.528 | GL | *Cydia* spp. |

TABLE B-continued

| | AP | Control of |
|---|---|---|
| B.529 | GL | Diparopsis castanea |
| B.530 | GL | Earias spp. |
| B.531 | GL | Ephestia spp. |
| B.532 | GL | Heliothis spp. |
| B.533 | GL | Hellula undalis |
| B.534 | GL | Keiferia lycopersicella |
| B.535 | GL | Leucoptera scitella |
| B.536 | GL | Lithocollethis spp. |
| B.537 | GL | Lobesia botrana |
| B.538 | GL | Ostrinia nubilalis |
| B.539 | GL | Pandemis spp. |
| B.540 | GL | Pectinophora gossyp. |
| B.541 | GL | Phyllocnistis citrella |
| B.542 | GL | Pieris spp. |
| B.543 | GL | Plutella xylostella |
| B.544 | GL | Scirpophaga spp. |
| B.545 | GL | Sesamia spp. |
| B.546 | GL | Sparganothis spp. |
| B.547 | GL | Spodoptera spp. |
| B.548 | GL | Tortrix spp. |
| B.549 | GL | Trichoplusia ni |
| B.550 | GL | Agriotes spp. |
| B.551 | GL | Anthonomus grandis |
| B.552 | GL | Curculio spp. |
| B.553 | GL | Diabrotica balteata |
| B.554 | GL | Leptinotarsa spp. |
| B.555 | GL | Lissorhoptrus spp. |
| B.556 | GL | Otiorhynchus spp. |
| B.557 | GL | Aleurothrixus spp. |
| B.558 | GL | Aleyrodes spp. |
| B.559 | GL | Aonidiella spp. |
| B.560 | GL | Aphididae spp. |
| B.561 | GL | Aphis spp. |
| B.562 | GL | Bemisia tabaci |
| B.563 | GL | Empoasca spp. |
| B.564 | GL | Mycus spp. |
| B.565 | GL | Nephotettix spp. |
| B.566 | GL | Nilaparvata spp. |
| B.567 | GL | Pseudococcus spp. |
| B.568 | GL | Psylla spp. |
| B.569 | GL | Quadraspidiotus spp. |
| B.570 | GL | Schizaphis spp. |
| B.571 | GL | Trialeurodes spp. |
| B.572 | GL | Lyriomyza spp. |
| B.573 | GL | Oscinella spp. |
| B.574 | GL | Phorbia spp. |
| B.575 | GL | Frankliniella spp. |
| B.576 | GL | Thrips spp. |
| B.577 | GL | Scirtothrips aurantii |
| B.578 | GL | Aceria spp. |
| B.579 | GL | Aculus spp. |
| B.580 | GL | Brevipalpus spp. |
| B.581 | GL | Panonychus spp. |
| B.582 | GL | Phyllocoptruta spp. |
| B.583 | GL | Tetranychus spp. |
| B.584 | GL | Heterodera spp. |
| B.585 | GL | Meloidogyne spp. |
| B.586 | PL | Adoxophyes spp. |
| B.587 | PL | Agrotis spp. |
| B.588 | PL | Alabama argillaceae |
| B.589 | PL | Anticarsia gemmatalis |
| B.590 | PL | Chilo spp. |
| B.591 | PL | Clysia ambiguella |
| B.592 | PL | Crocidolomia binotalis |
| B.593 | PL | Cydia spp. |
| B.594 | PL | Diparopsis castanea |
| B.595 | PL | Earias spp. |
| B.596 | PL | Ephestia spp. |
| B.597 | PL | Heliothis spp. |
| B.598 | PL | Hellula undalis |
| B.599 | PL | Keiferia lycopersicella |
| B.600 | PL | Leucoptera scitella |
| B.601 | PL | Lithocollethis spp. |
| B.602 | PL | Lobesia botrana |
| B.603 | PL | Ostrinia nubilalis |
| B.604 | PL | Pandemis spp. |
| B.605 | PL | Pectinophora gossyp. |
| B.606 | PL | Phyllocnistis citrella |
| B.607 | PL | Pieris spp. |
| B.608 | PL | Plutella xylostella |
| B.609 | PL | Scirpophaga spp. |
| B.610 | PL | Sesamia spp. |
| B.611 | PL | Sparganothis spp. |
| B.612 | PL | Spodoptera spp. |
| B.613 | PL | Tortrix spp. |
| B.614 | PL | Trichoplusia ni |
| B.615 | PL | Agriotes spp. |
| B.616 | PL | Anthonomus grandis |
| B.617 | PL | Curculio spp. |
| B.618 | PL | Diabrotica balteata |
| B.619 | PL | Leptinotarsa spp. |
| B.620 | PL | Lissorhoptrus spp. |
| B.621 | PL | Otiorhynchus spp. |
| B.622 | PL | Aleurothrixus spp. |
| B.623 | PL | Aleyrodes spp. |
| B.624 | PL | Aonidiella spp. |
| B.625 | PL | Aphididae spp. |
| B.626 | PL | Aphis spp. |
| B.627 | PL | Bemisia tabaci |
| B.628 | PL | Empoasca spp. |
| B.629 | PL | Mycus spp. |
| B.630 | PL | Nephotettix spp. |
| B.631 | PL | Nilaparvata spp. |
| B.632 | PL | Pseudococcus spp. |
| B.633 | PL | Psylla spp. |
| B.634 | PL | Quadraspidiotus spp. |
| B.635 | PL | Schizaphis spp. |
| B.636 | PL | Trialeurodes spp. |
| B.637 | PL | Lyriomyza spp. |
| B.638 | PL | Oscinella spp. |
| B.639 | PL | Phorbia spp. |
| B.640 | PL | Frankliniella spp. |
| B.641 | PL | Thrips spp. |
| B.642 | PL | Scirtothrips aurantii |
| B.643 | PL | Aceria spp. |
| B.644 | PL | Aculus spp. |
| B.645 | PL | Brevipalpus spp. |
| B.646 | PL | Panonychus spp. |
| B.647 | PL | Phyllocoptruta spp. |
| B.648 | PL | Tetranychus spp. |
| B.649 | PL | Heterodera spp. |
| B.650 | PL | Meloidogyne spp. |
| B.651 | XN | Adoxophyes spp. |
| B.652 | XN | Agrotis spp. |
| B.653 | XN | Alabama argillaceae |
| B.654 | XN | Anticarsia gemmatalis |
| B.655 | XN | Chilo spp. |
| B.656 | XN | Clysia ambiguella |
| B.657 | XN | Crocidolomia binotalis |
| B.658 | XN | Cydia spp. |
| B.659 | XN | Diparopsis castanea |
| B.660 | XN | Earias spp. |
| B.661 | XN | Ephestia spp. |
| B.662 | XN | Heliothis spp. |
| B.663 | XN | Hellula undalis |
| B.664 | XN | Keiferia lycopersicella |
| B.665 | XN | Leucoptera scitella |
| B.666 | XN | Lithocollethis spp. |

TABLE B-continued

| | AP | Control of |
|---|---|---|
| B.667 | XN | *Lobesia botrana* |
| B.668 | XN | *Ostrinia nubilalis* |
| B.669 | XN | *Pandemis* spp. |
| B.670 | XN | *Pectinophora gossyp.* |
| B.671 | XN | *Phyllocnistis citrella* |
| B.672 | XN | *Pieris* spp. |
| B.673 | XN | *Plutella xylostella* |
| B.674 | XN | *Scirpophaga* spp. |
| B.675 | XN | *Sesamia* spp. |
| B.676 | XN | *Sparganothis* spp. |
| B.677 | XN | *Spodoptera* spp. |
| B.678 | XN | *Tortrix* spp. |
| B.679 | XN | *Trichoplusia ni* |
| B.680 | XN | *Agriotes* spp. |
| B.681 | XN | *Anthonomus grandis* |
| B.682 | XN | *Curculio* spp. |
| B.683 | XN | *Diabrotica balteata* |
| B.684 | XN | *Leptinotarsa* spp. |
| B.685 | XN | *Lissorhoptrus* spp. |
| B.686 | XN | *Otiorhynchus* spp. |
| B.687 | XN | *Aleurothrixus* spp. |
| B.688 | XN | *Aleyrodes* spp. |
| B.689 | XN | *Aonidiella* spp. |
| B.690 | XN | *Aphididae* spp. |
| B.691 | XN | *Aphis* spp. |
| B.692 | XN | *Bemisia tabaci* |
| B.693 | XN | *Empoasca* spp. |
| B.694 | XN | *Mycus* spp. |
| B.695 | XN | *Nephotettix* spp. |
| B.696 | XN | *Nilaparvata* spp. |
| B.697 | XN | *Pseudococcus* spp. |
| B.698 | XN | *Psylla* spp. |
| B.699 | XN | *Quadraspidiotus* spp. |
| B.700 | XN | *Schizaphis* spp. |
| B.701 | XN | *Trialeurodes* spp. |
| B.702 | XN | *Lyriomyza* spp. |
| B.703 | XN | *Oscinella* spp. |
| B.704 | XN | *Phorbia* spp. |
| B.705 | XN | *Frankliniella* spp. |
| B.706 | XN | *Thrips* spp. |
| B.707 | XN | *Scirtothrips aurantii* |
| B.708 | XN | *Aceria* spp. |
| B.709 | XN | *Aculus* spp. |
| B.710 | XN | *Brevipalpus* spp. |
| B.711 | XN | *Panonychus* spp. |
| B.712 | XN | *Phyllocoptruta* spp. |
| B.713 | XN | *Tetranychus* spp. |
| B.714 | XN | *Heterodera* spp. |
| B.715 | XN | *Meloidogyne* spp. |
| B.716 | PInh. | *Adoxophyes* spp. |
| B.717 | PInh. | *Agrotis* spp. |
| B.718 | PInh. | *Alabama argillaceae* |
| B.719 | PInh. | *Anticarsia gemmatalis* |
| B.720 | PInh. | *Chilo* spp. |
| B.721 | PInh. | *Clysia ambiguella* |
| B.722 | PInh. | *Crocidolomia binotalis* |
| B.723 | PInh. | *Cydia* spp. |
| B.724 | PInh. | *Diaparopsis castanea* |
| B.725 | PInh. | *Earias* spp. |
| B.726 | PInh. | *Ephestia* spp. |
| B.727 | PInh. | *Heliothis* spp. |
| B.728 | PInh. | *Hellula undalis* |
| B.729 | PInh. | *Keiferia lycopersicella* |
| B.730 | PInh. | *Leucoptera scitella* |
| B.731 | PInh. | *Lithocollethis* spp. |
| B.732 | PInh. | *Lobesia botrana* |
| B.733 | PInh. | *Ostrinia nubilalis* |
| B.734 | PInh. | *Pandemis* spp. |
| B.735 | PInh. | *Pectinophora gossyp.* |
| B.736 | PInh. | *Phyllocnistis citrella* |
| B.737 | PInh. | *Pieris* spp. |
| B.738 | PInh. | *Plutella xylostella* |
| B.739 | PInh. | *Scirpophaga* spp. |
| B.740 | PInh. | *Sesamia* spp. |
| B.741 | PInh. | *Sparganothis* spp. |
| B.742 | PInh. | *Spodoptera* spp. |
| B.743 | PInh. | *Tortrix* spp. |
| B.744 | PInh. | *Trichoplusia ni* |
| B.745 | PInh. | *Agriotes* spp. |
| B.746 | PInh. | *Anthonomus grandis* |
| B.747 | PInh. | *Curculio* spp. |
| B.748 | PInh. | *Diabrotica balteata* |
| B.749 | PInh. | *Leptinotarsa* spp. |
| B.750 | PInh. | *Lissorhoptrus* spp. |
| B.751 | PInh. | *Otiorhynchus* spp. |
| B.752 | PInh. | *Aleurothrixus* spp. |
| B.753 | PInh. | *Aleyrodes* spp. |
| B.754 | PInh. | *Aonidiella* spp. |
| B.755 | PInh. | *Aphididae* spp. |
| B.756 | PInh. | *Aphis* spp. |
| B.757 | PInh. | *Bemisia tabaci* |
| B.758 | PInh. | *Empoasca* spp. |
| B.759 | PInh. | *Mycus* spp. |
| B.760 | PInh. | *Nephotettix* spp. |
| B.761 | PInh. | *Nilaparvata* spp. |
| B.762 | PInh. | *Pseudococcus* spp. |
| B.763 | PInh. | *Psylla* spp. |
| B.764 | PInh. | *Quadraspidiotus* spp. |
| B.765 | PInh. | *Schizaphis* spp. |
| B.766 | PInh. | *Trialeurodes* spp. |
| B.767 | PInh. | *Lyriomyza* spp. |
| B.768 | PInh. | *Oscinella* spp. |
| B.769 | PInh. | *Phorbia* spp. |
| B.770 | PInh. | *Frankliniella* spp. |
| B.771 | PInh. | *Thrips* spp. |
| B.772 | PInh. | *Scirtothrips aurantii* |
| B.773 | PInh. | *Aceria* spp. |
| B.774 | PInh. | *Aculus* spp. |
| B.775 | PInh. | *Brevipalpus* spp. |
| B.776 | PInh. | *Panonychus* spp. |
| B.777 | PInh. | *Phyllocoptruta* spp. |
| B.778 | PInh. | *Tetranychus* spp. |
| B.779 | PInh. | *Heterodera* spp. |
| B.780 | PInh. | *Meloidogyne* spp. |
| B.781 | PLec. | *Adoxophyes* spp. |
| B.782 | PLec. | *Agrotis* spp. |
| B.783 | PLec. | *Alabama argillaceae* |
| B.784 | PLec. | *Anticarsia gemmatalis* |
| B.785 | PLec. | *Chilo* spp. |
| B.786 | PLec. | *Clysia ambiguella* |
| B.787 | PLec. | *Crocidolomia binotalis* |
| B.788 | PLec. | *Cydia* spp. |
| B.789 | PLec. | *Diaparopsis castanea* |
| B.790 | PLec. | *Earias* spp. |
| B.791 | PLec. | *Ephestia* spp. |
| B.792 | PLec. | *Heliothis* spp. |
| B.793 | PLec. | *Hellula undalis* |
| B.794 | PLec. | *Keiferia lycopersicella* |
| B.795 | PLec. | *Leucoptera scitella* |
| B.796 | PLec. | *Lithocollethis* spp. |
| B.797 | PLec. | *Lobesia botrana* |
| B.798 | PLec. | *Ostrinia nubilalis* |
| B.799 | PLec. | *Pandemis* spp. |
| B.800 | PLec. | *Pectinophora gossyp.* |
| B.801 | PLec. | *Phyllocnistis citrella* |
| B.802 | PLec. | *Pieris* spp. |
| B.803 | PLec. | *Plutella xylostella* |
| B.804 | PLec. | *Scirpophaga* spp. |
| B.805 | PLec. | *Sesamia* spp. |

TABLE B-continued

| | AP | Control of |
|---|---|---|
| B.806 | PLec. | *Sparganothis* spp. |
| B.807 | PLec. | *Spodoptera* spp. |
| B.808 | PLec. | *Tortrix* spp. |
| B.809 | PLec. | *Trichoplusia ni* |
| B.810 | PLec. | *Agriotes* spp. |
| B.811 | PLec. | *Anthonomus grandis* |
| B.812 | PLec. | *Curculio* spp. |
| B.813 | PLec. | *Diabrotica balteata* |
| B.814 | PLec. | *Leptinotarsa* spp. |
| B.815 | PLec. | *Lissorhoptrus* spp. |
| B.816 | PLec. | *Otiorhynchus* spp. |
| B.817 | PLec. | *Aleurothrixus* spp. |
| B.818 | PLec. | *Aleyrodes* spp. |
| B.819 | PLec. | *Aonidiella* spp. |
| B.820 | PLec. | *Aphididae* spp. |
| B.821 | PLec. | *Aphis* spp. |
| B.822 | PLec. | *Bemisia tabaci* |
| B.823 | PLec. | *Empoasca* spp. |
| B.824 | PLec. | *Mycus* spp. |
| B.825 | PLec. | *Nephotettix* spp. |
| B.826 | PLec. | *Nilaparvata* spp. |
| B.827 | PLec. | *Pseudococcus* spp. |
| B.828 | PLec. | *Psylla* spp. |
| B.829 | PLec. | *Quadraspidiotus* spp. |
| B.830 | PLec. | *Schizaphis* spp. |
| B.831 | PLec. | *Trialeurodes* spp. |
| B.832 | PLec. | *Lyriomyza* spp. |
| B.833 | PLec. | *Oscinella* spp. |
| B.834 | PLec. | *Phorbia* spp. |
| B.835 | PLec. | *Frankliniella* spp. |
| B.836 | PLec. | *Thrips* spp. |
| B.837 | PLec. | *Scirtothrips aurantii* |
| B.838 | PLec. | *Aceria* spp. |
| B.839 | PLec. | *Aculus* spp. |
| B.840 | PLec. | *Brevipalpus* spp. |
| B.841 | PLec. | *Panonychus* spp. |
| B.842 | PLec. | *Phyllocoptruta* spp. |
| B.843 | PLec. | *Tetranychus* spp. |
| B.844 | PLec. | *Heterodera* spp. |
| B.845 | PLec. | *Meloidogyne* spp. |
| B.846 | Aggl. | *Adoxophyes* spp. |
| B.847 | Aggl. | *Agrotis* spp. |
| B.848 | Aggl. | *Alabama argillaceae* |
| B.849 | Aggl. | *Anticarsia gemmatalis* |
| B.850 | Aggl. | *Chilo* spp. |
| B.851 | Aggl. | *Clysia ambiguella* |
| B.852 | Aggl. | *Crocidolomia binotalis* |
| B.853 | Aggl. | *Cydia* spp. |
| B.854 | Aggl. | *Diparopsis castanea* |
| B.855 | Aggl. | *Earias* spp. |
| B.856 | Aggl. | *Ephestia* spp. |
| B.857 | Aggl. | *Heliothis* spp. |
| B.858 | Aggl. | *Hellula undalis* |
| B.859 | Aggl. | *Keiferia lycopersicella* |
| B.860 | Aggl. | *Leucoptera scitella* |
| B.861 | Aggl. | *Lithocollethis* spp. |
| B.862 | Aggl. | *Lobesia botrana* |
| B.863 | Aggl. | *Ostrinia nubilalis* |
| B.864 | Aggl. | *Pandemis* spp. |
| B.865 | Aggl. | *Pectinophora gossyp.* |
| B.866 | Aggl. | *Phyllocnistis citrella* |
| B.867 | Aggl. | *Pieris* spp. |
| B.868 | Aggl. | *Plutella xylostella* |
| B.869 | Aggl. | *Scirpophaga* spp. |
| B.870 | Aggl. | *Sesamia* spp. |
| B.871 | Aggl. | *Sparganothis* spp. |
| B.872 | Aggl. | *Spodoptera* spp. |
| B.873 | Aggl. | *Tortrix* spp. |
| B.874 | Aggl. | *Trichoplusia ni* |
| B.875 | Aggl. | *Agriotes* spp. |
| B.876 | Aggl. | *Anthonomus grandis* |
| B.877 | Aggl. | *Curculio* spp. |
| B.878 | Aggl. | *Diabrotica balteata* |
| B.879 | Aggl. | *Leptinotarsa* spp. |
| B.880 | Aggl. | *Lissorhoptrus* spp. |
| B.881 | Aggl. | *Otiorhynchus* spp. |
| B.882 | Aggl. | *Aleurothrixus* spp. |
| B.883 | Aggl. | *Aleyrodes* spp. |
| B.884 | Aggl. | *Aonidiella* spp. |
| B.885 | Aggl. | *Aphididae* spp. |
| B.886 | Aggl. | *Aphis* spp. |
| B.887 | Aggl. | *Bemisia tabaci* |
| B.888 | Aggl. | *Empoasca* spp. |
| B.889 | Aggl. | *Mycus* spp. |
| B.890 | Aggl. | *Nephotettix* spp. |
| B.891 | Aggl. | *Nilaparvata* spp. |
| B.892 | Aggl. | *Pseudococcus* spp. |
| B.893 | Aggl. | *Psylla* spp. |
| B.894 | Aggl. | *Quadraspidiotus* spp. |
| B.895 | Aggl. | *Schizaphis* spp. |
| B.896 | Aggl. | *Trialeurodes* spp. |
| B.897 | Aggl. | *Lyriomyza* spp. |
| B.898 | Aggl. | *Oscinella* spp. |
| B.899 | Aggl. | *Phorbia* spp. |
| B.900 | Aggl. | *Frankliniella* spp. |
| B.901 | Aggl. | *Thrips* spp. |
| B.902 | Aggl. | *Scirtothrips aurantii* |
| B.903 | Aggl. | *Aceria* spp. |
| B.904 | Aggl. | *Aculus* spp. |
| B.905 | Aggl. | *Brevipalpus* spp. |
| B.906 | Aggl. | *Panonychus* spp. |
| B.907 | Aggl. | *Phyllocoptruta* spp. |
| B.908 | Aggl. | *Tetranychus* spp. |
| B.909 | Aggl. | *Heterodera* spp. |
| B.910 | Aggl. | *Meloidogyne* spp. |
| B.911 | CO | *Adoxophyes* spp. |
| B.912 | CO | *Agrotis* spp. |
| B.913 | CO | *Alabama argillaceae* |
| B.914 | CO | *Anticarsia gemmatalis* |
| B.915 | CO | *Chilo* spp. |
| B.916 | CO | *Clysia ambiguella* |
| B.917 | CO | *Crocidolomia binotalis* |
| B.918 | CO | *Cydia* spp. |
| B.919 | CO | *Diparopsis castanea* |
| B.920 | CO | *Earias* spp. |
| B.921 | CO | *Ephestia* spp. |
| B.922 | CO | *Heliothis* spp. |
| B.923 | CO | *Hellula undalis* |
| B.924 | CO | *Keiferia lycopersicella* |
| B.925 | CO | *Leucoptera scitella* |
| B.926 | CO | *Lithocollethis* spp. |
| B.927 | CO | *Lobesia botrana* |
| B.928 | CO | *Ostrinia nubilalis* |
| B.929 | CO | *Pandemis* spp. |
| B.930 | CO | *Pectinophora gossyp.* |
| B.931 | CO | *Phyllocnistis citrella* |
| B.932 | CO | *Pieris* spp. |
| B.933 | CO | *Plutella xylostella* |
| B.934 | CO | *Scirpophaga* spp. |
| B.935 | CO | *Sesamia* spp. |
| B.936 | CO | *Sparganothis* spp. |
| B.937 | CO | *Spodoptera* spp. |
| B.938 | CO | *Tortrix* spp. |
| B.939 | CO | *Trichoplusia ni* |
| B.940 | CO | *Agriotes* spp. |
| B.941 | CO | *Anthonomus grandis* |
| B.942 | CO | *Curculio* spp. |
| B.943 | CO | *Diabrotica balteata* |
| B.944 | CO | *Leptinotarsa* spp. |

TABLE B-continued

| | AP | Control of |
|---|---|---|
| B.945 | CO | Lissorhoptrus spp. |
| B.946 | CO | Otiorhynchus spp. |
| B.947 | CO | Aleurothrixus spp. |
| B.948 | CO | Aleyrodes spp. |
| B.949 | CO | Aonidiella spp. |
| B.950 | CO | Aphididae spp. |
| B.951 | CO | Aphis spp. |
| B.952 | CO | Bemisia tabaci |
| B.953 | CO | Empoasca spp. |
| B.954 | CO | Mycus spp. |
| B.955 | CO | Nephotettix spp. |
| B.956 | CO | Nilaparvata spp. |
| B.957 | CO | Pseudococcus spp. |
| B.958 | CO | Psylla spp. |
| B.959 | CO | Quadraspidiotus spp. |
| B.960 | CO | Schizaphis spp. |
| B.961 | CO | Trialeurodes spp. |
| B.962 | CO | Lyriomyza spp. |
| B.963 | CO | Oscinella spp. |
| B.964 | CO | Phorbia spp. |
| B.965 | CO | Frankliniella spp. |
| B.966 | CO | Thrips spp. |
| B.967 | CO | Scirtothrips aurantii |
| B.968 | CO | Aceria spp. |
| B.969 | CO | Aculus spp. |
| B.970 | CO | Brevipalpus spp. |
| B.971 | CO | Panonychus spp. |
| B.972 | CO | Phyllocoptruta spp. |
| B.973 | CO | Tetranychus spp. |
| B.974 | CO | Heterodera spp. |
| B.975 | CO | Meloidogyne spp. |
| B.976 | CH | Adoxophyes spp. |
| B.977 | CH | Agrotis spp. |
| B.978 | CH | Alabama argillaceae |
| B.979 | CH | Anticarsia gemmatalis |
| B.980 | CH | Chilo spp. |
| B.981 | CH | Clysia ambiguella |
| B.982 | CH | Crocidolomia binotalis |
| B.983 | CH | Cydia spp. |
| B.984 | CH | Diparopsis castanea |
| B.985 | CH | Earias spp. |
| B.986 | CH | Ephestia spp. |
| B.987 | CH | Heliothis spp. |
| B.988 | CH | Hellula undalis |
| B.989 | CH | Keiferia lycopersicella |
| B.990 | CH | Leucoptera scitella |
| B.991 | CH | Lithocollethis spp. |
| B.992 | CH | Lobesia botrana |
| B.993 | CH | Ostrinia nubilalis |
| B.994 | CH | Pandemis spp. |
| B.995 | CH | Pectinophora gossyp. |
| B.996 | CH | Phyllocnistis citrella |
| B.997 | CH | Pieris spp. |
| B.998 | CH | Plutella xylostella |
| B.999 | CH | Scirpophaga spp. |
| B.1000 | CH | Sesamia spp. |
| B.1001 | CH | Sparganothis spp. |
| B.1002 | CH | Spodoptera spp. |
| B.1003 | CH | Tortrix spp. |
| B.1004 | CH | Trichoplusia ni |
| B.1005 | CH | Agriotes spp. |
| B.1006 | CH | Anthonomus grandis |
| B.1007 | CH | Curculio spp. |
| B.1008 | CH | Diabrotica balteata |
| B.1009 | CH | Leptinotarsa spp. |
| B.1010 | CH | Lissorhoptrus spp. |
| B.1011 | CH | Otiorhynchus spp. |
| B.1012 | CH | Aleurothrixus spp. |
| B.1013 | CH | Aleyrodes spp. |
| B.1014 | CH | Aonidiella spp. |
| B.1015 | CH | Aphididae spp. |
| B.1016 | CH | Aphis spp. |
| B.1017 | CH | Bemisia tabaci |
| B.1018 | CH | Empoasca spp. |
| B.1019 | CH | Mycus spp. |
| B.1020 | CH | Nephotettix spp. |
| B.1021 | CH | Nilaparvata spp. |
| B.1022 | CH | Pseudococcus spp. |
| B.1023 | CH | Psylla spp. |
| B.1024 | CH | Quadraspidiotus spp. |
| B.1025 | CH | Schizaphis spp. |
| B.1026 | CH | Trialeurodes spp. |
| B.1027 | CH | Lyriomyza spp. |
| B.1028 | CH | Oscinella spp. |
| B.1029 | CH | Phorbia spp. |
| B.1030 | CH | Frankliniella spp. |
| B.1031 | CH | Thrips spp. |
| B.1032 | CH | Scirtothrips aurantii |
| B.1033 | CH | Aceria spp. |
| B.1034 | CH | Aculus spp. |
| B.1035 | CH | Brevipalpus spp. |
| B.1036 | CH | Panonychus spp. |
| B.1037 | CH | Phyllocoptruta spp. |
| B.1038 | CH | Tetranychus spp. |
| B.1039 | CH | Heterodera spp. |
| B.1040 | CH | Meloidogyne spp. |
| B.1041 | SS | Adoxophyes spp. |
| B.1042 | SS | Agrotis spp. |
| B.1043 | SS | Alabama argillaceae |
| B.1044 | SS | Anticarsia gemmatalis |
| B.1045 | SS | Chilo spp. |
| B.1046 | SS | Clysia ambiguella |
| B.1047 | SS | Crocidolomia binotalis |
| B.1048 | SS | Cydia spp. |
| B.1049 | SS | Diparopsis castanea |
| B.1050 | SS | Earias spp. |
| B.1051 | SS | Ephestia spp. |
| B.1052 | SS | Heliothis spp. |
| B.1053 | SS | Hellula undalis |
| B.1054 | SS | Keiferia lycopersicella |
| B.1055 | SS | Leucoptera scitella |
| B.1056 | SS | Lithocollethis spp. |
| B.1057 | SS | Lobesia botrana |
| B.1058 | SS | Ostrinia nubilalis |
| B.1059 | SS | Pandemis spp. |
| B.1060 | SS | Pectinophora gossyp. |
| B.1061 | SS | Phyllocnistis citrella |
| B.1062 | SS | Pieris spp. |
| B.1063 | SS | Plutella xylostella |
| B.1064 | SS | Scirpophaga spp. |
| B.1065 | SS | Sesamia spp. |
| B.1066 | SS | Sparganothis spp. |
| B.1067 | SS | Spodoptera spp. |
| B.1068 | SS | Tortrix spp. |
| B.1069 | SS | Trichoplusia ni |
| B.1070 | SS | Agriotes spp. |
| B.1071 | SS | Anthonomus grandis |
| B.1072 | SS | Curculio spp. |
| B.1073 | SS | Diabrotica balteata |
| B.1074 | SS | Leptinotarsa spp. |
| B.1075 | SS | Lissorhoptrus spp. |
| B.1076 | SS | Otiorhynchus spp. |
| B.1077 | SS | Aleurothrixus spp. |
| B.1078 | SS | Aleyrodes spp. |
| B.1079 | SS | Aonidiella spp. |
| B.1080 | SS | Aphididae spp. |
| B.1081 | SS | Aphis spp. |
| B.1082 | SS | Bemisia tabaci |
| B.1083 | SS | Empoasca spp. |
| B.1084 | SS | Mycus spp. |

TABLE B-continued

| AP | | Control of |
|---|---|---|
| B.1085 | SS | Nephotettix spp. |
| B.1086 | SS | Nilaparvata spp. |
| B.1087 | SS | Pseudococcus spp. |
| B.1088 | SS | Psylla spp. |
| B.1089 | SS | Quadraspidiotus spp. |
| B.1090 | SS | Schizaphis spp. |
| B.1091 | SS | Trialeurodes spp. |
| B.1092 | SS | Lyriomyza spp. |
| B.1093 | SS | Oscinella spp. |
| B.1094 | SS | Phorbia spp. |
| B.1095 | SS | Frankliniella spp. |
| B.1096 | SS | Thrips spp. |
| B.1097 | SS | Scirtothrips aurantii |
| B.1098 | SS | Aceria spp. |
| B.1099 | SS | Aculus spp. |
| B.1100 | SS | Brevipalpus spp. |
| B.1101 | SS | Panonychus spp. |
| B.1102 | SS | Phyllocoptruta spp. |
| B.1103 | SS | Tetranychus spp. |
| B.1104 | SS | Heterodera spp. |
| B.1105 | SS | Meloidogyne spp. |
| B.1106 | HO | Adoxophyes spp. |
| B.1107 | HO | Agrotis spp. |
| B.1108 | HO | Alabama argillaceae |
| B.1109 | HO | Anticarsia gemmatalis |
| B.1110 | HO | Chilo spp. |
| B.1111 | HO | Clysia ambiguella |
| B.1112 | HO | Crocidolomia binotalis |
| B.1113 | HO | Cydia spp. |
| B.1114 | HO | Diparopsis castanea |
| B.1115 | HO | Earias spp. |
| B.1116 | HO | Ephestia spp. |
| B.1117 | HO | Heliothis spp. |
| B.1118 | HO | Hellula undalis |
| B.1119 | HO | Keiferia lycopersicella |
| B.1120 | HO | Leucoptera scitella |
| B.1121 | HO | Lithocollethis spp. |
| B.1122 | HO | Lobesia botrana |
| B.1123 | HO | Ostrinia nubilalis |
| B.1124 | HO | Pandemis spp. |
| B.1125 | HO | Pectinophora gossypiella |
| B.1126 | HO | Phyllocnistis citrella |
| B.1127 | HO | Pieris spp. |
| B.1128 | HO | Plutella xylostella |
| B.1129 | HO | Scirpophaga spp. |
| B.1130 | HO | Sesamia spp. |
| B.1131 | HO | Sparganothis spp. |
| B.1132 | HO | Spodoptera spp. |
| B.1133 | HO | Tortrix spp. |
| B.1134 | HO | Trichoplusia ni |
| B.1135 | HO | Agriotes spp. |
| B.1136 | HO | Anthonomus grandis |
| B.1137 | HO | Curculio spp. |
| B.1138 | HO | Diabrotica balteata |
| B.1139 | HO | Leptinotarsa spp. |
| B.1140 | HO | Lissorhoptrus spp. |
| B.1141 | HO | Otiorhynchus spp. |
| B.1142 | HO | Aleurothrixus spp. |
| B.1143 | HO | Aleyrodes spp. |
| B.1144 | HO | Aonidiella spp. |
| B.1145 | HO | Aphididae spp. |
| B.1146 | HO | Aphis spp. |
| B.1147 | HO | Bemisia tabaci |
| B.1148 | HO | Empoasca spp. |
| B.1149 | HO | Mycus spp. |
| B.1150 | HO | Nephotettix spp. |
| B.1151 | HO | Nilaparvata spp. |
| B.1152 | HO | Pseudococcus spp. |
| B.1153 | HO | Psylla spp. |
| B.1154 | HO | Quadraspidiotus spp. |
| B.1155 | HO | Schizaphis spp. |
| B.1156 | HO | Trialeurodes spp. |
| B.1157 | HO | Lyriomyza spp. |
| B.1158 | HO | Oscinella spp. |
| B.1159 | HO | Phorbia spp. |
| B.1160 | HO | Frankliniella spp. |
| B.1161 | HO | Thrips spp. |
| B.1162 | HO | Scirtothrips aurantii |
| B.1163 | HO | Aceria spp. |
| B.1164 | HO | Aculus spp. |
| B.1165 | HO | Brevipalpus spp. |
| B.1166 | HO | Panonychus spp. |
| B.1167 | HO | Phyllocoptruta spp. |
| B.1168 | HO | Tetranychus spp. |
| B.1169 | HO | Heterodera spp. |
| B.1170 | HO | Meloidogyne spp. |

Table B:
The following abreviations are used in the table:
Active Principle of transgenic plant: AP
Photorhabdus luminescens: PL
Xenorhabdus nematophilus: XN
Proteinase Inhibitors: PInh.
Plant lectins PLec.
Agglutinins: Aggl.
3-Hydroxysteroid oxidase: HO
Cholesteroloxidase: CO
Chitinase: CH
Glucanase: GL
Stilbensynthase SS

BIOLOGICAL EXAMPLES

Table 1: A method of controlling pests comprising the application of thiamethoxam to transgenic cotton, wherein the combination of the active principle expressed by the transgenic plant and the pest to be controlled correspond to anyone of the individualised combinations B.1 to B.1170 of table B.

Table 2: A method of controlling pests comprising the application of thiamethoxam to transgenic rice, wherein the combination of the active principle expressed by the transgenic plant and the pest to be controlled correspond to anyone of the individualised combinations B.1 to B.1170 of table B.

Table 3: A method of controlling pests comprising the application of thiamethoxam to transgenic potatoes, wherein the combination of the active principle expressed by the transgenic plant and the pest to be controlled correspond to anyone of the individualised combinations B.1 to B.1170 of table B.

Table 4: A method of controlling pests comprising the application of thiamethoxam to transgenic brassica, wherein the combination of the active principle expressed by the transgenic plant and the pest to be controlled correspond to anyone of the individualised combinations B.1 to B.1170 of table B.

Table 5: A method of controlling pests comprising the application of thiamethoxam to transgenic tomatoes, wherein the combination of the active principle expressed by the transgenic plant and the pest to be controlled correspond to anyone of the individualised combinations B.1 to B.1170 of table B.

Table 6: A method of controlling pests comprising the application of thiamethoxam to transgenic cucurbits, wherein the combination of the active principle expressed by the transgenic plant and the pest to be controlled correspond to anyone of the individualised combinations B.1 to B.1170 of table B.

Table 7: A method of controlling pests comprising the application of thiamethoxam to transgenic soybeans, wherein the combination of the active principle expressed by the transgenic plant and the pest to be controlled correspond to anyone of the individualised combinations B.1 to B.1170 of table B.

Table 8: A method of controlling pests comprising the application of thiamethoxam to transgenic maize, wherein the combination of the active principle expressed by the transgenic plant and the pest to be controlled correspond to anyone of the individualised combinations B.1 to B.1170 of table B.

Table 9: A method of controlling pests comprising the application of thiamethoxam to transgenic wheat, wherein the combination of the active principle expressed by the transgenic plant and the pest to be controlled correspond to anyone of the individualised combinations B.1 to B.1170 of table B.

Table 10: A method of controlling pests comprising the application of thiamethoxam to transgenic bananas, wherein the combination of the active principle expressed by the transgenic plant and the pest to be controlled correspond to anyone of the individualised combinations B.1 to B.1170 of table B.

Table 11: A method of controlling pests comprising the application of thiamethoxam to transgenic citrus trees, wherein the combination of the active principle expressed by the transgenic plant and the pest to be controlled correspond to anyone of the individualised combinations B.1 to B.1170 of table B.

Table 12: A method of controlling pests comprising the application of thiamethoxam to transgenic pome fruit trees, wherein the combination of the active principle expressed by the transgenic plant and the pest to be controlled correspond to anyone of the individualised combinations B.1 to B.1170 of table B.

Table 13: A method of controlling pests comprising the application of thiamethoxam to transgenic peppers, wherein the combination of the active principle expressed by the transgenic plant and the pest to be controlled correspond to anyone of the individualised combinations B.1 to B.1170 of table B.

Table 14: A method of controlling pests comprising the application of imidacloprid to transgenic cotton, wherein the combination of the active principle expressed by the transgenic plant and the pest to be controlled correspond to anyone of the individualised combinations B.1 to B.1170 of table B.

Table 15: A method of controlling pests comprising the application of imidacloprid to transgenic rice, wherein the combination of the active principle expressed by the transgenic plant and the pest to be controlled correspond to anyone of the individualised combinations B.1 to B.1170 of table B.

Table 16: A method of controlling pests comprising the application of imidacloprid to transgenic potatoes, wherein the combination of the active principle expressed by the transgenic plant and the pest to be controlled correspond to anyone of the individualised combinations B.1 to B.1170 of table B.

Table 17: A method of controlling pests comprising the application of imidacloprid to transgenic tomatoes, wherein the combination of the active principle expressed by the transgenic plant and the pest to be controlled correspond to anyone of the individualised combinations B.1 to B.1170 of table B.

Table 18: A method of controlling pests comprising the application of imidacloprid to transgenic cucurbits, wherein the combination of the active principle expressed by the transgenic plant and the pest to be controlled correspond to anyone of the individualised combinations B.1 to B.1170 of table B.

Table 19: A method of controlling pests comprising the application of imidacloprid to transgenic soybeans, wherein the combination of the active principle expressed by the transgenic plant and the pest to be controlled correspond to anyone of the individualised combinations B.1 to B.1170 of table B.

Table 20: A method of controlling pests comprising the application of imidacloprid to transgenic maize, wherein the combination of the active principle expressed by the transgenic plant and the pest to be controlled correspond to anyone of the individualised combinations B.1 to B.1170 of table B.

Table 21: A method of controlling pests comprising the application of imidacloprid to transgenic wheat, wherein the combination of the active principle expressed by the transgenic plant and the pest to be controlled correspond to anyone of the individualised combinations B.1 to B.1170 of table B.

Table 22: A method of controlling pests comprising the application of imidacloprid to transgenic bananas, wherein the combination of the active principle expressed by the transgenic plant and the pest to be controlled correspond to anyone of the individualised combinations B.1 to B.1170 of table B.

Table 23: A method of controlling pests comprising the application of imidacloprid to transgenic orange trees, wherein the combination of the active principle expressed by the transgenic plant and the pest to be controlled correspond to anyone of the individualised combinations B.1 to B.1170 of table B.

Table 24: A method of controlling pests comprising the application of imidacloprid to transgenic pome fruit, wherein the combination of the active principle expressed by the transgenic plant and the pest to be controlled correspond to anyone of the individualised combinations B.1 to B.1170 of table B.

Table 25: A method of controlling pests comprising the application of imidacloprid to transgenic cucurbits, wherein the combination of the active principle expressed by the transgenic plant and the pest to be controlled correspond to anyone of the individualised combinations B.1 to B.1170 of table B.

Table 26: A method of controlling pests comprising the application of imidacloprid to transgenic peppers, wherein the combination of the active principle expressed by the transgenic plant and the pest to be controlled correspond to anyone of the individualised combinations B.1 to B.1170 of table B.

Table 27: A method of controlling pests comprising the application of Ti-435 to transgenic cotton, wherein the combination of the active principle expressed by the transgenic plant and the pest to be controlled correspond to anyone of the individualised combinations B.1 to B.1170 of table B.

Table 28: A method of controlling pests comprising the application of Ti-435 to transgenic rice, wherein the combination of the active principle expressed by the transgenic plant and the pest to be controlled correspond to anyone of the individualised combinations B.1 to B.1170 of table B.

Table 29: A method of controlling pests comprising the application of Ti-435 to transgenic potatoes, wherein the combination of the active principle expressed by the transgenic plant and the pest to be controlled correspond to anyone of the individualised combinations B.1 to B.1170 of table B.

Table 30: A method of controlling pests comprising the application of Ti-435 to transgenic *brassica*, wherein the combination of the active principle expressed by the transgenic plant and the pest to be controlled correspond to anyone of the individualised combinations B.1 to B.1170 of table B.

Table 31: A method of controlling pests comprising the application of Ti-435 to transgenic tomatoes, wherein the combination of the active principle expressed by the trans- Table 32: A method of controlling pests comprising the application of Ti-435 to transgenic cucurbits, wherein the combination of the active principle expressed by the transgenic plant and the pest to be controlled correspond to anyone of the individualised combinations B.1 to B.1170 of table B.

Table 33: A method of controlling pests comprising the application of Ti-435 to transgenic soybeans, wherein the combination of the active principle expressed by the transgenic plant and the pest to be controlled correspond to anyone of the individualised combinations B.1 to B.1170 of table B.

Table 34: A method of controlling pests comprising the application of Ti-435 to transgenic maize, wherein the combination of the active principle expressed by the transgenic plant and the pest to be controlled correspond to anyone of the individualised combinations B.1 to B.1170 of table B.

Table 35: A method of controlling pests comprising the application of Ti-435 to transgenic wheat, wherein the combination of the active principle expressed by the transgenic plant and the pest to be controlled correspond to anyone of the individualised combinations B.1 to B.1170 of table B.

Table 36: A method of controlling pests comprising the application of Ti-435 to transgenic bananas, wherein the combination of the active principle expressed by the transgenic plant and the pest to be controlled correspond to anyone of the individualised combinations B.1 to B.1170 of table B.

Table 37: A method of controlling pests comprising the application of Ti-435 to transgenic citrus trees, wherein the combination of the active principle expressed by the transgenic plant and the pest to be controlled correspond to anyone of the individualised combinations B.1 to B.1170 of table B.

Table 38: A method of controlling pests comprising the application of Ti-435 to transgenic pome fruit trees, wherein the combination of the active principle expressed by the transgenic plant and the pest to be controlled correspond to anyone of the individualised combinations B.1 to B.1170 of table B.

Table 39: A method of controlling pests comprising the application of thiacloprid to transgenic cotton, wherein the combination of the active principle expressed by the transgenic plant and the pest to be controlled correspond to anyone of the individualised combinations B.1 to B.1170 of table B.

Table 40: A method of controlling pests comprising the application of thiacloprid to transgenic rice, wherein the combination of the active principle expressed by the transgenic plant and the pest to be controlled correspond to anyone of the individualised combinations B.1 to B.1170 of table B.

Table 41: A method of controlling pests comprising the application of thiacloprid to transgenic potatoes, wherein the combination of the active principle expressed by the transgenic plant and the pest to be controlled correspond to anyone of the individualised combinations B.1 to B.1170 of table B.

Table 42: A method of controlling pests comprising the application of thiacloprid to transgenic *brassica*, wherein the combination of the active principle expressed by the transgenic plant and the pest to be controlled correspond to anyone of the individualised combinations B.1 to B.1170 of table B.

Table 43: A method of controlling pests comprising the application of thiacloprid to transgenic tomatoes, wherein the combination of the active principle expressed by the transgenic plant and the pest to be controlled correspond to anyone of the individualised combinations B.1 to B.1170 of table B.

Table 44: A method of controlling pests comprising the application of thiacloprid to transgenic cucurbits, wherein the combination of the active principle expressed by the transgenic plant and the pest to be controlled correspond to anyone of the individualised combinations B.1 to B.1170 of table B.

Table 45: A method of controlling pests comprising the application of thiacloprid to transgenic soybeans, wherein the combination of the active principle expressed by the transgenic plant and the pest to be controlled correspond to anyone of the individualised combinations B.1 to B.1170 of table B.

Table 46: A method of controlling pests comprising the application of thiacloprid to transgenic maize, wherein the combination of the active principle expressed by the transgenic plant and the pest to be controlled correspond to anyone of the individualised combinations B.1 to B.1170 of table B.

Table 47: A method of controlling pests comprising the application of thiacloprid to transgenic wheat, wherein the combination of the active principle expressed by the transgenic plant and the pest to be controlled correspond to anyone of the individualised combinations B.1 to B.1170 of table B.

Table 48: A method of controlling pests comprising the application of thiacloprid to transgenic bananas, wherein the combination of the active principle expressed by the transgenic plant and the pest to be controlled correspond to anyone of the individualised combinations B.1 to B.1170 of table B.

TABLE C

| | Principle | Tolerant to | Crop |
|---|---|---|---|
| C.1 | ALS | Sulfonylureas etc.*** | Cotton |
| C.2 | ALS | Sulfonylureas etc.*** | Rice |
| C.3 | ALS | Sulfonylureas etc.*** | *Brassica* |
| C.4 | ALS | Sulfonylureas etc.*** | Potatoes |
| C.5 | ALS | Sulfonylureas etc.*** | Tomatoes |
| C.6 | ALS | Sulfonylureas etc.*** | Cucurbits |
| C.7 | ALS | Sulfonylureas etc.*** | Soybeans |
| C.8 | ALS | Sulfonylureas etc.*** | Maize |
| C.9 | ALS | Sulfonylureas etc.*** | Wheat |
| C.10 | ALS | Sulfonylureas etc.*** | pome fruit |
| C.11 | ALS | Sulfonylureas etc.*** | stone fruit |
| C.12 | ALS | Sulfonylureas etc.*** | *citrus* |
| C.13 | ACCase | +++ | Cotton |
| C.14 | ACCase | +++ | Rice |
| C.15 | ACCase | +++ | *Brassica* |
| C.16 | ACCase | +++ | Potatoes |
| C.17 | ACCase | +++ | Tomatoes |
| C.18 | ACCase | +++ | Cucurbits |
| C.19 | ACCase | +++ | Soybeans |
| C.20 | ACCase | +++ | Maize |
| C.21 | ACCase | +++ | Wheat |
| C.22 | ACCase | +++ | pome fruit |
| C.23 | ACCase | +++ | stone fruit |
| C.24 | ACCase | +++ | *citrus* |
| C.25 | HPPD | Isoxaflutol, Isoxachlotol, Sulcotrion, Mesotrion | Cotton |
| C.26 | HPPD | Isoxaflutol, Isoxachlotol, Sulcotrion, Mesotrion | Rice |
| C.27 | HPPD | Isoxaflutol, Isoxachlotol, Sulcotrion, Mesotrion | *Brassica* |
| C.28 | HPPD | Isoxaflutol, Isoxachlotol, Sulcotrion, Mesotrion | Potatoes |
| C.29 | HPPD | Isoxaflutol, Isoxachlotol, Sulcotrion, Mesotrion | Tomatoes |
| C.30 | HPPD | Isoxaflutol, Isoxachlotol, Sulcotrion, Mesotrion | Cucurbits |
| C.31 | HPPD | Isoxaflutol, Isoxachlotol, Sulcotrion, Mesotrion | Soybeans |

TABLE C-continued

| | Principle | Tolerant to | Crop |
|---|---|---|---|
| C.32 | HPPD | Isoxaflutol, Isoxachlotol, Sulcotrion, Mesotrion | Maize |
| C.33 | HPPD | Isoxaflutol, Isoxachlotol, Sulcotrion, Mesotrion | Wheat |
| C.34 | HPPD | Isoxaflutol, Isoxachlotol, Sulcotrion, Mesotrion | pome fruit |
| C.35 | HPPD | Isoxaflutol, Isoxachlotol, Sulcotrion, Mesotrion | stone fruit |
| C.36 | HPPD | Isoxaflutol, Isoxachlotol, Sulcotrion, Mesotrion | citrus |
| C.37 | Nitrilase | Bromoxynil, Ioxynil | Cotton |
| C.38 | Nitrilase | Bromoxynil, Ioxynil | Rice |
| C.39 | Nitrilase | Bromoxynil, Ioxynil | Brassica |
| C.40 | Nitrilase | Bromoxynil, Ioxynil | Potatoes |
| C.41 | Nitrilase | Bromoxynil, Ioxynil | Tomatoes |
| C.42 | Nitrilase | Bromoxynil, Ioxynil | Cucurbits |
| C.43 | Nitrilase | Bromoxynil, Ioxynil | Soybeans |
| C.44 | Nitrilase | Bromoxynil, Ioxynil | Maize |
| C.45 | Nitrilase | Bromoxynil, Ioxynil | Wheat |
| C.46 | Nitrilase | Bromoxynil, Ioxynil | pome fruit |
| C.47 | Nitrilase | Bromoxynil, Ioxynil | stone fruit |
| C.48 | Nitrilase | Bromoxynil, Ioxynil | citrus |
| C.49 | IPS | Chloroactanilides &&& | Cotton |
| C.50 | IPS | Chloroactanilides &&& | Rice |
| C.51 | IPS | Chloroactanilide &&&s | Brassica |
| C.52 | IPS | Chloroactanilides &&& | Potatoes |
| C.53 | IPS | Chloroactanilides &&& | Tomatoes |
| C.54 | IPS | Chloroactanilides &&& | Cucurbits |
| C.55 | IPS | Chloroactanilides &&& | Soybeans |
| C.56 | IPS | Chloroactanilides &&& | Maize |
| C.57 | IPS | Chloroactanilides &&& | Wheat |
| C.58 | IPS | Chloroactanilides &&& | pome fruit |
| C.59 | IPS | Chloroactanilides &&& | stone fruit |
| C.60 | IPS | Chloroactanilides &&& | citrus |
| C.61 | HOM | 2,4-D, Mecoprop-P | Cotton |
| C.62 | HOM | 2,4-D, Mecoprop-P | Rice |
| C.63 | HOM | 2,4-D, Mecoprop-P | Brassica |
| C.64 | HOM | 2,4-D, Mecoprop-P | Potatoes |
| C.65 | HOM | 2,4-D, Mecoprop-P | Tomatoes |
| C.66 | HOM | 2,4-D, Mecoprop-P | Cucurbits |
| C.67 | HOM | 2,4-D, Mecoprop-P | Soybeans |
| C.68 | HOM | 2,4-D, Mecoprop-P | Maize |
| C.69 | HOM | 2,4-D, Mecoprop-P | Wheat |
| C.70 | HOM | 2,4-D, Mecoprop-P | pome fruit |
| C.71 | HOM | 2,4-D, Mecoprop-P | stone fruit |
| C.72 | HOM | 2,4-D, Mecoprop-P | citrus |
| C.73 | PROTOX | Protox inhibitors /// | Cotton |
| C.74 | PROTOX | Protox inhibitors /// | Rice |
| C.75 | PROTOX | Protox inhibitors /// | Brassica |
| C.76 | PROTOX | Protox inhibitors /// | Potatoes |
| C.77 | PROTOX | Protox inhibitors /// | Tomatoes |
| C.78 | PROTOX | Protox inhibitors /// | Cucurbits |
| C.79 | PROTOX | Protox inhibitors /// | Soybeans |
| C.80 | PROTOX | Protox inhibitors /// | Maize |
| C.81 | PROTOX | Protox inhibitors /// | Wheat |
| C.82 | PROTOX | Protox inhibitors /// | pome fruit |
| C.83 | PROTOX | Protox inhibitors /// | stone fruit |
| C.84 | PROTOX | Protox inhibitors /// | citrus |
| C.85 | EPSPS | Glyphosate and/or Sulphosate | Cotton |
| C.86 | EPSPS | Glyphosate and/or Sulphosate | Rice |
| C.87 | EPSPS | Glyphosate and/or Sulphosate | Brassica |
| C.88 | EPSPS | Glyphosate and/or Sulphosate | Potatoes |
| C.89 | EPSPS | Glyphosate and/or Sulphosate | Tomatoes |
| C.90 | EPSPS | Glyphosate and/or Sulphosate | Cucurbits |
| C.91 | EPSPS | Glyphosate and/or Sulphosate | Soybeans |
| C.92 | EPSPS | Glyphosate and/or Sulphosate | Maize |
| C.93 | EPSPS | Glyphosate and/or Sulphosate | Wheat |
| C.94 | EPSPS | Glyphosate and/or Sulphosate | pome fruit |
| C.95 | EPSPS | Glyphosate and/or Sulphosate | stone fruit |
| C.96 | EPSPS | Glyphosate and/or Sulphosate | citrus |
| C.97 | GS | Gluphosinate and/or Bialaphos | Cotton |
| C.98 | GS | Gluphosinate and/or Bialaphos | Rice |
| C.99 | GS | Gluphosinate and/or Bialaphos | Brassica |
| C.100 | GS | Gluphosinate and/or Bialaphos | Potatoes |
| C.101 | GS | Gluphosinate and/or Bialaphos | Tomatoes |
| C.102 | GS | Gluphosinate and/or Bialaphos | Cucurbits |
| C.103 | GS | Gluphosinate and/or Bialaphos | Soybeans |
| C.104 | GS | Gluphosinate and/or Bialaphos | Maize |
| C.105 | GS | Gluphosinate and/or Bialaphos | Wheat |
| C.106 | GS | Gluphosinate and/or Bialaphos | pome fruit |
| C.107 | GS | Gluphosinate and/or Bialaphos | stone fruit |
| C.108 | GS | Gluphosinate and/or Bialaphos | citrus |

Abbreviations:
Acetyl-COA Carboxylase: ACCase
Acetolactate Synthase: ALS
Hydroxyphenylpyruvat dioxygenase: HPPD
Inhibition of protein synthesis: IPS
Hormone mimic: HO
Glutamine Synthetase: GS
Protoporphyrinogen oxidase: PROTOX
5-Enolpyruvyl-3-Phosphoshikimate Synthase: EPSPS
***Included are Sulfonylureas, Imidazolinones, Triazolopyrimidines, Dimethoxypyrimidines and N-Acylsulfonamides: Sulfonylureas such as Chlorsulfuron, Chlorimuron, Ethamethsulfuron, Metsulfuron, Primisulfuron, Prosulfuron, Triasulfuron, Cinosulfuron, Trifusulfuron, Oxasulfuron, Bensulfuron, Tribenuron, ACC 322140, Fluzasulfuron, Ethoxysulfuron, Fluzasulfuron, Nicosulfuron, Rimsulfuron, Thifensulfuron, Pyrazosulfuron, Clopyrasulfuron, NC 330, Azimsulfuron, Imazosulfuron, Sulfosulfuron, Amidosulfuron, Flupyrsulfuron, CGA 362622 Imidazolinones such as Imazamethabenz, Imazaquin, Imazamethypyr, Imazethapyr, Imazapyr and Imazamox; Triazolopyrimidines such as DE 511, Flumetsulam and Chloransulam; Dimethoxypyrimidines such as Pyrithiobac, Pyriminobac, Bispyribac and Pyribenzoxim.
+++ Tolerant to Diclofop-methyl, Fluazifop-P-butyl, Haloxyfop-P-methyl, Haloxyfop-P-ethyl, Quizalafop-P-ethyl, clodinafop propargyl, fenoxaprop--ethyl, -Tepraloxydim, Alloxydim, Sethoxydim, Cycloxydim, Cloproxydim, Tralkoxydim, Butoxydim, Caloxydim, Clefoxydim, Clethodim.
&&& Chloroacetanilides such as Alachlor Acetochlor, Dimethenamid
/// Protox inhibitors: For instance diphenyethers such as Acifluorfen, Aclonifen, Bifenox, Chlornitrofen, Ethoxyfen, Fluoroglycofen, Fomesafen, Lactofen, Oxyfluorfen; Imides such as Azafenidin, Carfentrazone-ethyl, Cinidon-ethyl, Flumiclorac-pentyl, Flumioxazin, Fluthiacet-methyl, Oxadiargyl, Oxadiazon, Pentoxazone, Sulfentrazone, Imides and others, such as Flumipropyn, Flupropacil, Nipyraclofen and Thidiazimin; and further Fluazolate and Pyraflufen-ethyl

BIOLOGICAL EXAMPLES

Table 49: A method of controlling representatives of the genus *Adoxophyes* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 50: A method of controlling representatives of the genus *Agrotis* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 51: A method of controlling *Alabama argillaceae* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 52: A method of controlling *Anticarsia gemmatalis* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 53: A method of controlling representatives of the genus *Chilo* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 54: A method of controlling *Clysia ambiguella* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 55: A method of controlling representatives of the genus *Cnephalocrocis* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 56: A method of controlling *Crocidolomia binotalis* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 57: A method of controlling representatives of the genus *Cydia* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 58: A method of controlling *Diparopsis castanea* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 59: A method of controlling representatives of the genus *Earias* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 60: A method of controlling representatives of the genus *Ephestia* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 61: A method of controlling representatives of the genus *Heliothis* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 62: A method of controlling *Hellula undalis* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 63: A method of controlling *Keiferia lycopersicella* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 64: A method of controlling *Leucoptera scitella* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 65: A method of controlling representatives of the genus *Lithocollethis* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 66: A method of controlling *Lobesia botrana* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 67: A method of controlling *Ostrinia nubilalis* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 68: A method of controlling representatives of the genus *Pandemis* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 69: A method of controlling *Pectinophora gossypiella* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 70: A method of controlling *Phyllocnistis citrella* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 71: A method of controlling representatives of the genus *Pieris* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 72: A method of controlling *Plutella xylostella* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 73: A method of controlling representatives of the genus *Scirpophaga* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 74: A method of controlling representatives of the genus *Sesamia* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 75: A method of controlling representatives of the genus *Sparganothis* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 76: A method of controlling representatives of the genus *Spodoptera* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 77: A method of controlling representatives of the genus *Tortrix* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 78: A method of controlling *Trichoplusia ni* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 79: A method of controlling representatives of the genus *Agriotes* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 80: A method of controlling *Anthonomus grandis* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 81: A method of controlling representatives of the genus *Curculio* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 82: A method of controlling *Diabrotica balteata* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 83: A method of controlling representatives of the genus *Leptinotarsa* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 84: A method of controlling representatives of the genus *Lissorhoptrus* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 85: A method of controlling representatives of the genus *Otiorhynchus* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 86: A method of controlling representatives of the genus *Aleurothrixus* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 87: A method of controlling representatives of the genus *Aleyrodes* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 88: A method of controlling representatives of the genus *Aonidiella* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 89: A method of controlling representatives of the family Aphididae comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 90: A method of controlling representatives of the genus *Aphis* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 91: A method of controlling *Bemisia tabaci* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 92: A method of controlling representatives of the genus *Empoasca* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 93: A method of controlling representatives of the genus *Mycus* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 94: A method of controlling representatives of the genus *Nephotettix* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 95: A method of controlling representatives of the genus *Nilaparvata* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 96: A method of controlling representatives of the genus *Pseudococcus* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 97: A method of controlling representatives of the genus *Psylla* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 98: A method of controlling representatives of the genus *Quadraspidiotus* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 99: A method of controlling representatives of the genus *Schizaphis* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 100: A method of controlling representatives of the genus *Trialeurodes* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 101: A method of controlling representatives of the genus *Lyriomyza* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 102: A method of controlling representatives of the genus *Oscinella* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 103: A method of controlling representatives of the genus *Phorbia* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 104: A method of controlling representatives of the genus *Frankliniella* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 105: A method of controlling representatives of the genus *Thrips* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 106: A method of controlling *Scirtothrips aurantii* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 107: A method of controlling representatives of the genus *Aceria* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 108: A method of controlling representatives of the genus *Aculus* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 109: A method of controlling representatives of the genus *Brevipalpus* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 110: A method of controlling representatives of the genus *Panonychus* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 111: A method of controlling representatives of the genus *Phyllocoptruta* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 112: A method of controlling representatives of the genus *Tetranychus* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 113: A method of controlling representatives of the genus *Heterodera* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 114: A method of controlling representatives of the genus *Meloidogyne* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 115: A method of controlling *Mamestra brassica* comprising the application of thiamethoxam to a herbicidally resistant transgenic crop, wherein the combination of the active principle expressed by the transgenic plant and the crop to be protected against the pest correspond to anyone of the lines C.1 to C.108 of table C.

Table 116: A method of controlling representatives of the genus *Adoxophyes* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 117: A method of controlling representatives of the genus *Agrotis* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 118: A method of controlling *Alabama argillaceae* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 119: A method of controlling *Anticarsia gemmatalis* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 120: A method of controlling representatives of the genus *Chilo* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 121: A method of controlling *Clysia ambiguella* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 122: A method of controlling representatives of the genus *Cnephalocrocis* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 123: A method of controlling *Crocidolomia binotalis* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 124: A method of controlling representatives of the genus *Cydia* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 125: A method of controlling *Diparopsis castanea* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 126: A method of controlling representatives of the genus *Earias* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 127: A method of controlling representatives of the genus *Ephestia* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 128: A method of controlling representatives of the genus *Heliothis* of imidacloprid to a herbicidally resistant transgenic crop, wherein the combination of the active principle expressed by the transgenic plant and the crop to be protected against the pest correspond to anyone of the lines C.1 to C.108 of table C.

Table 129: A method of controlling *Hellula undalis* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 130: A method of controlling *Keiferia lycopersicella* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 131: A method of controlling *Leucoptera scitella* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 132: A method of controlling representatives of the genus *Lithocollethis* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 133: A method of controlling *Lobesia botrana* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 134: A method of controlling *Ostrinia nubilalis* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 135: A method of controlling representatives of the genus *Pandemis* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 136: A method of controlling *Pectinophora gossypiella* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 137: A method of controlling *Phyllocnistis citrella* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 138: A method of controlling representatives of the genus *Pieris* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 139: A method of controlling *Plutella xylostella* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 140: A method of controlling representatives of the genus *Scirpophaga* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 141: A method of controlling representatives of the genus *Sesamia* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 142: A method of controlling representatives of the genus *Sparganothis* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 143: A method of controlling representatives of the genus *Spodoptera* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 144: A method of controlling representatives of the genus *Tortrix* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 145: A method of controlling *Trichoplusia ni* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 146: A method of controlling representatives of the genus *Agriotes* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 147: A method of controlling *Anthonomus grandis* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 148: A method of controlling representatives of the genus *Curculio* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 149: A method of controlling *Diabrotica balteata* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 150: A method of controlling representatives of the genus *Leptinotarsa* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 151: A method of controlling representatives of the genus *Lissorhoptrus* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 152: A method of controlling representatives of the genus *Otiorhynchus* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 153: A method of controlling representatives of the genus *Aleurothrixus* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 154: A method of controlling representatives of the genus *Aleyrodes* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 155: A method of controlling representatives of the genus *Aonidiella* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 156: A method of controlling representatives of the family Aphididae comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 157: A method of controlling representatives of the genus *Aphis* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 158: A method of controlling *Bemisia tabaci* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 159: A method of controlling representatives of the genus *Empoasca* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 160: A method of controlling representatives of the genus *Mycus* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 161: A method of controlling representatives of the genus *Nephotettix* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 162: A method of controlling representatives of the genus *Nilaparvata* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 163: A method of controlling representatives of the genus *Pseudococcus* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 164: A method of controlling representatives of the genus *Psylla* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 165: A method of controlling representatives of the genus *Quadraspidiotus* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 166: A method of controlling representatives of the genus *Schizaphis* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 167: A method of controlling representatives of the genus *Trialeurodes* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 168: A method of controlling representatives of the genus *Lyriomyza* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 169: A method of controlling representatives of the genus *Oscinella* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 170: A method of controlling representatives of the genus *Phorbia* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 171: A method of controlling representatives of the genus *Frankliniella* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 172: A method of controlling representatives of the genus *Thrips* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 173: A method of controlling *Scirtothrips aurantii* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 174: A method of controlling representatives of the genus *Aceria* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 175: A method of controlling representatives of the genus *Aculus* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 176: A method of controlling representatives of the genus *Brevipalpus* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 177: A method of controlling representatives of the genus *Panonychus* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 178: A method of controlling representatives of the genus *Phyllocoptruta* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 179: A method of controlling representatives of the genus *Tetranychus* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 180: A method of controlling representatives of the genus *Heterodera* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 181: A method of controlling representatives of the genus *Meloidogyne* comprising the application of imidacloprid to a herbicidally resistant transgenic crop, wherein the combination of the active principle expressed by the transgenic plant and the crop to be protected against the pest correspond to anyone of the lines C.1 to C.108 of table C.

Table 182: A method of controlling representatives of the genus *Adoxophyes* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 183: A method of controlling representatives of the genus *Agrotis* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 184: A method of controlling *Alabama argillaceae* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 185: A method of controlling *Anticarsia gemmatalis* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 186: A method of controlling representatives of the genus *Chilo* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 187: A method of controlling *Clysia ambiguella* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 188: A method of controlling *Crocidolomia binotalis* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 189: A method of controlling representatives of the genus *Cydia* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 190: A method of controlling *Diparopsis castanea* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 191: A method of controlling representatives of the genus *Earias* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 192: A method of controlling representatives of the genus *Ephestia* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 193: A method of controlling representatives of the genus *Heliothis* of Ti-435 to a herbicidally resistant transgenic crop, wherein the combination of the active principle expressed by the transgenic plant and the crop to be protected against the pest correspond to anyone of the lines C.1 to C.108 of table C.

Table 194: A method of controlling *Hellula undalis* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 195: A method of controlling *Keiferia lycopersicella* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 196: A method of controlling *Leucoptera scitella* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 197: A method of controlling representatives of the genus *Lithocollethis* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 198: A method of controlling *Lobesia botrana* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 199: A method of controlling *Ostrinia nubilalis* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 200: A method of controlling representatives of the genus *Pandemis* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 201: A method of controlling *Pectinophora gossypiella* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 202: A method of controlling *Phyllocnistis citrella* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 203: A method of controlling representatives of the genus *Pieris* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 204: A method of controlling *Plutella xylostella* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 205: A method of controlling representatives of the genus *Scirpophaga* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 206: A method of controlling representatives of the genus *Sesamia* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 207: A method of controlling representatives of the genus *Sparganothis* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 208: A method of controlling representatives of the genus *Spodoptera* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 209: A method of controlling representatives of the genus *Tortrix* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 210: A method of controlling *Trichoplusia ni* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 211: A method of controlling representatives of the genus *Agriotes* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 212: A method of controlling *Anthonomus grandis* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 213: A method of controlling representatives of the genus *Curculio* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 214: A method of controlling *Diabrotica balteata* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 215: A method of controlling representatives of the genus *Leptinotarsa* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 216: A method of controlling representatives of the genus *Lissorhoptrus* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 217: A method of controlling representatives of the genus *Otiorhynchus* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 218: A method of controlling representatives of the genus *Aleurothrixus* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 219: A method of controlling representatives of the genus *Aleyrodes* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 220: A method of controlling representatives of the genus *Aonidiella* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 221: A method of controlling representatives of the family Aphididae comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 222: A method of controlling representatives of the genus *Aphis* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 223: A method of controlling *Bemisia tabaci* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 224: A method of controlling representatives of the genus *Empoasca* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 225: A method of controlling representatives of the genus *Mycus* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 226: A method of controlling representatives of the genus *Nephotettix* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 227: A method of controlling representatives of the genus *Nilaparvata* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 228: A method of controlling representatives of the genus *Pseudococcus* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 229: A method of controlling representatives of the genus *Psylla* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 230: A method of controlling representatives of the genus *Quadraspidiotus* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 231: A method of controlling representatives of the genus *Schizaphis* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 232: A method of controlling representatives of the genus *Trialeurodes* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 233: A method of controlling representatives of the genus *Lyriomyza* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 234: A method of controlling representatives of the genus *Oscinella* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 235: A method of controlling representatives of the genus *Phorbia* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 236: A method of controlling representatives of the genus *Frankliniella* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 237: A method of controlling representatives of the genus *Thrips* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 238: A method of controlling *Scirtothrips aurantii* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 239: A method of controlling representatives of the genus *Aceria* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 240: A method of controlling representatives of the genus *Aculus* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 241: A method of controlling representatives of the genus *Brevipalpus* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 242: A method of controlling representatives of the genus *Panonychus* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 243: A method of controlling representatives of the genus *Phyllocoptruta* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 244: A method of controlling representatives of the genus *Tetranychus* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 245: A method of controlling representatives of the genus *Heterodera* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 246: A method of controlling representatives of the genus *Meloidogyne* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Table 247: A method of controlling *Mamestra brassica* comprising the application of Ti-435 to a herbicidally resistant transgenic crop, wherein the combination of the active principle expressed by the transgenic plant and the crop to be protected against the pest correspond to anyone of the lines C.1 to C.108 of table C.

Example B1

Action Against *Anthonomus grandis* Adults, *Spodoptera littoralis* or *Heliothis virescens*

Young transgenic cotton plants which express the δ-endotoxin CryIIIA are sprayed with an aqueous emulsion spray mixture comprising 100, 50, 10, 5, 1 ppm of imidacloprid respectively. After the spray coating has dried on, the cotton plants are populated with 10 adult *Anthonomus grandis*, 10 *Spodoptera littoralis* larvae or 10 *Heliothis virescens* larvae respectively and introduced into a plastic container. Evaluation takes place 3 to 10 days later. The percentage reduction in population, or the percentage reduction in feeding damage (% action), is determined by comparing the number of dead beetles and the feeding damage on the transgenic cotton plants with that of non-transgenic cotton plants which have been treated with an emulsion spray mixture comprising imidacloprid and conventional CryIIIA-toxin at a concentration of in each case 100, 50, 10, 5, 1 ppm respectively.

In this test, the control of the tested insects in the transgenic plant is superior to the control on the non-transgenic plant.

Example B2

Action Against *Anthonomus grandis* Adults, *Spodoptera littoralis* or *Heliothis virescens*

Young transgenic cotton plants which express the δ-endotoxin CryIIIA are sprayed with an aqueous emulsion spray mixture comprising 100, 50, 10, 5, 1 ppm of thiamethoxam respectively. After the spray coating has dried on, the cotton plants are populated with 10 adult *Anthonomus grandis,* 10 *Spodoptera littoralis* larvae or 10 *Heliothis virescens* larvae respectively and introduced into a plastic container. Evaluation takes place 3 to 10 days later. The percentage reduction in population, or the percentage reduction in feeding damage (% action), is determined by comparing the number of dead beetles and the feeding damage on the transgenic cotton plants with that of non-transgenic cotton plants which have been treated with an emulsion spray mixture comprising thiamethoxam and conventional CryIIIA-toxin at a concentration of in each case 100, 50, 10, 5, 1 ppm respectively.

In this test, the control of the tested insects in the transgenic plant is superior, while it is insufficient in the non-transgenic plant.

Example B3

Action Against *Anthonomus grandis* Adults, *Spodoptera littoralis* or *Heliothis virescens*

Young transgenic cotton plants which express the δ-endotoxin CryIIIA are sprayed with an aqueous emulsion spray mixture comprising 100, 50, 10, 5, 1 ppm of Ti-435 respectively. After the spray coating has dried on, the cotton plants are populated with 10 adult *Anthonomus grandis,* 10 *Spodoptera littoralis* larvae or 10 *Heliothis virescens* larvae respectively and introduced into a plastic container. Evaluation takes place 3 to 10 days later. The percentage reduction in population, or the percentage reduction in feeding damage (% action), is determined by comparing the number of dead beetles and the feeding damage on the transgenic cotton plants with that of non-transgenic cotton plants which have been treated with an emulsion spray mixture comprising Ti-435 and conventional CryIIIA-toxin at a concentration of in each case 100, 50, 10, 5, 1 ppm respectively.

In this test, the control of the tested insects in the transgenic plant is superior, while it is insufficient in the non-transgenic plant.

Example B4

Action Against *Anthonomus grandis* Adults, *Spodoptera littoralis* or *Heliothis virescens*

Young transgenic cotton plants which express the δ-endotoxin CryIa(c) are sprayed with an aqueous emulsion spray mixture comprising 100, 50, 10, 5, 1 ppm of Ti-435 respectively. After the spray coating has dried on, the cotton plants are populated with 10 adult *Anthonomus grandis,* 10 *Spodoptera littoralis* larvae or 10 *Heliothis virescens* larvae respectively and introduced into a plastic container. Evaluation takes place 3 to 10 days later. The percentage reduction in population, or the percentage reduction in feeding damage (% action), is determined by comparing the number of dead beetles and the feeding damage on the transgenic cotton plants with that of non-transgenic cotton plants which have been treated with an emulsion spray mixture comprising Ti-435 and conventional CryIIIA-toxin at a concentration of in each case 100, 50, 10, 5, 1 ppm respectively.

In this test, the control of the tested insects in the transgenic plant is superior, while it is insufficient in the non-transgenic plant.

Example B5

Action Against *Anthonomus grandis* Adults *Spodoptera littoralis* or *Heliothis virescens*

Young transgenic cotton plants which express the δ-endotoxin CryIa(c) are sprayed with an aqueous emulsion spray mixture comprising 100, 50, 10, 5, 1 ppm of thiamethoxam respectively. After the spray coating has dried on, the cotton plants are populated with 10 adult *Anthonomus grandis,* 10 *Spodoptera littoralis* larvae or 10 *Heliothis virescens* larvae respectively and introduced into a plastic container. Evaluation takes place 3 to 10 days later. The percentage reduction in population, or the percentage reduction in feeding damage (% action), is determined by comparing the number of dead beetles and the feeding damage on the transgenic cotton plants with that of non-transgenic cotton plants which have been treated with an emulsion spray mixture comprising thiamethoxam and conventional CryIIIA-toxin at a concentration of in each case 100, 50, 10, 5, 1 ppm respectively.

In this test, the control of the tested insects in the transgenic plant is superior, while it is insufficient in the non-transgenic plant.

Example B6

Action Against *Anthonomus grandis* Adults *Spodoptera littoralis* or *Heliothis virescens*

Young transgenic cotton plants which express the δ-endotoxin CryIa(c) are sprayed with an aqueous emulsion spray mixture comprising 100, 50, 10, 5, 1 ppm of imidacloprid respectively. After the spray coating has dried on, the cotton plants are populated with 10 adult *Anthonomus grandis,* 10 *Spodoptera littoralis* larvae or 10 *Heliothis virescens* larvae respectively and introduced into a plastic container. Evaluation takes place 3 to 10 days later. The percentage reduction in population, or the percentage reduction in feeding damage (% action), is determined by comparing the number of dead beetles and the feeding damage on the transgenic cotton plants with that of non-transgenic cotton plants which have been treated with an emulsion spray mixture comprising imidacloprid conventional CryIIIA-toxin at a concentration of in each case 100, 50, 10, 5, 1 ppm respectively.

In this test, the control of the tested insects in the transgenic plant is superior, while it is insufficient in the non-transgenic plant.

Example B7

Action Against *Ostrinia nubilalis, Spodoptera* spp. or *Heliothis* spp

A plot (a) planted with maize cv. KnockOut® and an adjacent plot (b) of the same size which is planted with conventional maize, both showing natural infestation with *Ostrinia nubilalis, Spodoptera* spp. or *Heliothis*, are sprayed with an aqueous emulsion spray mixture comprising 200, 100, 50, 10, 5, 1 ppm of Ti-435. Immediately afterwards, plot (b) is treated with an emulsion spray mixture comprising 200, 100, 50, 10, 5, 1 ppm of the endotoxin expressed by KnockOut®. Evaluation takes place 6 days later. The percentage reduction in population (% action) is determined by comparing the number of dead pests on the plants of plot (a) with that on the plants of plot (b).

Improved control of *Ostrinia nubilalis, Spodoptera* spp. or *Heliothis* is observed on the plants of plot (a), while plot (b) shows a control level of not over 60%.

Example B8

Action Against *Ostrinia nubilalis, Spodoptera* spp. or *Heliothis* spp

A plot (a) planted with maize cv. KnockOut® and an adjacent plot (b) of the same size which is planted with conventional maize, both showing natural infestation with *Ostrinia nubilalis, Spodoptera* spp. or *Heliothis*, are sprayed with an aqueous emulsion spray mixture comprising 200, 100, 50, 10, 5, 1 ppm of thiamethoxam. Immediately afterwards, plot (b) is treated with an emulsion spray mixture comprising 200, 100, 50, 10, 5, 1 ppm of the endotoxin expressed by Knock-Out®. Evaluation takes place 6 days later. The percentage reduction in population (% action) is determined by comparing the number of dead pests on the plants of plot (a) with that on the plants of plot (b).

Improved control of *Ostrinia nubilalis, Spodoptera* spp. or *Heliothis* is observed on the plants of plot (a), while plot (b) shows a control level of not over 60%.

Example B9

Action Against *Ostrinia nubilalis, Spodoptera* spp. or *Heliothis* spp

A plot (a) planted with maize cv. KnockOut® and an adjacent plot (b) of the same size which is planted with conventional maize, both showing natural infestation with *Ostrinia nubilalis, Spodoptera* spp. or *Heliothis*, are sprayed with an aqueous emulsion spray mixture comprising 200, 100, 50, 10, 5, 1 ppm of imidacloprid. Immediately afterwards, plot (b) is treated with an emulsion spray mixture comprising 200, 100, 50, 10, 5, 1 ppm of the endotoxin expressed by KnockOut®. Evaluation takes place 6 days later. The percentage reduction in population (% action) is determined by comparing the number of dead pests on the plants of plot (a) with that on the plants of plot (b).

Improved control of *Ostrinia nubilalis, Spodoptera* spp. or *Heliothis* spp. is observed on the plants of plot (a), while plot (b) shows a control level of not over 60%.

Example B10

Action Against *Diabrotica balteata*

A plot (a) planted with maize seedlings cv. KnockOut® and an adjacent plot (b) of the same size which is planted with conventional maize are sprayed with an aqueous emulsion of a spray mixture comprising 400 ppm thiamethoxam. Immediately afterwards, plot (b) is treated with an emulsion spray mixture comprising 400 ppm of the endotoxin expressed by KnockOut®. After the spray coating has dried on, the seedlings are populated with 10 *Diabrotica balteata* larvae in the second stage and transferred to a plastic container. The test is evaluated 6 days later. The percentage reduction in population (% action) is determined by comparing the number of dead pests on the plants of plot (a) with that on the plants of plot (b).

Improved control of *Diabrotica balteata* is observed on the plants of plot (a), while plot (b) shows a control level of not over 60%.

Example B11

Action Against *Aphis gossypii*

Cotton seedlings on a plot (a) expressing the δ-endotoxin CryIIIa on a plot (a) and conventional cotton seedlings on a plot (b) are infected with *Aphis gossypi* and subsequently sprayed with a spray mixture comprising 400 ppm thiamethoxam. Immediately afterwards, plot (b) is treated with an emulsion spray mixture comprising 400 ppm of the δ-endotoxin CryIIIa. The seedlings of plot (a) and (b) are then incubated at 20° C. The test is evaluated after 3 and 6 days.

The percentage reduction in population (% action) is determined by comparing the number of dead pests on the plants of plot (a) with that on the plants of plot (b). Improved control of *Aphis gossypi* is observed on the plants of plot (a), while plot (b) shows a control level of not over 60%.

Example B12

Action against *Frankliniella occidentalis*

Cotton seedlings expressing the δ-endotoxin CryIIIa on a plot (a) and conventional cotton seedlings on a plot (b) are infected with *Frankliniella occidentalis* and subsequently sprayed with a spray mixture comprising 400 ppm thiamethoxam. Immediately afterwards, plot (b) is treated with an emulsion spray mixture comprising 400 ppm of the δ-endotoxin CryIIIa. The seedlings of plot (a) and (b) are then incubated at 20° C. The test is evaluated after 3 and 6 days.

The percentage reduction in population (% action) is determined by comparing the number of dead pests on the plants of plot (a) with that on the plants of plot (b). Improved control of *Frankliniella occidentalis* is observed on the plants of plot (a), while plot (b) shows a control level of not over 60%.

Example B13

Action Against *Aphis gossypii*

Cotton seedlings expressing the δ-endotoxin CryIA(c) on a plot (a) and conventional cotton seedlings on a plot (b) are infected with *Aphis gossypii* and subsequently sprayed with a spray mixture comprising 400 ppm thiamethoxam. Immediately afterwards, plot (b) is treated with an emulsion spray mixture comprising 400 ppm of the δ-endotoxin CryIIIa. The seedlings of plot (a) and (b) are then incubated at 20° C. The test is evaluated after 3 and 6 days.

The percentage reduction in population (% action) is determined by comparing the number of dead pests on the plants of plot (a) with that on the plants of plot (b). Improved control of *Aphis gossypii* is observed on the plants of plot (a), while plot (b) shows a control level of not over 60%.

Example B14

Action Against *Frankliniella occidentalis*

Cotton seedlings expressing the δ-endotoxin CryIa(c) on a plot (a) and conventional cotton seedlings on a plot (b) are infected with *Frankliniella occidentalis* and subsequently sprayed with a spray mixture comprising 400 ppm thiamethoxam. Immediately afterwards, plot (b) is treated with an emulsion spray mixture comprising 400 ppm of the δ-endotoxin CryIa(c). The seedlings of plot (a) and (b) are then incubated at 20° C. The test is evaluated after 3 and 6 days.

The percentage reduction in population (% action) is determined by comparing the number of dead pests on the plants of plot (a) with that on the plants of plot (b). Improved control of *Frankliniella occidentalis* is observed on the plants of plot (a), while plot (b) shows a control level of not over 60%.

Example B15

Action Against *Nephotettix cincticeps*

Rice plants on a plot (a) expressing the δ-endotoxin CryIA (b) and conventional rice plants on a plot (b) are sprayed with a spray mixture comprising 400 ppm thiamethoxam. Immediately afterwards, plot (b) is treated with an emulsion spray mixture comprising 400 ppm of the δ-endotoxin CryIA(b). After the spray coating has dried on, the plants are infected with *Nephotettix cincticeps* of the 2nd and 3rd stages. The seedlings of plot (a) and (b) are then incubated at 20° C. The test is evaluated after 21 days.

The percentage reduction in population (% action) is determined by comparing the number of dead pests on the plants of plot (a) with that on the plants of plot (b). Improved control of *Nephotettix cincticeps* is observed on the plants of plot (a), while plot (b) shows a control level of not over 60%.

Example B16

Action Against *Nephotettix cincticeps* (Systemic)

Rice plants expressing the δ-endotoxin CryIa(b) are planted in a in pot (A) and conventional ice plants are planted in a pot (B). Pot (A) is placed in an aqueous emulsion containing 400 ppm thiamethoxam, whereas plot (B) is placed in a pot containing 400 ppm thiamethoxam and 400 ppm of the δ-endotoxin CryI(b). The plants are subsequently infected with *Nephotettix cincticeps* larvae of the second and third stage. The test is evaluated after 6 days.

The percentage reduction in population (% action) is determined by comparing the number of dead pests on the plants of pot (A) with that on the plants of pot (B). Improved control of *Nephotettix cincticeps* is observed on the plants of pot (A), while pot (B) shows a control level of not over 60%.

Example B17

Action Against *Nilaparvata lugens*

Rice plants on a plot (a) expressing the δ-endotoxin CryIA (b) and conventional rice plants on a plot (b) are infected with *Nilaparvata lugens*, subsequently sprayed with a spray mixture comprising 400 ppm thiamethoxam. Immediately afterwards, plot (b) is treated with an emulsion spray mixture comprising 400 ppm of the δ-endotoxin CryIA(b). The seedlings of plot (a) and (b) are then incubated at 20° C. The test is evaluated after 21 days.

The percentage reduction in population (% action) is determined by comparing the number of dead pests on the plants of plot (a) with that on the plants of plot (b). Improved control of *Nilaparvata lugens* is observed on the plants of plot (a), while plot (b) shows a control level of not over 60%.

Example B18

Action Against *Nilaparvata lugens* (Systemic)

Rice plants expressing the δ-endotoxin CryIA(b) are planted in a in pot (A) and conventional rice plants are planted in a pot (B). Pot (A) is placed in an aqueous emulsion containing 400 ppm thiamethoxam, whereas plot (B) is place in a pot containing 400 ppm thiamethoxam and 400 ppm of the δ-endotoxin CryIA(b). The plants are subsequently infected with *Nilaparvata lugens* larvae of the second and third stage. The test is evaluated after 6 days.

The percentage reduction in population (% action) is determined by comparing the number of dead pests on the plants of pot (A) with that on the plants of pot (B). Improved control of *Nephotettix cincticeps* is observed on the plants of pot (A), while pot (B) shows a control level of not over 60%.

Example B19

Action Against *Nephotettix cincticeps*

Rice plants on a plot (a) expressing the δ-endotoxin CryIA (c) and conventional rice plants on a plot (b) are sprayed with a spray mixture comprising 400 ppm thiamethoxam. Immediately afterwards, plot (b) is treated with an emulsion spray mixture comprising 400 ppm of the δ-endotoxin CryIA(c). After the spray coating has dried on, the plants are infected with *Nephotettix cincticeps* of the 2nd and 3rd stages. The seedlings of plot (a) and (b) are then incubated at 20° C. The test is evaluated after 21 days.

The percentage reduction in population (% action) is determined by comparing the number of dead pests on the plants of plot (a) with that on the plants of plot (b). Improved control of *Nephotettix cincticeps* is observed on the plants of plot (a), while plot (b) shows a control level of not over 60%.

Example B20

Action Against *Nephotettix cincticeps* (Systemic)

Rice plants expressing the δ-endotoxin CryIa(c) are planted in a in pot (A) and conventional ice plants are planted in a pot (B). Pot (A) is placed in an aqueous emulsion containing 400 ppm thiamethoxam, whereas plot (B) is placed in a pot containing 400 ppm thiamethoxam and 400 ppm of the δ-endotoxin CryI(c). The plants are subsequently infected with *Nephotettix cincticeps* larvae of the second and third stage. The test is evaluated after 6 days.

The percentage reduction in population (% action) is determined by comparing the number of dead pests on the plants of pot (A) with that on the plants of pot (B). Improved control of *Nephotettix cincticeps* is observed on the plants of pot (A), while pot (B) shows a control level of not over 60%.

Example B21

Action Against *Nilaparvata lugens*

Rice plants on a plot (a) expressing the δ-endotoxin CryIA (c) and conventional rice plants on a plot (b) are infected with *Nilaparvata lugens*, subsequently sprayed with a spray mixture comprising 400 ppm thiamethoxam. Immediately afterwards, plot (b) is treated with an emulsion spray mixture comprising 400 ppm of the δ-endotoxin CryIA(c). The seedlings of plot (a) and (b) are then incubated at 20° C. The test is evaluated after 21 days.

The percentage reduction in population (% action) is determined by comparing the number of dead pests on the plants of plot (a) with that on the plants of plot (b). Improved control of *Nilaparvata lugens* is observed on the plants of plot (a), while plot (b) shows a control level of not over 0%.

Example B22

Action Against *Nilaparvata lugens (Systemic)*

Rice plants expressing the δ-endotoxin CryIA(c) are planted in a in pot (A) and conventional rice plants are planted in a pot (B). Pot (A) is placed in an aqueous emulsion containing 400 ppm thiamethoxam, whereas plot (B) is place in a pot containing 400 ppm thiamethoxam and 400 ppm of the δ-endotoxin CryIA(c). The plants are subsequently infected with *Nilaparvata lugens* larvae of the second and third stage. The test is evaluated after 6 days.

The percentage reduction in population (% action) is determined by comparing the number of dead pests on the plants of pot (A) with that on the plants of pot (B). Improved control of *Nephotettix cincticeps* is observed on the plants of pot (A), while pot (B) shows a control level of not over 60%.

The invention claimed is:

1. A method of controlling pests in crops of a transgenic useful plant comprising the application of thiacloprid, in free form or in agrochemically useful salt form as active ingredient and at least one auxiliary to the pests, the transgenic useful plant or propagation material thereof.

2. The method of claim 1 where the transgenic useful plant contains one or more genes which encode insectidical resistance and express one or more active toxins.

3. The method of claim 2 wherein the active toxin expressed by the transgenic useful plant is selected from *Bacillus cereus* proteins, *Bacillus poplia* proteins, *Bacillus thuringiensis* endotoxins(B.t.), insecticidal proteins of bateria colonising nematodes, proteinase inhibitors, ribosome inactivating proteins, plant lectins, animal toxins, and steroid metabolism enzymes.

4. The method of claim 2 wherein the active toxin expressed by the transgenic useful plant is selected from CryIA(a), CryIA(b), CryIA(c), Cry IIA, CryIIIA, CryIIIB2, CytA, VIP3, GL, PL, XN, Plnh., Plec., Aggl., CO, CH, SS, and HO.

5. The method of claim 1 where the crops of a transgenic useful plant are selected from rice, potatoes, *brassica*, tomatoes, cucurbits, soybeans, maize, wheat, bananas, citrus trees, pome fruit trees and peppers.

6. The method of claim 1 wherein thiacloprid is applied to the transgenic useful plant.

7. The method of claim 1 wherein thiacloprid is applied to the propagation material of the transgenic useful plant.

8. The method of claim 7 wherein the propagation material is seed.

* * * * *